United States Patent
Pegg et al.

(10) Patent No.: US 10,647,704 B2
(45) Date of Patent: May 12, 2020

(54) PHARMACEUTICAL COMPOUNDS

(71) Applicant: CELLCENTRIC LTD, Cambridge, Cambridgeshire (GB)

(72) Inventors: Neil Anthony Pegg, Cambridge (GB); David Michel Adrien Taddei, Nottingham (GB); Jonathan Shannon, Nottingham (GB); Silvia Paoletta, Nottingham (GB); Ting Qin, Nottingham (GB); Gareth Harbottle, Nottingham (GB)

(73) Assignee: CELLCENTRIC LTD, Cambridge, Cambridgeshire (GB)

( * ) Notice: Subject to any disclaimer, the term of this patent is extended or adjusted under 35 U.S.C. 154(b) by 0 days.

(21) Appl. No.: 16/341,650

(22) PCT Filed: Oct. 18, 2017

(86) PCT No.: PCT/GB2017/053153
§ 371 (c)(1),
(2) Date: Apr. 12, 2019

(87) PCT Pub. No.: WO2018/073587
PCT Pub. Date: Apr. 26, 2018

(65) Prior Publication Data
US 2019/0263788 A1 Aug. 29, 2019

(30) Foreign Application Priority Data
Oct. 18, 2016 (GB) .................................. 1617627.3

(51) Int. Cl.
| C07D 401/14 | (2006.01) |
| C07D 403/14 | (2006.01) |
| A61P 35/00 | (2006.01) |
| C07D 401/04 | (2006.01) |
| A61K 9/20 | (2006.01) |
| C07D 403/04 | (2006.01) |
| A61K 9/00 | (2006.01) |
| A61K 31/4184 | (2006.01) |
| A61K 45/06 | (2006.01) |

(52) U.S. Cl.
CPC .......... C07D 403/14 (2013.01); A61K 9/0019 (2013.01); A61K 9/2018 (2013.01); A61K 9/2059 (2013.01); A61K 31/4184 (2013.01); A61P 35/00 (2018.01); C07D 401/04 (2013.01); C07D 401/14 (2013.01); C07D 403/04 (2013.01); A61K 45/06 (2013.01)

(58) Field of Classification Search
CPC ............................ C07D 403/14; C07D 401/14
See application file for complete search history.

(56) References Cited

U.S. PATENT DOCUMENTS

2010/0179147 A1   7/2010 Chang et al.

FOREIGN PATENT DOCUMENTS

| EP | 2397471 A1 | 12/2011 |
| WO | 2014182929 A1 | 11/2014 |
| WO | 2016086200 A1 | 6/2016 |
| WO | 2016097870 A1 | 6/2016 |
| WO | 2016170324 A1 | 10/2016 |
| WO | 2017024412 A1 | 2/2017 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Ghosh et al., "Regulatory T Cell Modulation by CBP/EP300 Bromodomain Inhibition", The Journal of Biological Chemistry, Jun. 17, 2016, vol. 291, No. 25, pp. 13014-13027.
Jones et al., "The Epigenomics of Cancer", Cell, Feb. 23, 2007, vol. 128, pp. 683-692.
Zhong et al., "p300 Acetyltransferase Regulates Androgen Receptor Degradation and PTEN-Deficient Prostate Tumorigenesis", Cancer Research, Mar. 15, 2014, vol. 74, No. 6, pp. 1870-1880.
Cai et al., "Intratumoral De Novo Steroid Synthesis Activates Androgen Receptor in Castration-Resistant Prostate Cancer and Is Upregulated by Treatment with CYP17A1 Inhibitors", Cancer Research, Oct. 15, 2011, vol. 71, No. 20, pp. 6503-6513.
Hay et al., "Discovery and Optimization of Small-Molecule Ligands for the CBP/p300 Bromodomains", J. Am. Chem. Soc., 2014, vol. 136, pp. 9308-9319 with Supporting Information (S1-S99).

(Continued)

*Primary Examiner* — Shawquia Jackson
(74) *Attorney, Agent, or Firm* — MH2 Technology Law Group, LLP

(57) ABSTRACT

A compound which is a benzimidazole of formula (I): wherein X is a 5-membered heteroaryl group selected from the following: or a pharmaceutically acceptable salt thereof. The compound has activity in modulating the activity of p300 and/or CBP and is used to treat cancer, particularly prostate cancer.

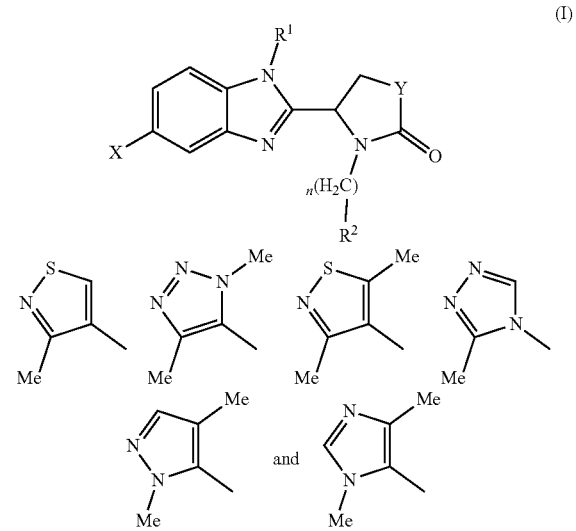

8 Claims, No Drawings

(56) References Cited

OTHER PUBLICATIONS

Ogiwara et al., "Targeting p300 Addiction in CBP-Deficient Cancers Causes Synthetic Lethality by Apoptotic Cell Death due to Abrogation of MYC Expression", Cancer Discovery, Apr. 2016, vol. 6, No. 4, 430-445.
Casey et al., "MYC regulates the antitumor immune response through CD47 and PD-L1", Science, Mar. 10, 2016, vol. 352, 15 pages.
Debes et al., "p300 in Prostate Cancer Proliferation and Progression", Cancer Research, Nov. 15, 2003, vol. 63, pp. 7638-7640.
Linja et al., "Expression of Androgen Receptor Coregulators in Prostate Cancer", Clinical Cancer Research, Feb. 1, 2004, vol. 10, 1032-1040.

\* cited by examiner

PHARMACEUTICAL COMPOUNDS

CROSS-REFERENCE TO RELATED APPLICATIONS

This application is a U.S. National Stage application of PCT/GB2017/053153 filed 18 Oct. 2017, which claims priority to Great Britain Application No. 1617627.3 filed 18 Oct. 2016, the entire disclosures of which are hereby incorporated by reference in their entireties.

FIELD OF THE INVENTION

The present invention relates to a series of novel benzimidazoles and to their use as modulators of p300 and/or CBP activity.

BACKGROUND TO THE INVENTION

Genetic and epigenetic modifications are critical to all stages of cancer disease progression and epigenetic silencing has been shown to be important in the misregulation of genes involved in all of the hallmarks of cancer (Jones, P. A. and Baylin, S. B. (2007) "The epigenomics of cancer", Cell, Vol. 128, pp. 683-692). The underlying epigenetic modifications that mediate regulation include DNA methylation and post translational histone modification. The latter includes methylation, acetylation, and ubiquitination. DNA-demethylating agents and histone deacetylase inhibitors have shown anti-tumour activity and a number of agents have been approved for use in the treatment of haematological malignancies. The enzymes mediating histone modification, including histone acetyltransferases (HATs) which acetylate histone and non-histone proteins, represent a wave of second generation targets for small molecule drug intervention.

Prostate cancer is one of the most common malignancies, and the second leading cause of cancer mortality among men. The treatment for clinically localised disease is typically surgery or radiation therapy. For patients who recur systemically after definitive treatment, or who present with loco-regional or metastatic disease, long term disease control is the primary objective. Typically, this entails a series of hormonal therapies that suppress androgen receptor (AR) signalling, since prostate cancers are exquisitely dependent upon AR function for survival and progression. Although AR targeted therapies inhibit tumour growth, disease is rarely eliminated and resistance to therapy is acquired through restored AR function. Progression to this 'castration resistant' prostate cancer (CRPC) represents the lethal phenotype of the illness. It is estimated that between 50-60% of patients that develop metastatic disease have CRPC. Recently, several new therapeutic agents have been approved for the treatment of CRPC. These however, provide limited clinical efficacy and serve only to prolong progression. Novel and tolerable agents are therefore necessary to make further gains in the treatment of CRPC.

Multiple cellular mechanisms lead to the progression of CRPC. In all cases, acquisition of the CRPC phenotype is mediated via re-activation of the AR pathway. The acetyltransferase p300 directly regulates AR levels and AR signalling activity in prostate cancer cells (Zhong et al., 'p300 acetyltransferase regulates androgen-receptor degradation and PTEN-deficient prostate tumorigenesis,' Cancer Res., Vol. 74, pp. 1870-1880, 2014). Therapeutic modulation of p300 activity would therefore target all known adaptive mechanisms which lead to the development of CRPC. Approved therapies and those in clinical studies primarily target only one or other of theses cellular mechanisms. The modulation of p300 activity directly provides an opportunity to more broadly modulate AR activity in CRPC than current and other experimental therapeutic strategies. In addition, resistance mechanisms to recently approved agents have been shown to be AR-dependent (Cai, C. et al., (2011) 'Intratumoral de novo steroid synthesis activates androgen receptor in castration-resistant prostate cancer and is up-regulated by treatment with Cyp17A1 inhibitors,' Cancer Res., Vol. 71, pp. 6503-6513). Modulation of p300 should therefore inhibit resistance to current therapies and potentially provide improved and sustained efficacy and greater clinical utility.

In common with p300, the CREB (cyclic-AMP response element binding protein) binding protein (CBP) is an acetyltransferase that acts as a transcriptional co-activator in human cells. Both CBP and p300 possess a single bromodomain (BRD) and a lysine acetyltransferase (KAT) domain, which are involved in the post-translational modification and recruitment of histones and non-histone proteins. There is high sequence similarity between CBP and p300 in the conserved functional domains (see Duncan A. Hay et al, JACS 2014, 135, 9308-9319). Modulation of CBP activity therefore provides a promising route to the treatment of certain cancers. Accordingly, compounds that can modulate, e.g. inhibit, the activity of p300 and/or CBP are of interest in cancer therapy.

Tumours which harbour loss of function mutations in CBP become addicted to p300 and are uniquely sensitive to p300 inhibition (see Ogiwara et al. 2016 Cancer Discovery. 6; 430-445). Conversely tumours with mutations in p300 are uniquely sensitive to CBP inhibition. Genetic analysis reveals that up to 15% of both non-small cell and small cell lung tumours have these loss of function mutations. Similar mutations are also found in up to 25% of bladder cancers. Accordingly, compounds that can modulate, eg inhibit, the activity of p300 and/or CBP are of interest in cancer therapy for tumours with these molecular changes.

Furthermore, CBP/p300 regulates the expression of key tumour immune checkpoint proteins such as CTLA4/PD-L1 (see Casey et al., Science. 352; p22'7-231, 2016) and plays an important role in the differentiation and function of T-regulatory cells which are involved in immune evasion by tumours. Accordingly, compounds that can modulate, eg inhibit, the activity of p300 and/or CBP are of interest for cancer therapy in combination with agents that target the onco-immune system.

SUMMARY OF THE INVENTION

It has now been found that a series of novel compounds have activity in modulating p300 and/or CBP activity. The compounds therefore have potential utility in treating cancer, particularly prostate cancer.

Accordingly, the present invention provides a compound which is a benzimidazole of formula (I):

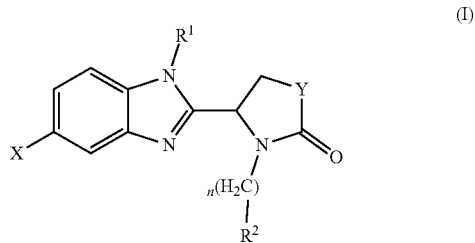

wherein:

X is a 5-membered heteroaryl group selected from the following:

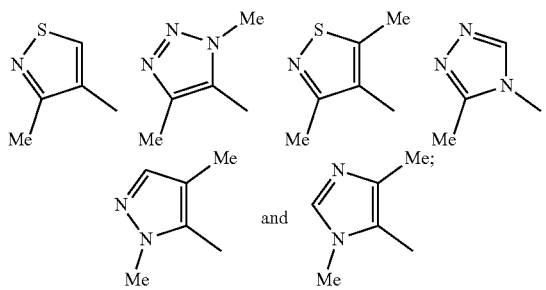

$R^1$ is a group which is unsubstituted or substituted and is selected from C-linked 4- to 6-membered heterocyclyl; $C_3$-$C_6$ cycloalkyl; $C_1$-$C_6$ alkyl which is unsubstituted or substituted by $C_6$-$C_{10}$ aryl, 5- to 12-membered N-containing heteroaryl, $C_3$-$C_6$ cycloalkyl, OH, —OC(O)R' or OR' wherein R' is unsubstituted $C_1$-$C_6$ alkyl; and a spiro group of the following formula:

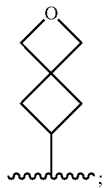

Y is —CH$_2$—, —CH$_2$CH$_2$— or —CH$_2$CH$_2$CH$_2$—;
n is 0 or 1; and
$R^2$ is a group selected from $C_6$-$C_{10}$ aryl, 5- to 12-membered N-containing heteroaryl, $C_3$-$C_6$ cycloalkyl and $C_5$-$C_6$ cycloalkenyl, wherein the group is unsubstituted or substituted and wherein $C_6$-$C_{10}$ aryl is optionally fused to a 5- or 6-membered heterocyclic ring;
or a pharmaceutically acceptable salt thereof.

In another aspect the invention provides a pharmaceutical composition comprising a benzimidazole of formula (I) as defined above or a pharmaceutically acceptable salt thereof and a pharmaceutically acceptable carrier. The pharmaceutical composition may further comprise one or more additional chemotherapeutic agents, for instance as mentioned below.

In a further aspect the invention provides a benzimidazole of formula (I) as defined above, or a pharmaceutically acceptable salt thereof, for use as a modulator of p300 and/or CBP activity.

DETAILED DESCRIPTION OF THE INVENTION

The term "substituted" includes the implicit provision that substitution be in accordance with the permitted valence of the substituted atom and the substituent and that the substitution results in a stable compound (i.e. one that does not spontaneously undergo transformation such as a rearrangement cyclisation, or elimination). In certain embodiments, a single atom may be substituted with more than one substituent as long as such substitution is in accordance with the permitted valence of the atom. In certain embodiments, a group that is substituted may be substituted by one substituent group or it may be multiply substituted on multiple carbon atoms. When any group defined herein is substituted, it is typically substituted by $R^{10}$ as defined below. The group may, for instance, be mono-, di- or tri-substituted by a group $R^{10}$ as defined below.

In certain of the benzimidazoles of formula (I), dependant on the nature of the substituent, there may be chiral carbon atoms and therefore the compounds may exist as stereoisomers. The invention extends to all optical isomers such as stereoisomeric forms of the compounds of formula (I), including enantiomers, diastereomers and mixtures thereof, such as racemates. The different stereoisomeric forms may be separated or resolved one from the other by conventional methods or any given isomer may be obtained by conventional stereoselective or stereospecific syntheses.

The compounds of the invention can exist in various tautomeric forms and it is to be understood that the invention encompasses all such tautomeric forms.

It is understood that certain compounds of the invention contain both acidic and basic groups and may therefore exist as zwitterions at certain pH values.

It is also to be understood that any atom present in a compound of the invention may be present in any available naturally-occurring isotopic form. For instance, a carbon atom may be $^{12}$C or $^{13}$C. A hydrogen atom may be $^1$H or $^2$H (deuterium).

As used herein, the terms "treat" and "treatment" refer to both therapeutic treatment and prophylactic or preventative measures, wherein the object is to prevent or slow down (lessen) an undesired physiological change or disorder, such as the development or spread of cancer. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "pharmaceutically acceptable" indicates that the substance or composition must be compatible chemically and/or toxicologically with the other ingredients comprising a formulation, and/or the patient being treated therewith.

A $C_{1-6}$ alkyl group or moiety is linear or branched. A $C_{1-6}$ alkyl group is typically a $C_{1-4}$ alkyl group, or a $C_{1-2}$ alkyl group. Examples of $C_{1-6}$ alkyl groups and moieties include methyl, ethyl, n-propyl, i-propyl, n-butyl, i-butyl, t-butyl, n-pentyl, pentyl (i.e. 3-methylbut-1-yl), t-pentyl (i.e. 2-methylbut-2-yl), neopentyl (i.e. 2,2-dimethylpropan-1-yl), n-hexyl, i-hexyl (i.e. 4-methylpentan-1-yl), t-hexyl (i.e. 3-methylpentan-3-yl) and neopentyl (i.e. 3,3-dimethylbutan-1-yl). Typically a $C_{1-6}$ alkyl group is methyl (Me). For the avoidance of doubt, where two alkyl moieties are present in a group, the alkyl moieties may be the same or different. A $C_{1-6}$ alkyl group is unsubstituted or substituted, typically by one or more groups $R^{10}$ as defined below. For example, a $C_{1-6}$ alkyl group is unsubstituted or substituted by 1, 2 or 3 groups $R^{10}$ as defined below.

A $C_{1-6}$ alkylene group or moiety is an unsubstituted or substituted, linear or branched, saturated divalent aliphatic hydrocarbon group or moiety containing 1 to 6 carbon atoms. Typically it is a $C_{1-3}$ alkylene group or moiety. Examples include methylene, ethylene, n-propylene and i-propylene groups and moieties. More typically it is methylene or ethylene. When the alkylene group is substituted it is typically substituted by a group $R^{10}$ as defined below.

A $C_{3-6}$ cycloalkyl group or moiety is a saturated monovalent hydrocarbon ring having 3 to 6 carbon atoms. It is thus a 3-, 4-, 5- or 6-membered carbocyclic ring containing only saturated bonds. Examples of a cycloalkyl group include cyclopropyl, cyclobutyl, cyclopentyl and cyclohexyl. In one embodiment a cycloalkyl group is cyclopropyl.

A 5- to 12-membered N-containing heteroaryl group or moiety is a monovalent 5- to 12-membered aromatic heterocyclic group which contains 1, 2, 3, or 4 nitrogen atoms, typically 1 or 2 N atoms, and 0, 1 or 2 other heteroatoms selected from O and S. It is linked via one of its ring N atoms or C atoms and is monocyclic or bicyclic. In one embodiment it is N-linked. In another embodiment it is C-linked. It may be, for example, a 5- to 7-membered N-containing monocyclic heteroaryl group, for instance a 5- or 6-membered N-containing heteroaryl group such as pyrrolyl, imidazolyl, pyridyl, pyrimidinyl, pyrazinyl, thiazolyl, isothiazolyl, oxazolyl or isoxazolyl.

Examples of a 5- to 12-membered, N-containing heteroaryl group include pyrrolyl, imidazolyl, pyridyl, pyrazinyl, pyrimidinyl, thiazolyl, isothiazolyl, oxazolyl, isoxazolyl, quinolyl, isoquinolyl, quinazolinyl, quinoxalinyl, indolyl, isoindolyl, indazolyl, pyrrolopyridinyl and pyrrolopyrimidinyl groups. When substituted, a 5- to 12-membered, N-containing heteroaryl group is typically substituted by one or more, e.g. 1, 2 or 3, groups selected from unsubstituted $C_{1-4}$ alkyl and a group $R^{10}$ as defined below In one embodiment a 5- to 12-membered, N-containing heteroaryl group is unsubstituted.

A 4- to 6-membered C-linked heterocyclic group in the definition is a saturated monovalent 4-, 5- or 6-membered heterocyclic ring containing at least one heteroatom selected from O, N and S. It is linked via one of its ring C atoms. Examples include oxetane, thietane, azetidine, pyrrolidine, piperidine, tetrahydropyran, tetrahydrothiopyran and tetrahydrofuran. A 4- to 6-membered C-linked, heterocyclic group is unsubstituted or substituted, typically by a group $R^{10}$ as defined below. It may be substituted on a ring carbon atom or on a ring N or S atom, as permitted by the valency of the atom.

A halogen or halo group is F, Cl, Br or I. Typically it is F, Cl or Br, more typically F.

A $C_{1-6}$ alkoxy group is linear or branched. It is typically a $C_{1-4}$ alkoxy group, for example a methoxy, ethoxy, propoxy, i-propoxy, n-propoxy, n-butoxy, sec-butoxy or tert-butoxy group. A $C_{1-6}$ alkoxy group is unsubstituted or substituted, typically by one or more groups $R^{10}$ as defined below.

Moiety X in formula (I) is selected from six specific methyl-substituted 5-membered heteroaryl groups. Based on computer modelling, these particular groups occupy a similar spatial orientation to the 3,5-dimethylisoxazol-4-yl group that occupies the corresponding position in the benzimidazole compounds described by Duncan A. Hay et al in JACS 2014, 135, 9308-9319 (also quoted above).

In one embodiment of formula (I), X is the 1,4-dimethyl-1H-1,2,3-triazol-5-yl group of the following structure:

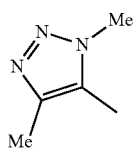

When in formula (I) $R^1$ is substituted, the substituents are typically 1, 2 or 3 groups, more typically 1 or 2 groups, which are the same or different and are selected from —SO$_2$Me, —SO$_2$-cyclopropyl, oxo (=O), $C_1$-$C_6$ alkoxy, OH, hydroxy($C_1$-$C_6$)alkyl, halo, —NH$_2$, OH, CN, —OC(O)R″, —C(O)NHR″, —NHC(O)R″ and —COOR″, where R″ is H or $C_1$-$C_6$ alkyl optionally substituted by halo. In this context halo is typically F or Cl.

The 4- to 6-membered heterocyclyl is typically pyrrolidinyl, piperidinyl, tetrahydropyranyl or tetrahydrothiopyranyl. More typically it is pyrrolidin-3-yl, piperidin-4-yl, tetrahydropyran-4-yl or tetrahydrothiopyran-4-yl. Pyrrolidinyl and piperidinyl are typically substituted on the ring N atom by —SO$_2$Me or $C_1$-$C_6$ alkyl (e.g. methyl). Tetrahydropyranyl is typically substituted on a ring C atom by $C_1$-$C_6$ alkyl (e.g. methyl). Tetrahydrothiopyranyl is typically di-substituted on the ring S atom by oxo.

The $C_3$-$C_6$ cycloalkyl group is typically cyclobutyl, cyclopropyl or cyclohexyl, for instance cyclohexyl. Cycloalkyl, for instance cyclohexyl, is typically substituted by 1 or 2 groups selected from halo, OH, —OC(O)R″ (for instance —OC(O)Me) and $C_1$-$C_6$ alkoxy. Halo is typically F.

In the definition of $R^1$, $C_1$-$C_6$ alkyl substituted by 5- to 12-membered N-containing heteroaryl is typically $C_1$-$C_6$ alkyl, for instance methyl or ethyl, substituted by a 5- or 6-membered N-containing heteroaryl as defined above.

Typical examples of $R^1$ in formula (I) as defined above include the following groupings:

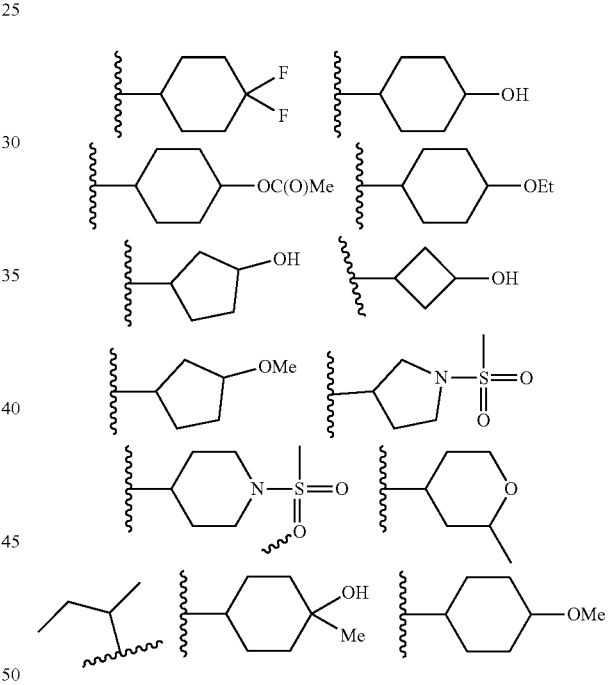

The integer n in formula (I) as defined above is 0 or 1, typically 0.

Y is typically —CH$_2$— or —CH$_2$CH$_2$— such that the ring containing it is a 5- or 6-membered ring. When Y is —CH$_2$— the ring is pyrrolidin-2-one. When Y is —CH$_2$CH$_2$— the ring is piperidin-2-one. More typically Y is —CH$_2$— and the ring containing it is the 5-membered pyrrolidin-2-one ring.

$R^2$ is typically aromatic. It is therefore typically a $C_6$-$C_{10}$ aryl or a 5- to 12-membered N-containing heteroaryl group (such as a 5- or 6-membered N-containing heteroaryl group) wherein $C_6$-$C_{10}$ aryl is optionally fused to a 5- or 6-membered heterocyclic ring. The $C_6$-$C_{10}$ aryl group is typically phenyl or naphthyl. A $C_6$-$C_{10}$ aryl group fused to a 5- or 6-membered heterocyclic ring is typically a tetrahydrobenzofuranyl group.

When $R^2$ is a $C_6$-$C_{10}$ aryl group, for instance phenyl, it is typically mono-, di- or tri-substituted. The substituents are 1, 2 or 3 groups which are the same or different and are typically selected from $C_1$-$C_6$ alkyl, $C_1$-$C_6$ alkoxy, OH, cyano and halo, wherein the alkyl and alkoxy groups are each optionally substituted by halo. Halo in this context is typically F or Cl, more typically F.

When the $C_6$-$C_{10}$ aryl group is phenyl, it is typically substituted by 1, 2 or 3 groups, more typically 1 or 2 groups. The 1 or 2 groups are typically positioned meta and/or para on the phenyl ring. The groups are typically selected from halo, OH, $C_1$-$C_6$ alkyl, $C_1$-$C_6$ alkoxy and CN.

$R^{10}$ is selected from unsubstituted $C_{1-6}$ alkyl, $C_{3-6}$ cycloalkyl, halo, OH, $C_{1-6}$ alkoxy, —C(O)R''', —C(O)$_2$R''', —C(O)NR'''$_2$, oxo (=O), dioxo, —CH$_2$OR''', —S(O)$_m$R''', —NR'''C(O)R''', —S(O)$_m$NR'''$_2$, and CF$_3$, wherein m is 1 or 2 and each R' is independently selected from H and unsubstituted $C_{1-6}$ alkyl. Typically $R^{10}$ is selected from unsubstituted $C_{1-6}$ alkyl, halo, OH, $C_{1-6}$ alkoxy, —C(O)R''', —C(O)NR'''$_2$, —NR'''C(O)R''', oxo (=O) and dioxo.

In one preferred embodiment, the benzimidazole of the invention has the following formula (Ia):

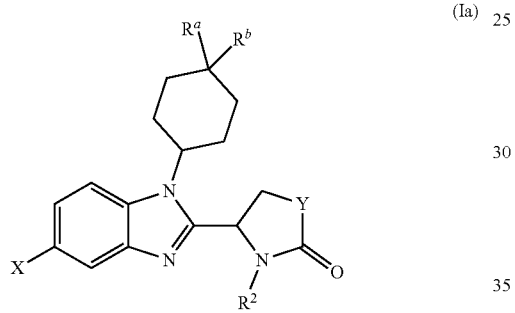

(Ia)

wherein
X, Y and $R^2$ are as defined above for formula (I); and
each of $R^a$ and $R^b$ is independently selected from H, halo, OH, —OC(O)R'', —SO$_2$Me, —SO$_2$-cyclopropyl, oxo (=O), $C_1$-$C_6$ alkoxy, hydroxy($C_1$-$C_6$)alkyl, —NH$_2$, CN, —C(O)NHR'', —NHC(O)R'' and —COOR'', where R'' is H or $C_1$-$C_6$ alkyl optionally substituted by halo.

Typically in formula (Ia), at least one of $R^a$ and $R^b$ is other than H.

In one embodiment, one of $R^a$ and $R^b$ is selected from halo, OH and —OC(O)R'', for instance —OC(O)Me. The other of $R^a$ and $R^b$ is typically H. In another embodiment each of $R^a$ and $R^b$ is halo. In these embodiments halo is typically F.

Typically in formula (Ia), Y is —CH$_2$—.

$R^2$ in formula (Ia) is typically $C_6$-$C_{10}$ aryl which is unsubstituted or mono-, di- or tri-substituted by one or more groups $R^{10}$ as defined above, which groups are the same or different when more than one is present.

Compounds of the invention may contain asymmetric or chiral centres and thus exist in different stereoisomeric forms. The structural formulae (I) and (Ia) above encompass all stereoisomeric forms of the compounds of the invention including diastereomers, enantiomers and racemic mixtures. Diastereomers and enantiomers may be obtained by stereoselective synthetic strategies, for instance via enantiomeric synthesis.

Stereoisomerism may occur in compounds of the present invention due to the presence of an asymmetric carbon atom in the piperidin-2-one or pyrrolidin-2-one ring. Thus, as depicted in the structural formula below:

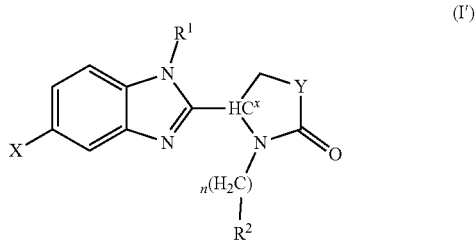

(I')

the carbon centre $C^x$ is chiral and each of X, $R^1$, Y, $R^2$ and n is as defined above for formula (I). The chirality at $C^x$ means that a compound of the invention can be racemic or optically pure. When optically pure it may be the R enantiomer or the S enantiomer, typically the S enantiomer.

Specific examples of compounds of the invention include those listed in the following table:

| No | Structure | Name |
|----|-----------|------|
| 1 | ![structure] | (1S,4r)-4-(2-((S)-1-(3,4-difluorophenyl)-5-oxopyrrolidin-2-yl)-5-(1,4-dimethyl-1H-1,2,3-triazol-5-yl)-1H-benzo[d]imidazol-1-yl)cyclohexyl acetate |

-continued

| No | Structure | Name |
|---|---|---|
| 2 | 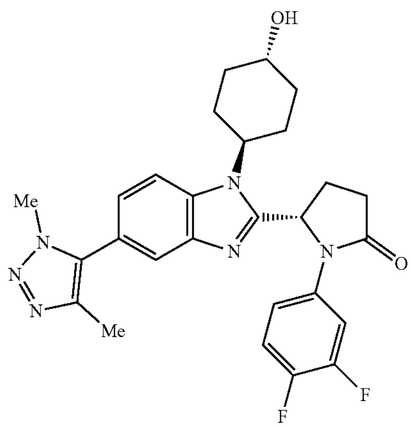 [SMILES: Cc1nnn(C)c1-c1ccc2c(c1)nc([C@@H]1CCC(=O)N1c1ccc(F)c(F)c1)n2[C@H]1CC[C@H](O)CC1] | (S)-1-(3,4-difluorophenyl)-5-(5-(1,4-dimethyl-1H-1,2,3-triazol-5-yl)-1-((1r,4S)-4-hydroxycyclohexyl)-1H-benzo[d]imidazol-2-yl)pyrrolidin-2-one |
| 3 | 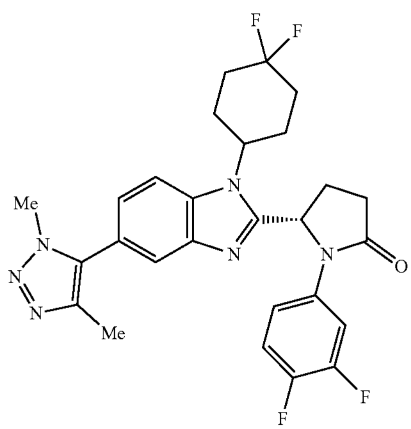 [SMILES: Cc1nnn(C)c1-c1ccc2c(c1)nc([C@@H]1CCC(=O)N1c1ccc(F)c(F)c1)n2C1CCC(F)(F)CC1] | (S)-5-(1-(4,4-difluorocyclohexyl)-5-(1,4-dimethyl-1H-1,2,3-triazol-5-yl)-1H-benzo[d]imidazol-2-yl)-1-(3,4-difluorophenyl)pyrrolidin-2-one |
| 4 | 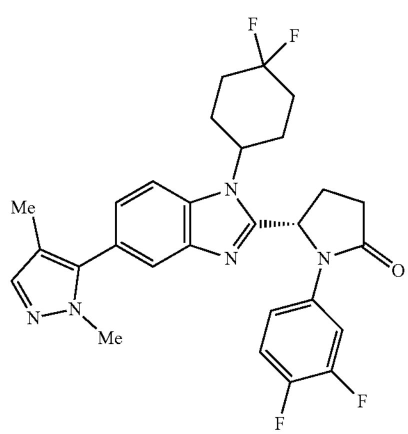 [SMILES: Cc1cnn(C)c1-c1ccc2c(c1)nc([C@@H]1CCC(=O)N1c1ccc(F)c(F)c1)n2C1CCC(F)(F)CC1] | (S)-5-(1-(4,4-difluorocyclohexyl)-5-(1,4-dimethyl-1H-pyrazol-5-yl)-1H-benzo[d]imidazol-2-yl)-1-(3,4-difluorophenyl)pyrrolidin-2-one |

-continued
| No | Structure | Name |
|---|---|---|
| 5 | 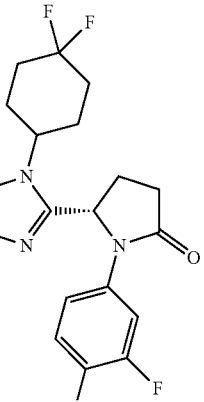 | (S)-5-(1-(4,4-difluorocyclohexyl)-5-(1,4-dimethyl-1H-imidazol-5-yl)-1H-benzo[d]imidazol-2-yl)-1-(3,4-difluorophenyl)pyrrolidin-2-one |
| 7 | 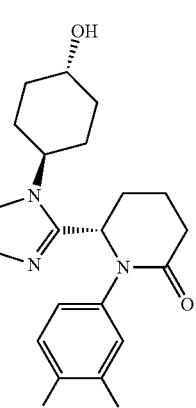 | (S)-1-(3-chloro-4-fluorophenyl)-6-(5-(1,4-dimethyl-1H-1,2,3-triazol-5-yl)-1-((trans)-4-hydroxycyclohexyl)-1H-benzo[d]imidazol-2-yl)piperidin-2-one |
| 8 | 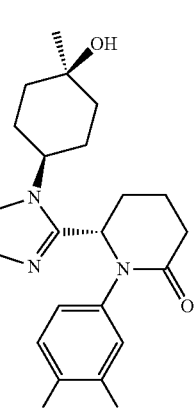 | (S)-1-(3,4-difluorophenyl)-6-(5-(1,4-dimethyl-1H-1,2,3-triazol-5-yl)-1-(cis-4-hydroxy-4-methylcyclohexyl)-1H-benzo[d]imidazol-2-yl)piperidin-2-one |

-continued

| No | Structure | Name |
|----|-----------|------|
| 9  | 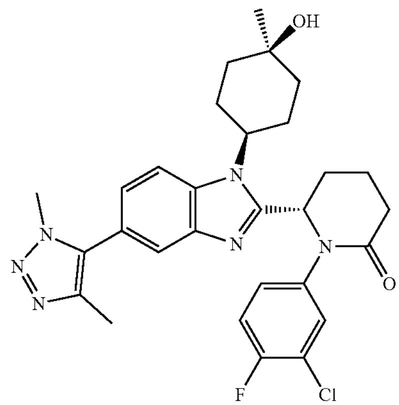 [SMILES: Cc1nnn(C)c1-c1ccc2c(c1)nc([C@@H]1CCCC(=O)N1c1ccc(F)c(Cl)c1)n2[C@H]1CC[C@@](C)(O)CC1]          | (S)-1-(3-chloro-4-fluorophenyl)-6-(5-(1,4-dimethyl-1H-1,2,3-triazol-5-yl)-1-(cis-4-hydroxy-4-methylcyclohexyl)-1H-benzo[d]imidazol-2-yl)piperidin-2-one |
| 10 | 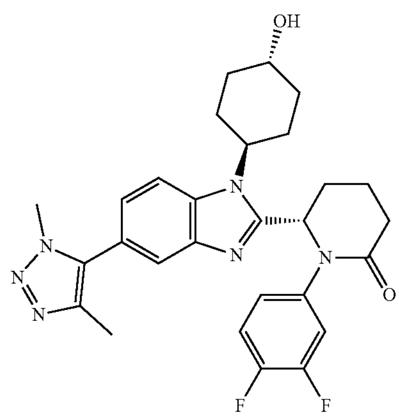 [SMILES: Cc1nnn(C)c1-c1ccc2c(c1)nc([C@@H]1CCCC(=O)N1c1ccc(F)c(F)c1)n2[C@H]1CC[C@H](O)CC1]          | (S)-1-(3,4-difluorophenyl)-6-(5-(1,4-dimethyl-1H-1,2,3-triazol-5-yl)-1-(trans-4-hydroxycyclohexyl)-1H-benzo[d]imidazol-2-yl)piperidin-2-one |
| 11 | 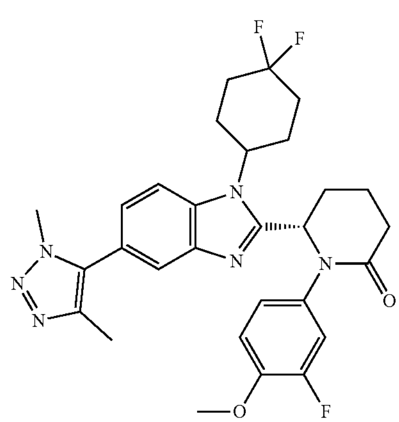 [SMILES: COc1ccc(N2C(=O)CCC[C@H]2c2nc3cc(-c4c(C)nnn4C)ccc3n2C2CCC(F)(F)CC2)cc1F]          | (S)-6-(1-(4,4-difluorocyclohexyl)-5-(1,4-dimethyl-1H-1,2,3-triazol-5-yl)-1H-benzo[d]imidazol-2-yl)-1-(3-fluoro-4-methoxyphenyl)piperidin-2-one |

-continued

| No | Structure | Name |
|---|---|---|
| 12 | 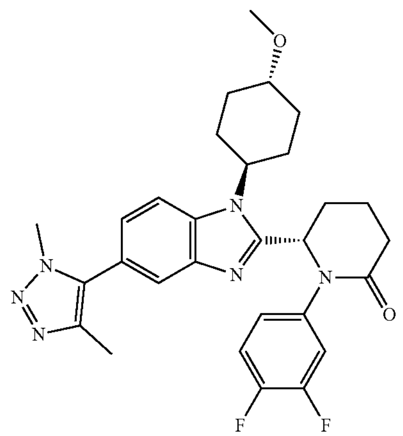 [SMILES: CO[C@H]1CC[C@H](n2c([C@@H]3CCCC(=O)N3c3ccc(F)c(F)c3)nc3cc(-c4c(C)nnn4C)ccc32)CC1] | (S)-1-(3,4-difluorophenyl)-6-(5-(1,4-dimethyl-1H-1,2,3-triazol-5-yl)-1-(trans-4-methoxycyclohexyl)-1H-benzo[d]imidazol-2-yl)piperidin-2-one |
| 13 | 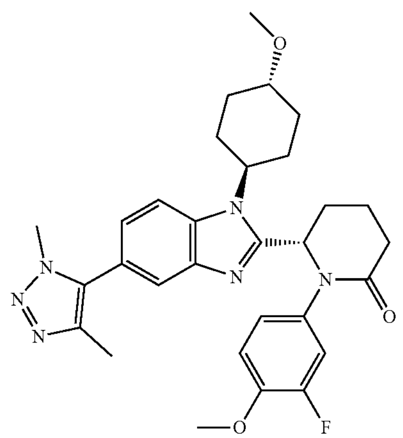 [SMILES: COc1ccc(N2C(=O)CCC[C@H]2c2nc3cc(-c4c(C)nnn4C)ccc3n2[C@H]2CC[C@H](OC)CC2)cc1F] | (S)-6-(5-(1,4-dimethyl-1H-1,2,3-triazol-5-yl)-1-(trans-4-methoxycyclohexyl)-1H-benzo[d]imidazol-2-yl)-1-(3-fluoro-4-methoxyphenyl)piperidin-2-one |
| 14 | 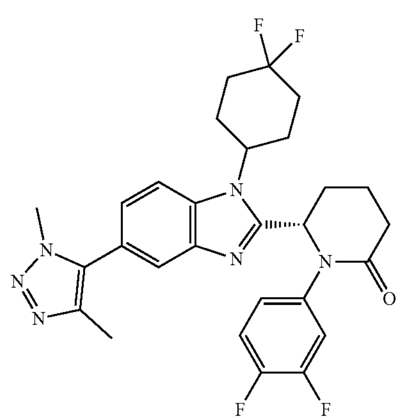 [SMILES: Cc1nnn(C)c1-c1ccc2c(c1)nc([C@@H]1CCCC(=O)N1c1ccc(F)c(F)c1)n2C1CCC(F)(F)CC1] | (S)-6-(1-(4,4-difluorocyclohexyl)-5-(1,4-dimethyl-1H-1,2,3-triazol-5-yl)-1H-benzo[d]imidazol-2-yl)-1-(3,4-difluorophenyl)piperidin-2-one |

-continued

| No | Structure | Name |
|----|-----------|------|
| 15 | 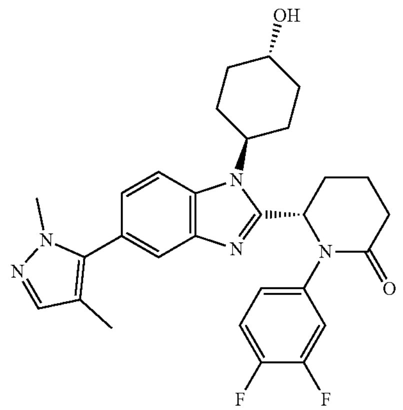 [SMILES: Cc1cnn(C)c1-c1ccc2c(c1)nc([C@@H]1CCCC(=O)N1c1ccc(F)c(F)c1)n2[C@H]1CC[C@H](O)CC1] | (S)-1-(3,4-difluorophenyl)-6-(5-(1,4-dimethyl-1H-pyrazol-5-yl)-1-(trans-4-hydroxycyclohexyl)-1H-benzo[d]imidazol-2-yl)piperidin-2-one |
| 16 | 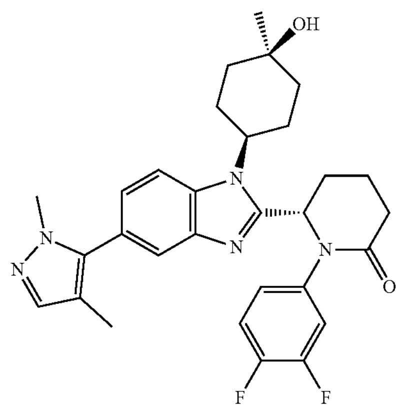 [SMILES: Cc1cnn(C)c1-c1ccc2c(c1)nc([C@@H]1CCCC(=O)N1c1ccc(F)c(F)c1)n2[C@H]1CC[C@@](C)(O)CC1] | (S)-1-(3,4-difluorophenyl)-6-(5-(1,4-dimethyl-1H-pyrazol-5-yl)-1-(cis-4-hydroxy-4-methylcyclohexyl)-1H-benzo[d]imidazol-2-yl)piperidin-2-one |
| 17 | 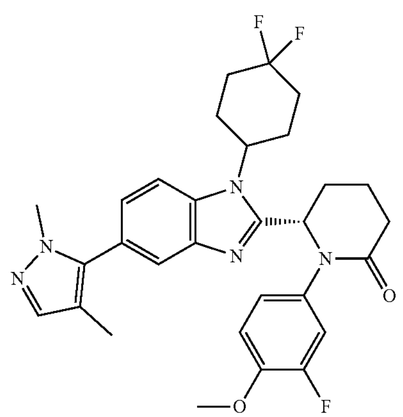 [SMILES: COc1ccc(N2C(=O)CCC[C@H]2c2nc3cc(-c4c(C)cnn4C)ccc3n2C2CCC(F)(F)CC2)cc1F] | (S)-6-(1-(4,4-difluorocyclohexyl)-5-(1,4-dimethyl-1H-pyrazol-5-yl)-1H-benzo[d]imidazol-2-yl)-1-(3-fluoro-4-methoxyphenyl)piperidin-2-one |

-continued

| No | Structure | Name |
|---|---|---|
| 18 | 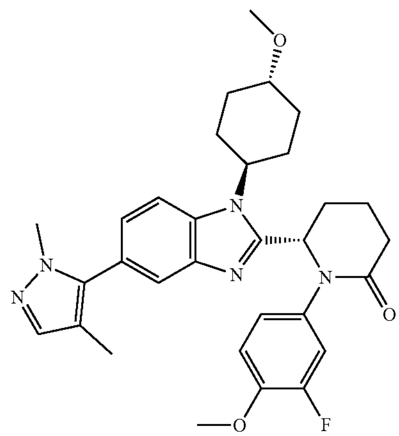 [SMILES: COc1ccc(N2C(=O)CCC[C@H]2c2nc3cc(-c4c(C)cnn4C)ccc3n2[C@H]2CC[C@H](OC)CC2)cc1F] | (S)-6-(5-(1,4-dimethyl-1H-pyrazol-5-yl)-1-(trans-4-methoxycyclohexyl)-1H-benzo[d]imidazol-2-yl)-1-(3-fluoro-4-methoxyphenyl)piperidin-2-one |
| 19 | 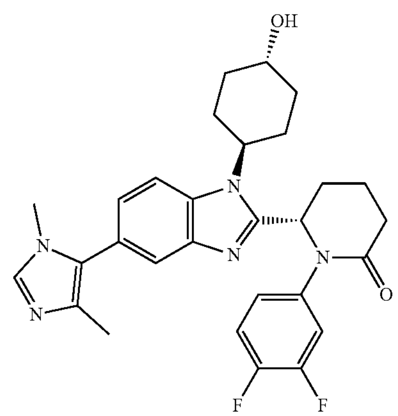 [SMILES: Cc1ncn(C)c1-c1ccc2c(c1)nc([C@@H]1CCCC(=O)N1c1ccc(F)c(F)c1)n2[C@H]1CC[C@H](O)CC1] | (S)-1-(3,4-difluorophenyl)-6-(5-(1,4-dimethyl-1H-imidazol-5-yl)-1-(trans-4-hydroxycyclohexyl)-1H-benzo[d]imidazol-2-yl)piperidin-2-one |
| 20 | 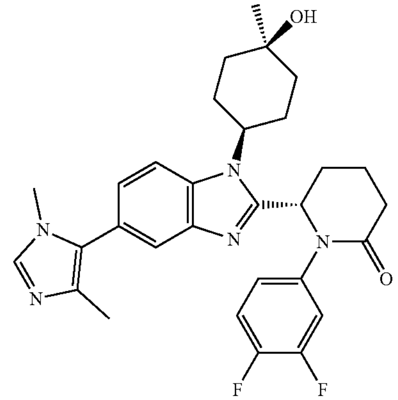 [SMILES: Cc1ncn(C)c1-c1ccc2c(c1)nc([C@@H]1CCCC(=O)N1c1ccc(F)c(F)c1)n2[C@H]1CC[C@@](C)(O)CC1] | (S)-1-(3,4-difluorophenyl)-6-(5-(1,4-dimethyl-1H-imidazol-5-yl)-1-(cis-4-hydroxy-4-methylcyclohexyl)-1H-benzo[d]imidazol-2-yl)piperidin-2-one |

| No | Structure | Name |
|---|---|---|
| 21 | 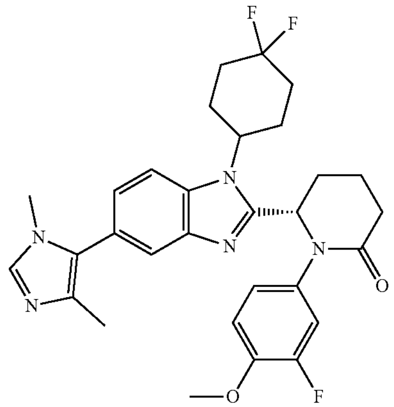 [SMILES: COc1ccc(N2C(=O)CCC[C@H]2c2nc3cc(-c4c(C)ncn4C)ccc3n2C2CCC(F)(F)CC2)cc1F] | (S)-6-(1-(4,4-difluorocyclohexyl)-5-(1,4-dimethyl-1H-imidazol-5-yl)-1H-benzo[d]imidazol-2-yl)-1-(3-fluoro-4-methoxyphenyl)piperidin-2-one |
| 22 | | (S)-6-(5-(1,4-dimethyl-1H-imidazol-5-yl)-1-(trans-4-methoxycyclohexyl)-1H-benzo[d]imidazol-2-yl)-1-(3-fluoro-4-methoxyphenyl)piperidin-2-one | and the pharmaceutically acceptable salts thereof.

A compound of the invention may be prepared by a process which comprises the Pd-catalysed cross-coupling of a compound of formula (II):

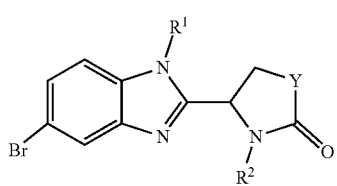

(II)

wherein each of $R^1$, Y and $R^2$ is as defined above for formula (I), with a boronic acid of formula X—B(OH)$_2$ wherein X is as defined above for formula (I); or the Pd-catalysed cross-coupling of a compound of formula (II'):

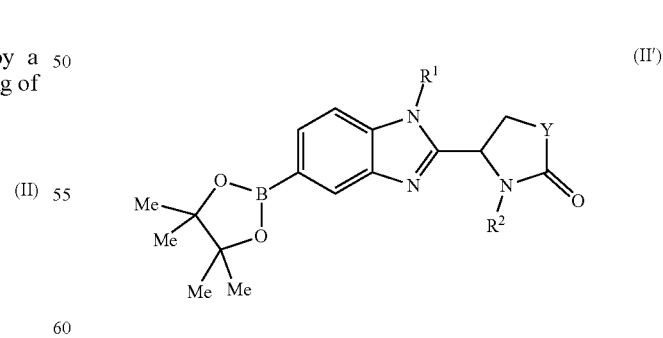

(II')

wherein each of $R^1$, Y and $R^2$ is as defined above for formula (I), with a compound of formula X—Br wherein X is as defined above for formula (I).

A compound of the invention may alternatively be prepared by a process which comprises treating a compound of formula (III)

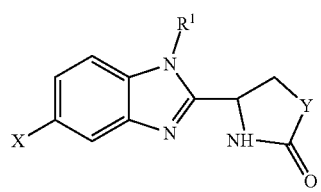

wherein each of X, R¹ and Y is as defined above for formula (I), with a compound of formula R²—CH₂Br in which R² is as defined above for formula (I). Typically the reaction is conducted by adding sodium hexamethyldisilazane (NaHMDS) in THF to a solution of the compound of formula (II) in DMF, and then adding a solution of the compound of formula R²—CH₂Br in DMF.

The schemes shown below illustrate synthetic strategies, including the above process steps, by which compounds of the invention may be produced.

General Route A: Non-Convergent Approach to γ-Lactam Analogues

A = C, CH, N, NH
n = 1, 2
a. R₁—NH₂, TEA, THF, rt or R₁—NH₂·HCl, TEA, DMF, 70-90° C.
b. Na₂S₂O₄, THF/H₂O, NH₄OH
c. For n = 1: HATU, pyroglutamic acid, TEA, DCM or DMF (either purified or used crude), RT or for n = 2: T3P, (S)-2-oxo-6-piperidinecarboxylic acid, TEA, DCM, RT
d. AcOH, 60-100° C.
e. Arylboronic acid, CuTMEDA, pyridine, 40° C. or arylboronic acid, Cu(OAc)₂, pyridine, DCM, RT
f. Pd-catalysed cross-coupling The route in which n=1 is shown separately below:

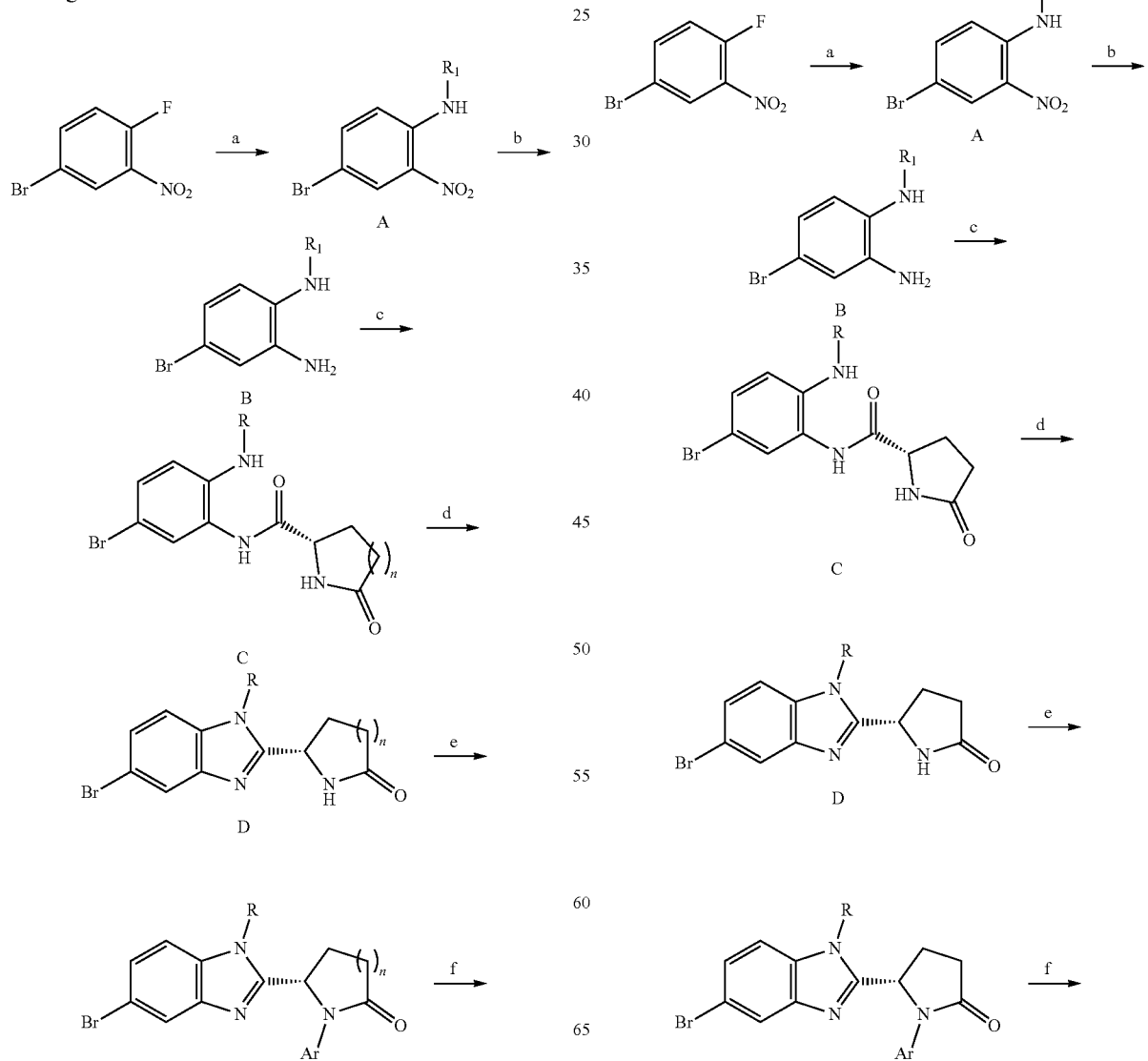

-continued

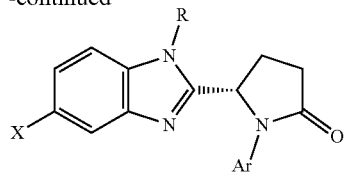

a. R₁—NH₂, TEA, THF, rt or R₁—NH₂·HCl, TEA, DMF, 70-90° C.
b. Na₂S₂O₄, THF/H₂O, NH₄OH
c. HATU, pyroglutamic acid, TEA, DCM or DMF (either purified or used crude)
d. AcOH, 60-100° C.
e. Arylboronic acid, CuTMEDA, pyridine, 40° C.
f. Pd-catalysed cross-coupling General Route B: Convergent Approach to γ-Lactam Analogues Using N-arylpyroglutamic Acids

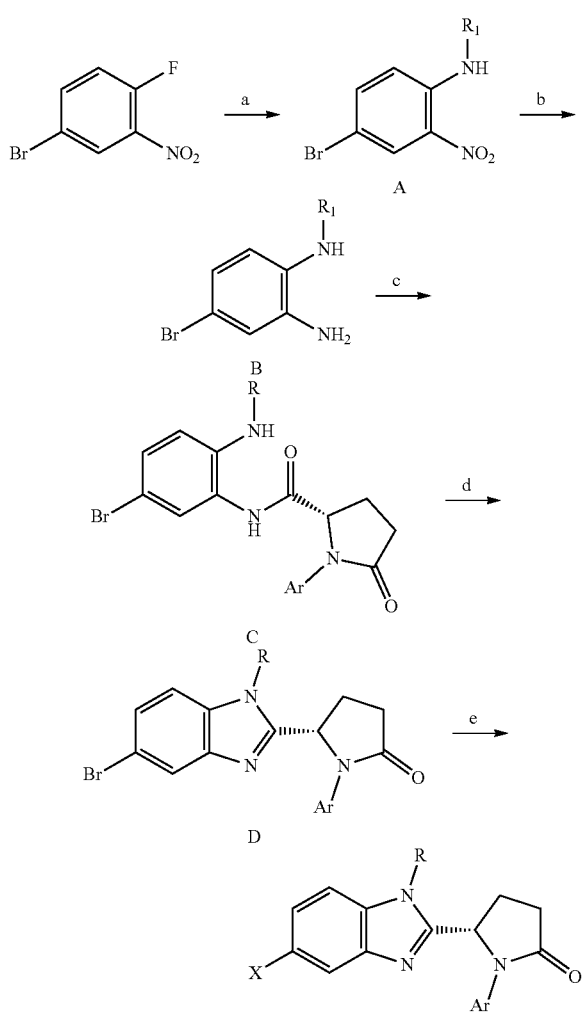

a. R₁—NH₂, TEA, THF, rt or R₁—NH₂·HCl, TEA, DMF, 70-90° C.
b. Na₂S₂O₄, THF/H₂O, NH₄OH
c. HATU, N-arylpyroglutamic acid, TEA, DCM or DMF (either purified or used crude)
d. AcOH, 60-100° C.
e. Pd-catalysed cross-coupling A key to the abbreviations used in all the above schemes is provided in the Examples section below.

A benzimidazole of formula (I) may be converted into a pharmaceutically acceptable salt, and salts may be converted into the free compound, by conventional methods. Pharmaceutically acceptable salts include salts of inorganic acids such as hydrochloric acid, hydrobromic acid and sulfuric acid, and salts of organic acids such as acetic acid, oxalic acid, malic acid, methanesulfonic acid, trifluoroacetic acid, benzoic acid, citric acid and tartaric acid. In the case of compounds bearing a free carboxy substituent, the salts include both the above-mentioned acid addition salts and the salts of sodium, potassium, calcium and ammonium. The latter are prepared by treating the free benzimidazole of formula (I), or an acid addition salt thereof, with the corresponding metal base or ammonia.

A benzimidazole of formula (I) or a pharmaceutically acceptable salt thereof is hereafter referred to as a compound of the invention. Compounds of the invention have been found in biological tests to bind to the histone acetyltransferase (HAT), p300, and to CBP, as described in Example 6 below.

CREB binding protein (CBP) and its paralogue, p300, are two closely-related histone acetyl transferase co-factor proteins that are involved in a wide variety of cancer processes, including cell proliferation, apoptosis, cell cycle regulation and DNA damage response. CBP/p300 primarily functions as a transcription cofactor for a number of oncoproteins including Jun, Fos and E2F. In addition, it acts as a histone acetyltransferase and can also acetylate multiple non-histone proteins such as p53, p73, and Rb. CBP/p300 has been reported to act as a tumour suppressor or as an oncoprotein dependent upon the nature of the cancer. Multiple studies have shown that p300 expression correlates with disease progression and decreased survival.

CBP and p300 is up-regulated in human prostate cancer progression and has been shown to be an AR co-activator (Debes, J. D., et al., (2003) 'p300 in prostate cancer proliferation and progression,' *Cancer Res.*, Vol. 63, pp. 7638-7640; and Linja, M. J. et al., (2004) 'Expression of androgen receptor coregulators in prostate cancer,' *Clin. Cancer Res.*, Vol. 10, pp. 1032-1040).

p300 has recently been shown to directly regulate AR protein degradation (Zhong et al., 2014). p300 mediated AR acetylation was shown to inhibit AR ubiquitination and subsequent AR proteasome degradation (Zhong et al., 2014, cited above). The direct inhibition of p300 activity would therefore promote AR degradation.

Given the high molecular heterogeneity of prostate cancer, the identification of appropriate biomarkers is critical to the effective positioning and evaluation of targeted small molecule therapies. It is proposed that markers of the development of the CRPC phenotype via AR resurgence are used for patient stratification for the evaluation of p300 modulators. These include PSA and circulating tumour cell (CTC) counts and the appearance of AR and AR splice variants in CTCs.

In terms of biomarkers to enable the monitoring of the modulation of p300 activity, direct readouts include; determination of the AR and AR splice variant levels; modulation of AR activity by assessing levels of AR responsive genes including TMPRSS2 and KLK3. Other surrogate markers of AR functional activity include p21, c-Myc and p53. Given that multiple therapeutic agents which modulate AR activity are approved for use in CRPC, biomarkers to assess effects of p300 targeting and subsequent AR modulation are already widely available and used in clinical settings.

Various types of cancer have been shown to express AR. In addition to prostate cancer, these include breast and bladder cancer. Modulation of p300 activity would be expected to have therapeutic utility in the treatment of such cancers and other indications in which AR is expressed. In addition, it is feasible that p300 regulates the levels of other nuclear hormone receptors, thereby further expanding the clinical utility of p300 targeted agents.

A recent publication (Ogiwara et al. (2016) Cancer Discovery. 6; 430-445) has shown that tumours which harbour loss of function mutations in CBP are uniquely sensitive to p300 inhibition. Conversely tumours with mutations of p300 are uniquely sensitive to CBP inhibition. In lung cancer, genetic analysis reveals that up to 15% of both non-small cell and small cell tumours have these loss of function mutations. Similar mutations are also found in up to 25% of bladder cancers, as well as in a number of haematological malignancies, including lymphoma and leukaemia. Modulation of p300 and/or CBP would be expected to have therapeutic utility in tumours which harbour these mutations Further recent publications (Casey et al. (2016) Science. 352; 227-231; Ghosh et al. (2016) JBC on line) has shown that CBP/p300 regulates the expression of key immune checkpoint proteins such as CTLA4/PDL1 as well as the differentiation and function of t-regulatory cells. Modulation of p300 and/or CBP would be expected to provide additional therapeutic utility when combined with agents that target the immune-oncology system.

A compound of the invention has activity as a modulator p300 and/or CBP activity. It may therefore be used to treat cancer, or another clinical condition in which AR is expressed or in cancers in which there is activation of CBP and/or p300 function. The cancers that can be treated include those which express AR or are otherwise associated with AR, those that harbour loss of function mutations in CBP or p300 and those which have activated CBP and/or p300.

Cancers that may be treated include, but are not restricted to, prostate cancer, breast cancer, bladder cancer, lung cancer, lymphoma and leukaemia. The prostate cancer may be, for instance, castration-resistant prostate cancer (CRPC). The lung cancer may be, for instance, non-small cell lung cancer or small cell lung cancer. A human or animal patient suffering from cancer may thus be treated by a method comprising the administration thereto of a compound of the invention. The condition of the patient may thereby be improved or ameliorated.

A compound of the invention may thus be administered to a human or animal patient in conjunction with radiotherapy or another therapeutic agent for the treatment of cancer. The present invention therefore further provides a combination therapy wherein a compound of the invention, or a pharmaceutical composition comprising a compound of the invention, is administered concurrently or sequentially with radiotherapy; or is administered concurrently sequentially or as a combined preparation with another therapeutic agent or agents, for the treatment of cancer.

The or each other therapeutic agent will be an agent conventionally used for the type of cancer being treated. Classes of therapeutic agents with which a compound of the invention is typically combined for the treatment of prostate cancer include androgen receptor antagonists, for instance Enzalutamide, and inhibitors of CYP17A1 (17α-hydroxylase/C17,20 lyase), for instance Abiraterone; cyctotoxic chemotherapy, for instance Docetaxel; for the treatment of lung cancer include cytotoxic chemotherapies, for instance cisplatin, carboplatin, docetaxel; for the treatment of bladder cancer include cytotoxic chemotherapies, for instance gemcitabine, cisplatin or immune therapies, for instance, bacillus calmette-guérin (BCG). Other classes of agents with which a compound of the invention could be combined with include immune checkpoint inhibitors, for instance pembrolizumab, nivolumab, atezolizumab, ipilumumab; inhibitors of PARP (poly ADP ribose polymerase) such as Olaparib; and inhibitors of CDK4/6 (cyclin-dependant kinase 4 and 6).

The term "combination" as used herein refers to simultaneous, separate or sequential administration. Where the administration is sequential or separate, the delay in administering the second component should not be such as to lose the beneficial effect of the combination.

The present invention further provides a product comprising
(a) a compound of the invention as defined above; and
(b) one or more other therapeutic agent or agents;
for separate, simultaneous or sequential administration in the prophylactic or therapeutic treatment of cancer, for instance the specific types of cancer mentioned above. The other therapeutic agent may be, for instance, an androgen receptor antagonist, an inhibitor of CYP17A1, an inhibitor of PARP or an inhibitor of CDK4/6. More specifically, it may Enzalutamide, Abiraterone or Olaparib.

A compound of the invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A compound of the invention is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan monooleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents.

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables.

C) By inhalation, in the form of aerosols or solutions for nebulizers.

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols.

E) Topically, in the form of creams, ointments, jellies, collyriums, solutions or suspensions.

The invention will be further described in the Examples and Reference Examples which follow:

TABLE 1

| Abbreviations | |
|---|---|
| AcOH | glacial acetic acid |
| aq | aqueous |
| Ac | acetyl |
| Boc | tert-butoxycarbonyl |
| br | broad |
| CatCart ® | catalytic cartridge |
| CDI | 1,1-carbonyl-diimidazole |
| d | doublet |
| DCM | Dichloromethane |
| DIPEA | N,N-diisopropylethylamine |
| DMF | N,N-dimethylformamide |
| DMSO | dimethyl sulfoxide |
| (ES$^+$) | electrospray ionization, positive mode |
| Et | Ethyl |
| EtOAc | ethyl acetate |
| FCS | foetal calf serum |
| HOBt | 1-hydroxybenzotriazole |
| hr | hour(s) |
| (M + H)$^+$ | protonated molecular ion |
| Me | methyl |
| MeCN | acetonitrile |
| MeOH | methanol |
| MHz | megahertz |
| min | minute(s) |
| m/z: | mass-to-charge ratio |
| NMP | 1-methylpyrrolidin-2-one (N-methyl-2-pyrrolidone) |
| NMR | nuclear magnetic resonance (spectroscopy) |

TABLE 1-continued

Abbreviations

| | |
|---|---|
| PdCl2dppf | (1,1'-Bis(diphenylphospino)ferrocene)palladium(II) dichloride |
| Ph | phenyl |
| PBS | phosphate buffered saline |
| PPh$_3$ | triphenylphosphine |
| q | quartet |
| RT | room temperature |
| RP HPLC | reverse phase high performance liquid chromatography |
| s | singlet |
| SCX | solid supported cation exchange (resin) |
| S$_N$Ar | nucleophilic aromatic substitution |
| t | triplet |
| TBAF | tetrabutylammonium fluoride |
| TEA | triethylamine |
| TFA | trifluoroacetic acid |
| THF | tetrahydrofuran |
| TIPS-Cl | chlorotriisopropylsilane |
| TMB | 3,3',5,5'-tetramethylbenzidine |
| XantPhos | 4,5-bis(diphenylphosphino)-9,9-dimethylxanthene |

General Procedures

All starting materials and solvents were either obtained from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 μM) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% NH$_3$ in MeOH.

Analytical Methods

Reverse Phase High Performance Liquid Chromatography:

Analytical HPLC was carried out using a Waters Xselect CSH C18, 2.5 μm, 4.6×30 mm column eluting with a gradient of 0.1% Formic Acid in MeCN in 0.1% aqueous Formic Acid; a Waters Xbridge BEH C18, 2.5 μm, 4.6×30 mm column eluting with a gradient of MeCN in aqueous 10 mM Ammonium Bicarbonate. UV spectra of the eluted peaks were measured using either a diode array or variable wavelength detector on an Agilent 1100 system.

Analytical LCMS was carried out using a Waters Xselect CSH C18, 2.5 μm, 4.6×30 mm column eluting with a gradient of 0.1% Formic Acid in MeCN in 0.1% aqueous Formic Acid (Method 1); a Waters Xbridge BEH C18, 2.5 μm, 4.6×30 mm column eluting with a gradient of MeCN in aqueous 10 mM Ammonium Bicarbonate (Method 2). UV and mass spectra of the eluted peaks were measured using a variable wavelength detector on either an Agilent 1200 with or an Agilent Infinity 1260 LCMS with 6120 single quadrupole mass spectrometer with positive and negative ion electrospray.

Analytical UPLC/MS was carried out using a Waters Acquity CSH C18, 1.7 μm, 2.1×30 mm column eluting with a gradient of 0.1% Formic acid in MeCN in 0.1% Formic acid in water. The gradient is structured with a starting point of 5% MeCN held from 0.0-0.11 minutes. The gradient from 5-95% occurs between 0.11-2.15 minutes with a flush from 2.15-2.56 minutes. A column re-equilibration to 5% MeCN is from 2.56-2.83 minutes. UV spectra of the eluted peaks were measured using an Acquity PDA and mass spectra were recorded using an Acquity QDa detector with ESI pos/neg switching.

Preparative HPLC was carried out using a Waters Xselect CSH C18, 5 μm, 19×50 mm column using either a gradient of either 0.1% Formic Acid in MeCN in 0.1% aqueous Formic Acid or a gradient of MeCN in aqueous 10 mM Ammonium Bicarbonate; or a Waters Xbridge BEH C18, 5 μm, 19×50 mm column using a gradient MeCN in aqueous 10 mM Ammonium Bicarbonate. Fractions were collected following detection by UV at a single wavelength measured by a variable wavelength detector on a Gilson 215 preparative HPLC or Varian PrepStar preparative HPLC; by mass and UV at a single wavelength measured by a ZQ single quadrupole mass spectrometer, with positive and negative ion electrospray, and a dual wavelength detector on a Waters FractionLynx LCMS.

1H NMR Spectroscopy: 1H NMR spectra were acquired on a Bruker Avance III spectrometer at 400 MHz. Either the central peaks of chloroform-d, dimethylsulfoxide-d6 or an internal standard of tetramethylsilane were used as references.

$^1$H NMR Spectroscopy:

$^1$H NMR spectra were acquired on a Bruker Avance III spectrometer at 400 MHz using residual undeuterated solvent as reference

Example 1

(1S,4r)-4-(2-((S)-1-(3,4-difluorophenyl)-5-oxopyrrolidin-2-yl)-5-(1,4-dimethyl-1H-1,2,3-triazol-5-yl)-1H-benzo[d]imidazol-1-yl)cyclohexyl Acetate (S)-1-(3,4-difluorophenyl)-5-oxopyrrolidine-2-carboxylic Acid

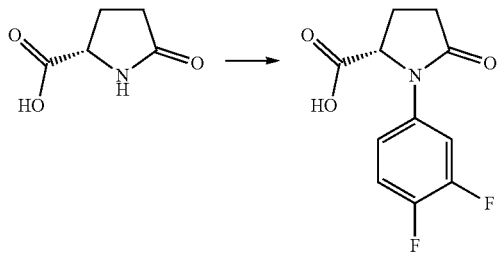 [SMILES: O=C1CC[C@@H](C(=O)O)N1 ; O=C(O)[C@@H]1CCC(=O)N1c1ccc(F)c(F)c1]

DBU (20 ml, 133 mmol) was added to a suspension of (S)-5-oxopyrrolidine-2-carboxylic acid (8.0 g, 62.0 mmol) in acetonitrile (15 mL) then stirred for 10 minutes at room temperature. CuTMEDA (1.5 g, 3.23 mmol) was added then the mixture was stirred for a further 10 minutes. (3,4-Difluorophenyl)boronic acid (10.0 g, 63.3 mmol) was added then the mixture was heated to 50° C. for 18 h. The residue was diluted with water (200 mL) then extracted with diethyl ether (2×200 mL). The aqueous layer was treated with 1 M aqueous hydrogen chloride (200 ml, 200 mmol) then extracted with ethyl acetate (3×200 mL). The combined organic phases were concentrated onto loose silica gel. The silicate was purified on a silica gel filter plug, eluting with EtOAc/dichloromethane (0-100%) to give a gel like film which retained excessive solvent. After prolonged rotary evaporation (with occasional grinding with a glass rod) at <10 mbar, 45° C. (S)-1-(3,4-difluorophenyl)-5-oxopyrrolidine-2-carboxylic acid (2.8 g, 16%) was obtained as a pale yellow glass; Rt 1.41 min (method 1); m/z 242.

Trans-(1r,4r)-4-((4-bromo-2-nitrophenyl)amino)cyclohexanol

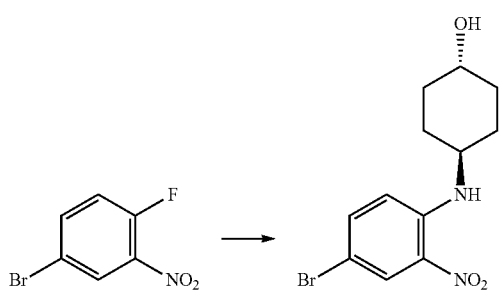 [SMILES: O=[N+]([O-])c1cc(Br)ccc1F ; O=[N+]([O-])c1cc(Br)ccc1N[C@H]1CC[C@H](O)CC1]

4-Bromo-1-fluoro-2-nitrobenzene (2.85 mL, 23.14 mmol), trans-(1r,4r)-4-aminocyclohexanol (4.00 g, 34.7 mmol) and TEA (6.45 mL, 46.3 mmol) were heated to reflux in THF (83 mL, 1018 mmol) for 48 h. The reaction was cooled down to RT, then the solvents were evaporated in vacuo and the orange residue was partitioned between EtOAc (100 mL) and DCM (100 mL) and saturated aqueous NaHCO₃ (100 mL) and the layers separated. The aqueous phase was extracted with further DCM (2×100 mL) and the combined organic extracts washed with water (100 mL) and brine (100 mL). The solution was concentrated onto loose silica gel. The silicate was purified by chromatography on the Companion (80 g column, 0-100% EtOAc/isohexane) to afford trans-(1r,4r)-4-((4-bromo-2-nitrophenyl) amino)cyclohexanol (5.79, 78%) as an orange solid; Rt 2.22 min (method 1); m/z 316.

Trans-(1r,4r)-4-((2-amino-4-bromophenyl)amino) cyclohexanol

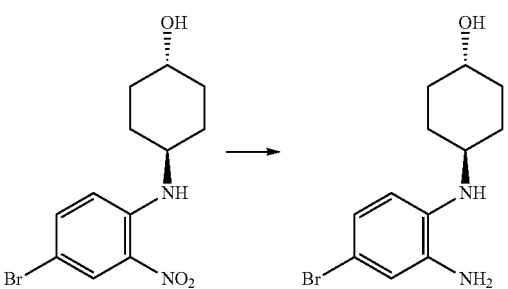 [SMILES: O=[N+]([O-])c1cc(Br)ccc1N[C@H]1CC[C@H](O)CC1 ; Nc1cc(Br)ccc1N[C@H]1CC[C@H](O)CC1]

Trans-(1r,4r)-4-((4-bromo-2-nitrophenyl)amino)cyclohexanol (5.79 g, 18.37 mmol) and concentrated ammonia (11.45 mL, 294 mmol) were dissolved in THF (175 mL, 2131 mmol) and WATER (174 mL, 9682 mmol). Sodium dithionite (37.9 g, 184 mmol) was added and the reaction mixture stirred at RT for 18 hours. The layers were separated, the aqueous further extracted with EtOAc (100 ml), and the combined organics washed with brine (50 mL), dried (MgSO₄), filtered and evaporated in vacuo to give trans-(1r,4r)-4-((2-amino-4-bromophenyl)amino)cyclohexanol (3.87 g, 72%) as a pink solid; Rt 1.16 min (method 1); m/z 285.

(S)—N-(5-bromo-2-((trans-(1r,4r)-4-hydroxycyclohexyl)amino)phenyl)-1-(3,4-difluorophenyl)-5-oxopyrrolidine-2-carboxamide (Intermediate C1)

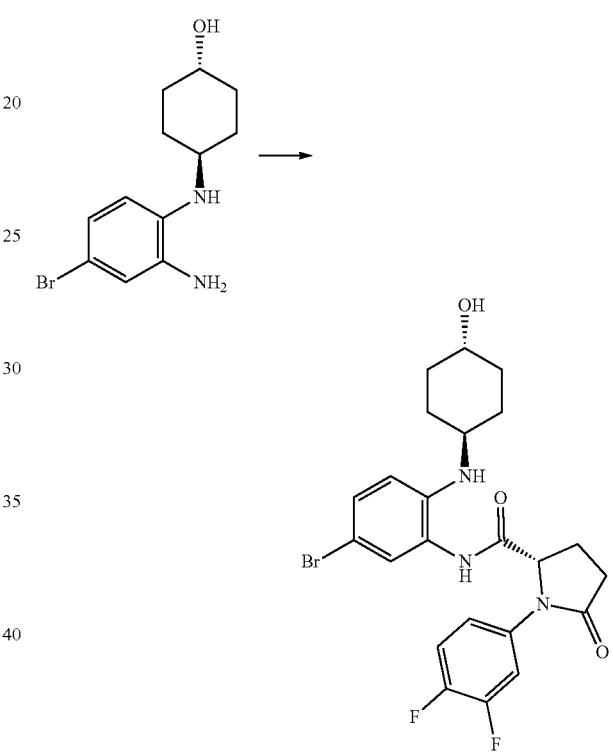

DIPEA (1.646 mL, 9.42 mmol) was added to a solution of trans-(1r,4r)-4-((2-amino-4-bromophenyl)amino)cyclohexanol (1.129 g, 3.96 mmol), (S)-1-(3,4-difluorophenyl)-5-oxopyrrolidine-2-carboxylic acid (1 g, 4.15 mmol) and HATU (1.863 g, 4.90 mmol) in DMF (12 mL, 155 mmol). The brown solution was stirred at RT for 4 h then the mixture was partitioned between ethyl acetate (50 mL) and water (50 mL), and the layers separated. The organic phase was washed with water (50 mL) and with brine (50 ml), concentrated in vacuo to give a crude dark oil (3.3 g), which was purified by chromatography on the Companion (40 g column, 0-10% MeOH/DCM) to afford (S)—N-(5-bromo-2-((trans-(1r,4r)-4-hydroxy cyclohexyl)amino)phenyl)-1-(3,4-difluorophenyl)-5-oxopyrrolidine-2-carboxamide (965 mg, 45%) as a pink foam; Rt 1.92 min (method 1); m/z 508.

35

(1S,4r)-4-(5-bromo-2-((S)-1-(3,4-difluorophenyl)-5-oxopyrrolidin-2-yl)-1H-benzo[d]imidazol-1-yl)cyclohexyl Acetate

36

(1S,4r)-4-(2-((S)-1-(3,4-difluorophenyl)-5-oxopyrrolidin-2-yl)-5-(1,4-dimethyl-1H-1,2,3-triazol-5-yl)-1H-benzo[d]imidazol-1-yl)cyclohexyl Acetate

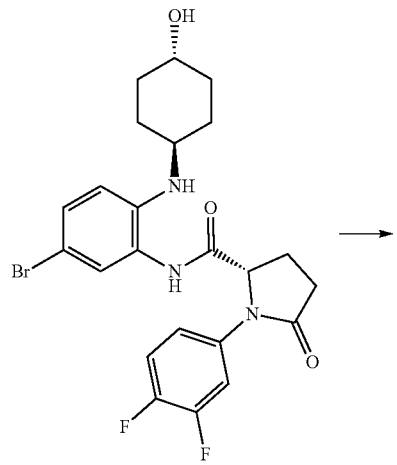

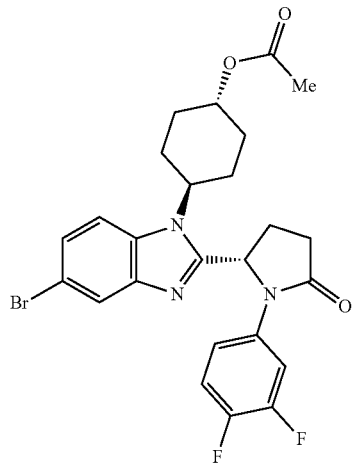

(S)—N-(5-bromo-2-((trans-(1r,4r)-4-hydroxycyclohexyl)amino)phenyl)-1-(3,4-difluorophenyl)-5-oxopyrrolidine-2-carboxamide (962 mg, 1.703 mmol) was dissolved in acetic acid (7.5 mL, 131 mmol) and stirred at 70° C. for 20 h, cooled down to RT and concentrated in vacuo. The crude product was purified by chromatography on silica gel (40 g column, 0-10% MeOH/DCM) to afford (1S,4r)-4-(5-bromo-2-((S)-1-(3,4-difluorophenyl)-5-oxopyrrolidin-2-yl)-1H-benzo[d]imidazol-1-yl)cyclohexyl acetate (480 mg, 37%) as a colourless solid; Rt 2.37 min (method 1); m/z 532.

1,4-Dimethyl-1H-1,2,3-triazole (27.4 mg, 0.282 mmol), potassium acetate (92 mg, 0.939 mmol), PdOAc$_2$ (4.22 mg, 0.019 mmol), (1S,4r)-4-(5-bromo-2-((S)-1-(3,4-difluorophenyl)-5-oxopyrrolidin-2-yl)-1H-benzo[d]imidazol-1-yl)cyclohexyl acetate (100 mg, 0.188 mmol) and cataCXium® A (13.47 mg, 0.038 mmol) were suspended in 2-methylbutan-2-ol (1234 µl, 11.27 mmol) under nitrogen. The reaction mixture was purged with nitrogen for 5 min and then heated to 100° C. for 18 h. The reaction was cooled to RT and partitioned between EtOAc (40 mL) and water (30 mL). The organic phase was separated, washed with brine (25 mL) and then dried over MgSO$_4$, filtered and concentrated in vacuo to afford a yellow oil, which was purified by chromatography on silica gel (24 g column, 0-5% MeOH/DCM) to afford (1S,4r)-4-(2-((S)-1-(3,4-difluorophenyl)-5-oxopyrrolidin-2-yl)-5-(1,4-dimethyl-1H-1,2,3-triazol-5-yl)-1H-benzo[d]imidazol-1-yl)cyclohexyl acetate (38 mg, 36%) as a colourless solid; Rt 1.93 min (method 1), m/z 549; 1H NMR (d6-DMSO) δ: 8.06 (1H, d, J=8.6 Hz), 7.84 (1H, ddd, J=13.3, 7.4, 2.7 Hz), 7.73 (1H, d, J=1.6 Hz), 7.38 (1H, dt, J=10.6, 9.2 Hz), 7.24 (1H, dd, J=8.5, 1.7 Hz), 7.16 (OH, d, J=9.3 Hz), 6.13 (1H, d, J=7.4 Hz), 5.06-4.94 (1H, m), 4.60 (1H, t, J=12.5 Hz), 3.90 (3H, s), 2.81-2.53 (3H, m), 2.48-2.39 (2H, m), 2.19 (3H, s), 2.15-2.05 (4H, m), 2.04 (3H, s), 1.98-1.88 (1H, m), 1.88-1.79 (1H, m), 1.79-1.63 (2H, m).

Example 2

(S)-1-(3,4-difluorophenyl)-5-(5-(1,4-dimethyl-1H-1,2,3-triazol-5-yl)-1-((1r,4S)-4-hydroxycyclohexyl)-1H-benzo[d]imidazol-2-yl)pyrrolidin-2-one

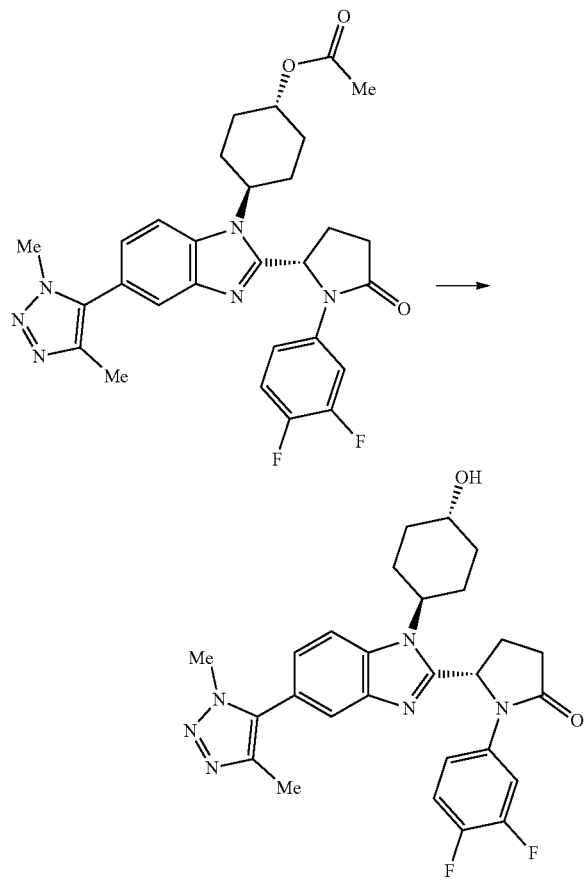

(1 S,4r)-4-(2-((S)-1-(3,4-difluorophenyl)-5-oxopyrrolidin-2-yl)-5-(1,4-dimethyl-1H-1,2,3-triazol-5-yl)-1H-benzo[d]imidazol-1-yl)cyclohexyl acetate (27 mg, 0.049 mmol) was diluted in MeOH (1991 µl, 49.2 mmol). Potassium carbonate (20.41 mg, 0.148 mmol) was added and the suspension was stirred at RT for 2 h. The reaction mixture was concentrated in vacuo, then the solid was dissolved in DCM (5 mL), sonicated and dry loaded on silica gel. The crude product was purified by flash chromatography on silica gel (12 g column, 0-10% MeOH/DCM) to afford (S)-1-(3,4-difluorophenyl)-5-(5-(1,4-dimethyl-1H-1,2,3-triazol-5-yl)-1-((1r,4S)-4-hydroxycyclohexyl)-1H-benzo[d]imidazol-2-yl)pyrrolidin-2-one (20 mg, 79%) as a colourless solid; Rt 1.52 min (method 1), m/z 507; 1H NMR (d6-DMSO) δ: 7.90 (d, J=8.5 Hz, 1H), 7.86-7.76 (m, 1H), 7.74-7.67 (m, 1H), 7.37 (q, J=9.4 Hz, 1H), 7.23 (dd, J=8.5, 1.7 Hz, 1H), 7.21-7.14 (m, 1H), 6.12 (d, J=7.9 Hz, 1H), 4.72-4.67 (m, 1H), 4.59-4.42 (m, 1H), 3.89 (s, 3H), 3.80-3.65 (m, 1H), 2.83-2.60 (m, 2H), 2.59-2.52 (m, 1H), 2.42-2.25 (m, 2H), 2.19 (s, 3H), 2.14-2.08 (m, 1H), 1.99 (s, 2H), 1.89-1.80 (m, 1H), 1.80-1.72 (m, 1H), 1.62-1.39 (m, 2H).

Example 3

(S)-5-(1-(4,4-difluorocyclohexyl)-5-(1,4-dimethyl-1H-1,2,3-triazol-5-yl)-1H-benzo[d]imidazol-2-yl)-1-(3,4-difluorophenyl)pyrrolidin-2-one 4-Bromo-N-(4,4-difluorocyclohexyl)-2-nitroaniline

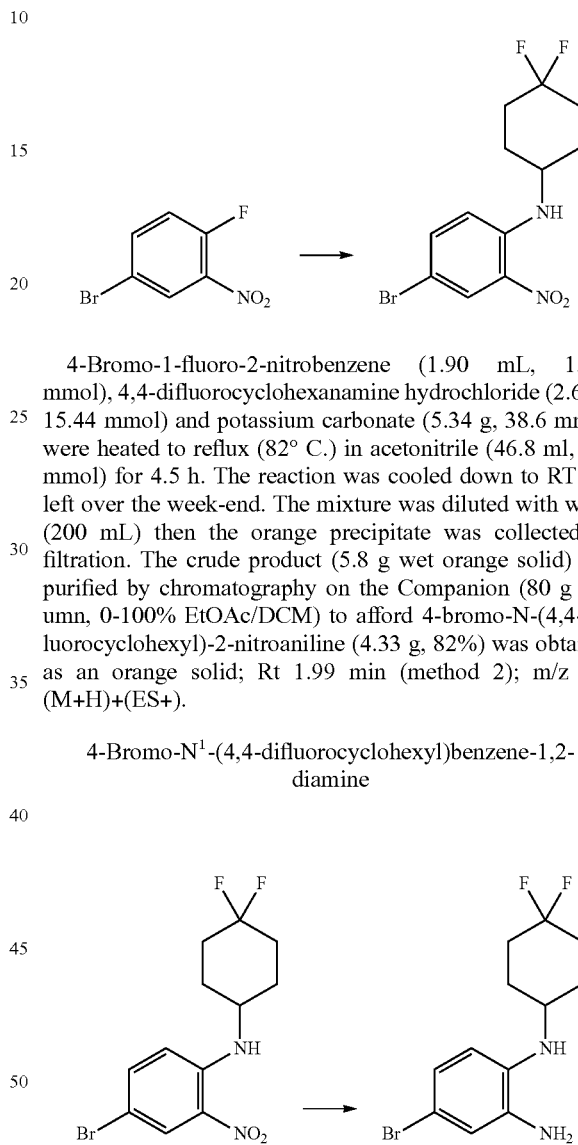

4-Bromo-1-fluoro-2-nitrobenzene (1.90 mL, 15.44 mmol), 4,4-difluorocyclohexanamine hydrochloride (2.65 g, 15.44 mmol) and potassium carbonate (5.34 g, 38.6 mmol) were heated to reflux (82° C.) in acetonitrile (46.8 ml, 896 mmol) for 4.5 h. The reaction was cooled down to RT and left over the week-end. The mixture was diluted with water (200 mL) then the orange precipitate was collected by filtration. The crude product (5.8 g wet orange solid) was purified by chromatography on the Companion (80 g column, 0-100% EtOAc/DCM) to afford 4-bromo-N-(4,4-difluorocyclohexyl)-2-nitroaniline (4.33 g, 82%) was obtained as an orange solid; Rt 1.99 min (method 2); m/z 381 (M+H)+(ES+).

4-Bromo-N$^1$-(4,4-difluorocyclohexyl)benzene-1,2-diamine

Sodium dithionite (26.6 g, 129 mmol) was added to a mixture of 4-bromo-N-(4,4-difluorocyclohexyl)-2-nitroaniline (4.33 g, 12.92 mmol), concentrated ammonia (9.81 ml, 252 mmol), water (39.1 mL, 2171 mmol) and THF (48.7 mL, 594 mmol) then stirred at room temperature for 18 h. The reaction mixture was filtered to remove the white solid. The solid was washed with AcOEt (100 mL). The layers were separated, the aqueous extracted with EtOAc (2×100 mL), the combined organics washed with water (50 mL) and brine (50 mL), dried (MgSO$_4$), filtered and evaporated in vacuo into a crude oil (2.89 g). The crude was loaded on SCX (Capture and release), eluting with MeOH then 1% NH3 in MeOH to give 4-bromo-N$_1$-(4,4-difluorocyclohexyl)benzene-1,2-diamine (2.53 g, 63%) was isolated as a sticky purple oil; Rt 2.21 min (method 1); m/z 305.

(S)—N-(5-bromo-2-((4,4-difluorocyclohexyl)amino)phenyl)-5-oxopyrrolidine-2-carboxamide

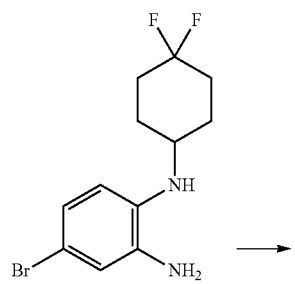

DIPEA (2.075 mL, 11.88 mmol) was added to a solution of 4-bromo-N¹-(4,4-difluorocyclohexyl)benzene-1,2-diamine (1.45 g, 4.75 mmol), (S)-5-oxopyrrolidine-2-carboxylic acid (0.675 g, 5.23 mmol) and HATU (2.349 g, 6.18 mmol) in DMF (15.82 mL, 204 mmol). The brown solution was stirred at RT for 15 h. The reaction was poured into water (100 mL). A suspension was formed which was difficult to filter; DCM (100 mL) was added. The organic filtrate was washed with water (2×100 mL). The aqueous was extracted twice with DCM (50 mL) and the organics were combined and washed with brine (100 mL), dried on MgSO₄, filtered and concentrated in vacuo to give a dark red oil solid mixture. The crude was purified by flash chromatography (40 g, using DCM/AcOEt: 100/0 to 50/50) to give (S)—N-(5-bromo-2-((4,4-difluorocyclohexyl)amino)phenyl)-5-oxopyrrolidine-2-carboxamide (1.92 g, 87%) was isolated as a brown foam; Rt 1.92 min (method 1); m/z 417.

(S)-5-(5-bromo-1-(4,4-difluorocyclohexyl)-1H-benzo[d]imidazol-2-yl)pyrrolidin-2-one

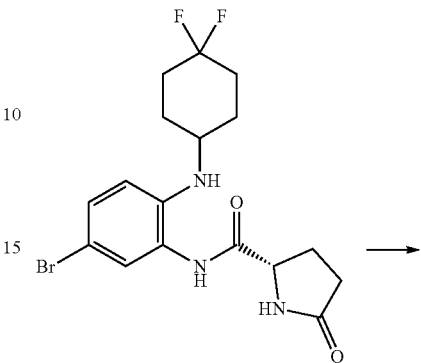

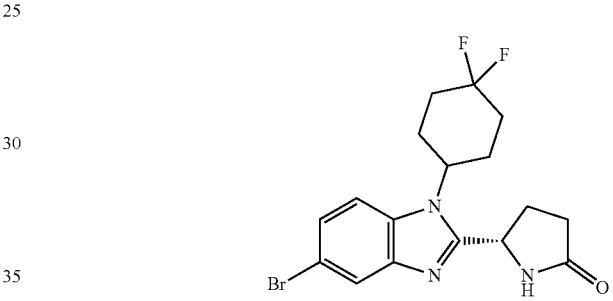

(S)—N-(5-bromo-2-((4,4-difluorocyclohexyl)amino)phenyl)-5-oxopyrrolidine-2-carboxamide (1.92 g, 4.61 mmol) was dissolved in acetic acid (18.48 mL, 323 mmol) and stirred at 70° C. for 15 h. The reaction was cooled down to RT and concentrated in vacuo. The crude brown oil was purified by flash chromatography (4 g companion, using DCM/MeOH: 100/0 to 90/10) to give (S)-5-(5-bromo-1-(4,4-difluorocyclohexyl)-1H-benzo[d]imidazol-2-yl)pyrrolidin-2-one (1.42 g, 3.39 mmol, 73.4% yield) was isolated as a pink brown solid; Rt 1.84 min (method 1); m/z 399.

(S)-5-(5-bromo-1-(4,4-difluorocyclohexyl)-1H-benzo[d]imidazol-2-yl)-1-(3,4-difluorophenyl)pyrrolidin-2-one

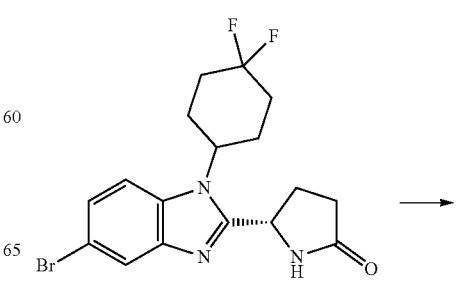

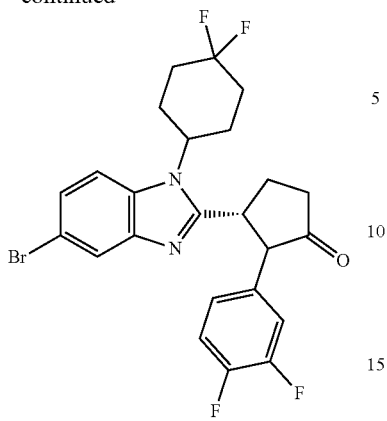

CuTMEDA (0.711 g, 1.532 mmol) was added to a stirred solution of (S)-5-(5-bromo-1-(4,4-difluorocyclohexyl)-1H-benzo[d]imidazol-2-yl)pyrrolidin-2-one (1.22 g, 3.06 mmol) in PYRIDINE (36.9 ml, 456 mmol) then the mixture was stirred for 15 min at 40° C. (3,4-difluorophenyl)boronic acid (1.28 g, 8.12 mmol) was added then the mixture was heated to 40° C. for 2.5 h. The reaction was cooled down to RT, then concentrated in vacuo to give a green residue which was diluted with ethyl acetate (100 mL) and filtered through a pad of Celite to remove the copper salts. The filtrate was washed with water (3×100 mL) and saturated brine (100 mL), filtered and concentrated under reduced pressure. The crude product was purified by flash chromatography on the Companion (24 g, DCM/AcOEt: 100/0 to 0/100) to give (S)-5-(5-bromo-1-(4,4-difluorocyclohexyl)-1H-benzo[d] imidazol-2-yl)-1-(3,4-difluorophenyl)pyrrolidin-2-one (1.23 g, 2.290 mmol, 74.7% yield) was isolated as a white foam; Rt 2.53 min (method 1); m/z 510.

(S)-5-(1-(4,4-difluorocyclohexyl)-5-(1,4-dimethyl-1H-1,2,3-triazol-5-yl)-1H-benzo[d]imidazol-2-yl)-1-(3,4-difluorophenyl)pyrrolidin-2-one

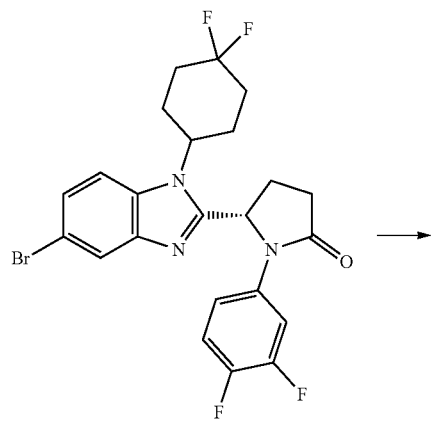

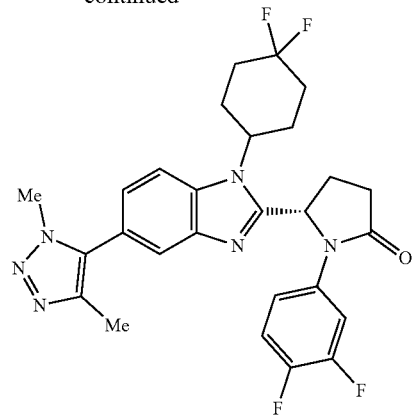

1,4-Dimethyl-1H-1,2,3-triazole (0.057 g, 0.588 mmol), potassium acetate (0.192 g, 1.960 mmol), PdOAc$_2$ (8.80 mg, 0.039 mmol) and di((3S,5S,7S)-adamantan-1-yl)(butyl) phosphine (cataCXium® A) (0.028 g, 0.078 mmol) were suspended in 2-methylbutan-2-ol (2.57 ml, 23.51 mmol) under nitrogen. The reaction mixture was purged with nitrogen for 5 min and then (S)-5-(5-bromo-1-(4,4-difluorocyclohexyl)-1H-benzo[d]imidazol-2-yl)-1-(3,4-difluoro phenyl)pyrrolidin-2-one (0.2 g, 0.392 mmol) was added. The green suspension was heated to 100° C. for 24 h. The reaction was cooled to RT and partitioned between EtOAc (40 mL) and water (30 ml). The organic phase was separated, washed with brine (25 ml) and then dried over MgSO4, filtered and concentrated in vacuo to afford a yellow oil. The crude product was purified by chromatography on silica gel (24 g column, 0-5% MeOH/DCM) to afford (S)-5-(1-(4,4-difluorocyclohexyl)-5-(1,4-dimethyl-1H-1,2,3-triazol-5-yl)-1H-benzo[d] imidazol-2-yl)-1-(3,4-difluorophenyl)pyrrolidin-2-one (69.5 mg, 33%) as beige solid; Rt 2.02 min (method 1), m/z 527 (M+H)+(ES+); 1H NMR (d6-DMSO) δ: 7.86 (ddd, J=13.3, 7.4, 2.7 Hz, 1H), 7.77 (d, J=1.5 Hz, 1H), 7.67 (d, J=8.5 Hz, 1H), 7.38 (q, J=10.6, 9.2 Hz, 1H), 7.32 (dd, J=8.5, 1.7 Hz, 1H), 7.22-7.14 (m, 1H), 6.12-6.06 (m, 1H), 4.88-4.77 (m, 1H), 3.90 (s, 3H), 2.81-2.61 (m, 2H), 2.61-2.42 (m, 3H), 2.31-2.21 (m, 3H), 2.19 (s, 3H), 2.17-1.93 (m, 4H).

Example 4

(S)-5-(1-(4,4-difluorocyclohexyl)-5-(1,4-dimethyl-1H-pyrazol-5-yl)-1H-benzo[d]imidazol-2-yl)-1-(3,4-difluorophenyl)pyrrolidin-2-one

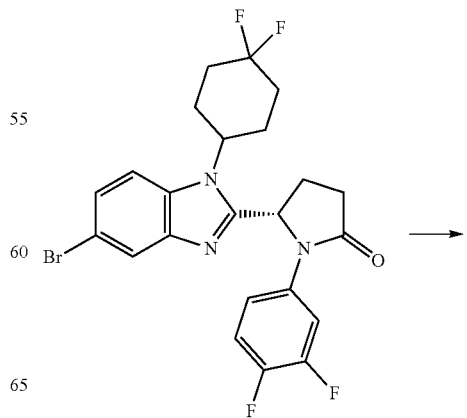

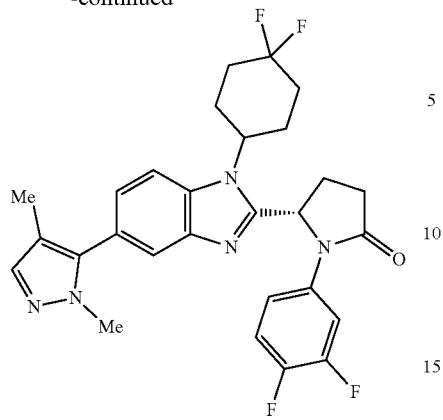

To a solution of (S)-5-(5-bromo-1-(4,4-difluorocyclohexyl)-1H-benzo[d]imidazol-2-yl)-1-(3,4-difluorophenyl)pyrrolidin-2-one (100 mg, 0.196 mmol), potassium carbonate (54.2 mg, 0.392 mmol) and 1,4-dimethyl-5-(4,4,5,5-tetramethyl-1,3,2-dioxaborolan-2-yl)-1H-pyrazole (56.6 mg, 0.255 mmol) in 1,4-dioxane (2 ml, 23.38 mmol) and water (0.4 ml, 22.20 mmol) was added Pd(Ph$_3$P)$_4$ (34.0 mg, 0.029 mmol). The mixture was degassed with nitrogen and heated at 90° C. for 5 h and then cooled to RT. The volatile was removed in vacuo. The residue was treated with water (20 mL) and extracted with DCM (3×20 mL). The organic extracts were combined and then dried over MgSO$_4$, filtered and concentrated in vacuo to afford a red oil, which was purified by flash chromatography on silica gel (12 g column, 0-40% THF/DCM) to give a colourless solid. The crude product was loaded onto a column of SCX (2 g) in MeOH. The column was washed with MeOH and then the product was eluted with 0.7 M ammonia in MeOH. The resultant mixture was concentrated in vacuo to afford (S)-5-(1-(4,4-difluorocyclohexyl)-5-(1,4-dimethyl-1H-pyrazol-5-yl)-1H-benzo[d]imidazol-2-yl)-1-(3,4-difluorophenyl)pyrrolidin-2-one (51 mg, 49%) as a colourless solid; Rt 2.22 min (method 1), m/z 526 (M+H)+(ES+); 1H NMR (d6-DMSO) δ: 7.86 (ddd, J=13.3, 7.4, 2.6 Hz, 1H), 7.69-7.60 (m, 2H), 7.47-7.33 (m, 1H), 7.30 (d, J=0.6 Hz, 1H), 7.26 (dd, J=8.6, 1.6 Hz, 1H), 7.22-7.15 (m, 1H), 6.08 (d, J=7.4 Hz, 1H), 4.83 (t, J=12.3 Hz, 1H), 3.68 (s, 3H), 2.85-2.62 (m, 2H), 2.61-2.52 (m, 1H), 2.49-2.42 (m, 2H), 2.34-2.10 (m, 5H), 2.08-2.01 (m, 1H), 2.01-1.95 (m, 1H), 1.94 (s, 3H).

Example 5

(S)-5-(1-(4,4-difluorocyclohexyl)-5-(1,4-dimethyl-1H-imidazol-5-yl)-1H-benzo[d]imidazol-2-yl)-1-(3,4-difluorophenyl)pyrrolidin-2-one

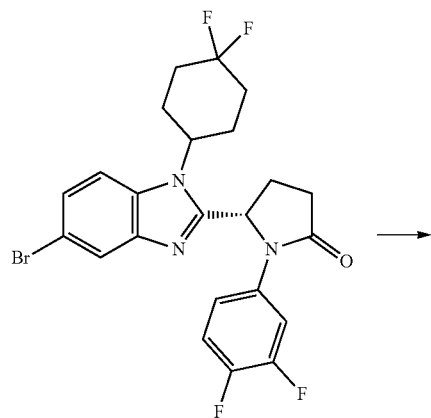

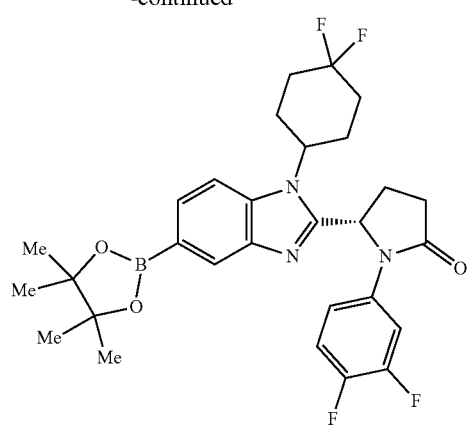

To a solution of (S)-5-(5-bromo-1-(4,4-difluorocyclohexyl)-1H-benzo[d]imidazol-2-yl)-1-(3,4-difluorophenyl)pyrrolidin-2-one (0.725 g, 1.421 mmol) and 4,4,4',4',5,5,5',5'-octamethyl-2,2'-bi(1,3,2-dioxaborolane) (0.541 g, 2.131 mmol) in 1,4-dioxane (11.84 ml, 1.421 mmol) was added potassium acetate (0.446 g, 4.55 mmol) and PdCl$_2$(dppf) (0.099 g, 0.135 mmol). The mixture was degassed with nitrogen and heated at 85° C. for 2 h and then cooled to RT. The reaction was heated for another 2 h and cooled down to RT overnight. The crude reaction mixture was filtered through a pad of Celite, washed with DCM (5 mL), then the volatiles were removed in vacuo and the oil was purified by flash chromatography on the Companion (12 g, 0-100% AcOEt/DCM) to afford the crude (S)-5-(1-(4,4-difluorocyclohexyl)-5-(4,4,5,5-tetramethyl-1,3,2-dioxaborolan-2-yl)-1H-benzo[d]imidazol-2-yl)-1-(3,4-difluorophenyl) pyrrolidin-2-one (0.746 g, 43%) as a brown foam; Rt 1.87 min (method 1), m/z 476 (M+H)+(ES+)– contaminated with (S)-5-(1-(4,4-difluorocyclohexyl)-1H-benzo[d]imidazol-2-yl)-1-(3,4-difluorophenyl)pyrrolidin-2-one as seen by LCMS and carried through in next step as a ca. 1:1 mixture.

(S)-5-(1-(4,4-difluorocyclohexyl)-5-(1,4-dimethyl-1H-imidazol-5-yl)-1H-benzo[d]imidazol-2-yl)-1-(3,4-difluorophenyl)pyrrolidin-2-one

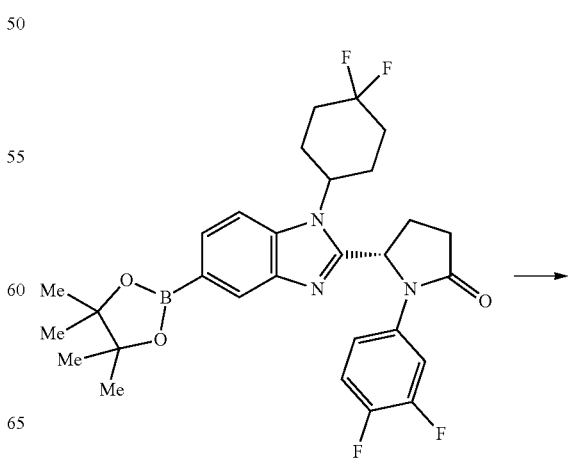

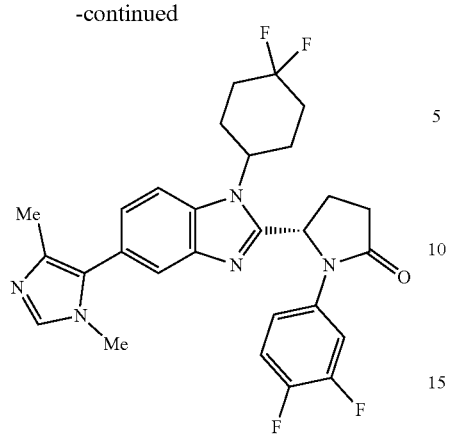

A mixture of water (0.308 mL, 17.12 mmol) and (S)-5-(1-(4,4-difluorocyclohexyl)-5-(4,4,5,5-tetramethyl-1,3,2-dioxaborolan-2-yl)-1H-benzo[d]imidazol-2-yl)-1-(3,4-difluorophenyl) pyrrolidin-2-one (0.373 g, 0.308 mmol) and 5-bromo-1,4-dimethyl-1H-imidazole (0.065 g, 0.369 mmol) in 1,4-dioxane (1.712 mL, 20.01 mmol) and potassium carbonate (0.128 g, 0.923 mmol) was purged with nitrogen for 10 mn. PdCl$_2$(dppf) (0.023 g, 0.031 mmol) was then added and the reaction mixture was heated at 90° C. for 15 h. Further 5-Bromo-1,4-dimethyl-1H-imidazole (30 mg) in 1,4-dioxane (0.5 mL) were added to the reaction mixture and stirring at the same temperature continued for 1.75 h. Fresh PdCl$_2$(dppf) (0.023 g, 0.031 mmol) was added and stirring continued for 1.5 h, then the reaction was cooled down to RT and partitioned between EtOAc (40 mL) and water (30 mL). The organic phase was separated, washed with brine (25 mL) and then dried over MgSO$_4$, filtered and concentrated in vacuo. The crude product was purified by chromatography on silica gel (4 g column, DCM/AcOEt: 100/0 to 0/100 then MeOH) to give a dark brown residue (97 mg). Further flash chromatography purification (4 g, Grace silica column, using DCM/AcOEt: 100/0 to 0/100 then DCM/MeOH: 100/0 to 90/10) afforded (S)-5-(1-(4,4-difluorocyclohexyl)-5-(1,4-dimethyl-1H-imidazol-5-yl)-1H-benzo[d]imidazol-2-yl)-1-(3,4-difluorophenyl)pyrrolidin-2-one (33 mg, 19%) was isolated as a green solid; Rt 1.47 min (method 1), m/z 526 (M+H)+(ES+); 1H NMR (d6-DMSO) δ: 7.85 (ddd, J=13.3, 7.4, 2.7 Hz, 1H), 7.62-7.56 (m, 2H), 7.53 (s, 1H), 7.38 (q, J=10.7, 9.2 Hz, 1H), 7.22 (dd, J=8.6, 1.6 Hz, 1H), 7.20-7.14 (m, 1H), 6.07 (dd, 1H), 4.87-4.75 (m, 1H), 3.32 (s, 3H), 2.80-2.59 (m, 2H), 2.58-2.41 (m, 2H), 2.31-2.20 (m, 3H), 2.20-2.09 (m, 2H), 2.08-2.00 (m, 4H), 1.99-1.91 (m, 2H).

Reference Examples: Synthesis of Intermediates Used in Examples 7-22

Intermediate 1:
Trans-4-((4-bromo-2-nitrophenyl)amino)cyclohexanol

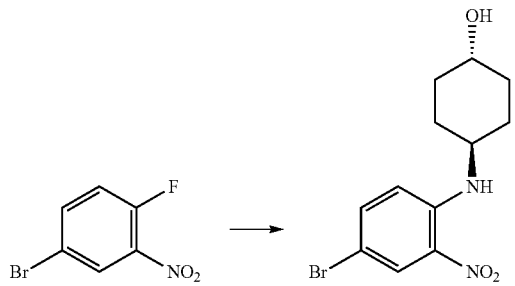 [SMILES: O=[N+]([O-])c1cc(Br)ccc1F ; O=[N+]([O-])c1cc(Br)ccc1N[C@H]1CC[C@H](O)CC1]

4-bromo-1-fluoro-2-nitrobenzene (5.0 g, 22.7 mmol), trans-4-aminocyclohexanol (4 g, 34.7 mmol) and potassium carbonate (5.0 g, 36.2 mmol) were stirred in acetonitrile at 80° C. for 3 h. The mixture was diluted with water (150 mL) and the precipitate was collected by filtration to yield trans-4-((4-bromo-2-nitrophenyl)amino)cyclohexanol (8 g, 22.6 mmol, 99% yield) as an orange solid. Used in the next step without further purification.

Intermediate 2:
4-Bromo-N-(4,4-difluorocyclohexyl)-2-nitroaniline

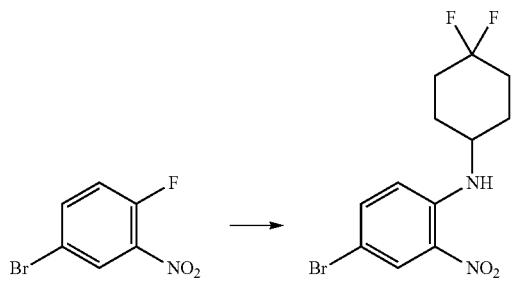 [SMILES: O=[N+]([O-])c1cc(Br)ccc1F ; O=[N+]([O-])c1cc(Br)ccc1NC1CCC(F)(F)CC1]

4-Bromo-1-fluoro-2-nitrobenzene (1.90 mL, 15.4 mmol), 4,4-difluorocyclohexanamine hydrochloride (2.65 g, 15.4 mmol) and potassium carbonate (5.3 g, 38.6 mmol) were heated to 80° C. in acetonitrile (46.8 ml, 896 mmol) for 4.5 h. The reaction was cooled down to RT and left over the week-end. The mixture was diluted with water (200 mL) then the orange precipitate was collected by filtration. The crude product was purified by flash chromatography (0-100% EtOAc/DCM) to afford 4-bromo-N-(4,4-difluorocyclohexyl)-2-nitroaniline (4.33 g, 82%) as an orange solid; R$_t$ 1.99 min (method 2); m/z 381 (M+H)+.

Intermediate 3: Cis-4-((4-bromo-2-nitrophenyl)amino)-1-methylcyclohexanol

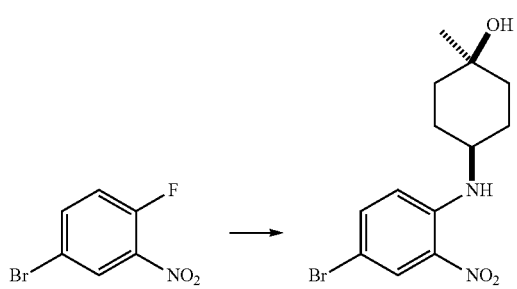

4-bromo-1-fluoro-2-nitrobenzene (5 g, 22.7 mmol), cis-4-amino-1-methylcyclohexanol (4.2 g, 32.7 mmol) and potassium carbonate (8.0 g, 57.9 mmol) were stirred in acetonitrile at 80° C. for 3 h. The mixture was diluted with water (150 mL) and the precipitate was collected by filtration to yield cis-4-((4-bromo-2-nitrophenyl)amino)-1-methylcyclohexanol (8.9 g, 22.7 mmol) as an orange solid which was used in the next step without further purification.

Intermediate 4: 4-Bromo-N-(trans-4-methoxycyclohexyl)-2-nitroaniline

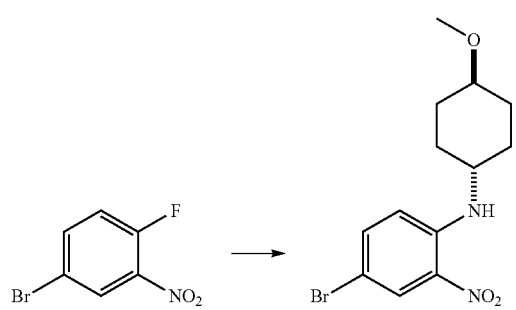

4-bromo-1-fluoro-2-nitrobenzene (5 g, 22.73 mmol), trans-4-methoxycyclohexanaminium chloride (5.0 g, 30.2 mmol) and potassium carbonate (10.0 g, 72.4 mmol) were stirred in acetonitrile at 70° C. for 3 h. The mixture was diluted with water (150 mL) and the precipitate was collected by filtration to yield 4-bromo-N-(trans-4-methoxycyclohexyl)-2-nitroaniline (8.5 g, 22.7 mmol) as an orange solid which was used in the next step without further purification.

Intermediate 5: Trans-(1r,4r)-4-((2-amino-4-bromophenyl)amino)cyclohexanol

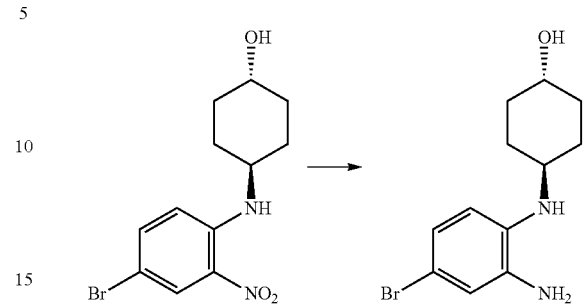

cans-(1r,4r)-4-((4-bromo-2-nitrophenyl)amino)cyclohexanol (5.8 g, 18.4 mmol) and concentrated ammonia (11.5 mL) were dissolved in THF (175 mL) and water (175 mL). Sodium dithionite (37.9 g, 184 mmol) was added and the reaction mixture stirred at RT for 18 hours. The layers were separated, the aqueous further extracted with EtOAc (100 ml), and the combined organics washed with brine (50 mL), dried (MgSO$_4$), filtered and evaporated in vacuo to give trans-(1r,4r)-4-((2-amino-4-bromophenyl)amino)cyclohexanol (3.87 g, 72%) as a pink solid; $R_t$ 1.16 min (method 1); m/z 285 (M+H)$^+$.

Intermediate 6: 4-Bromo-N$^1$-(4,4-difluorocyclohexyl)benzene-1,2-diamine

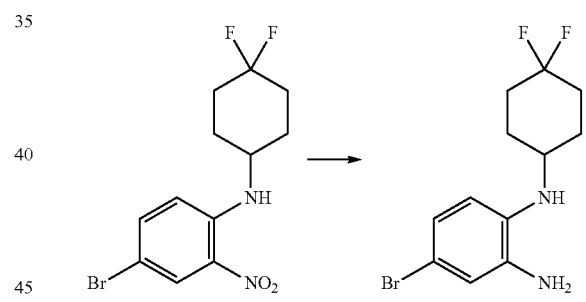

Sodium dithionite (26.6 g, 129 mmol) was added to a mixture of 4-bromo-N-(4,4-difluorocyclohexyl)-2-nitroaniline (4.33 g, 12.9 mmol), concentrated ammonia (9.81 ml, 252 mmol), water (39 mL) and THF (50 mL) then stirred at room temperature for 18 h. The reaction mixture was filtered to remove the white solid. The solid was washed with ethyl acetate (100 mL). The layers were separated and extracted with ethyl acetate (2×100 mL). The combined organic layers washed with water (50 mL) and brine (50 mL), dried (MgSO$_4$), filtered and evaporated in vacuo into a crude oil (2.89 g). The crude was loaded on SCX (Capture and release), eluting with MeOH then 1% NH3 in MeOH to give 4-bromo-N$_1$-(4,4-difluorocyclohexyl)benzene-1,2-diamine (2.53 g, 63%) was isolated as a sticky purple oil; $R_t$ 2.21 min (method 1); m/z 305 (M+H)$^+$.

Intermediate 7: Cis-4-((2-amino-4-bromophenyl)amino)-1-methylcyclohexanol

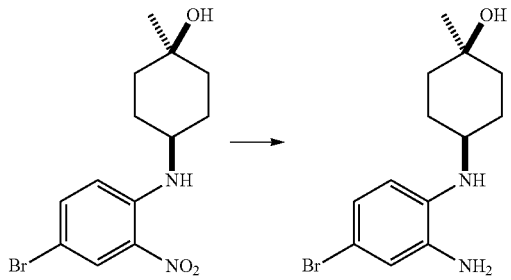

Sodium dithionite (15.0 g, 73.2 mmol) was added to a solution of cis-4-((4-bromo-2-nitrophenyl)amino)-1-methylcyclohexanol (8.9 g, 22.7 mmol) in tetrahydrofuran (75 mL), water (75 mL) and 28% ammonium hydroxide (17 mL). After 4 h the mixture was diluted with water (300 mL) then extracted with dichloromethane (3×300 mL). The combined organic phases were washed with saturated brine (300 mL) then dried (MgSO$_4$), filtered and concentrated under reduced pressure to yield cis-4-((2-amino-4-bromophenyl)amino)-1-methylcyclohexanol (5.0 g, 16.5 mmol, 73% yield) as a brown solid. The crude product was used in the next step without further purification. UPLC-MS: R$_t$ 0.91 min, m/z 299, 301 (M+H)$^+$.

Intermediate 8: 4-Bromo-N1-(trans-4-methoxycyclohexyl)benzene-1,2-diamine

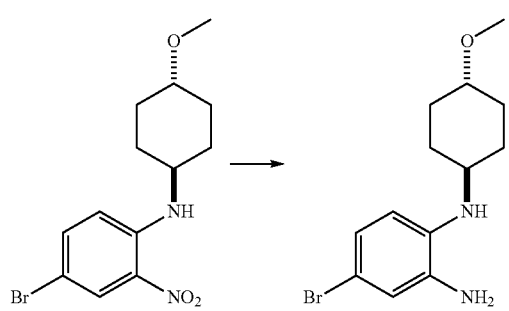

Sodium dithionite (20.0 g, 98 mmol) was added to a solution of 4-bromo-N-(trans-4-methoxycyclohexyl)-2-nitroaniline (8.5 g, 22.7 mmol) in tetrahydrofuran (75 L), water (75 L) and 28% ammonium hydroxide (17 mL). After 3 h the mixture was diluted with water (300 mL) then extracted with dichloromethane (3×300 mL). The combined organic phases were washed with saturated brine (300 mL) then dried (MgSO$_4$), filtered and concentrated under reduced pressure to yield 4-bromo-N1-(trans-4-methoxycyclohexyl)benzene-1,2-diamine (6.2 g, 20.5 mmol, 90% yield) as a brown solid. The crude product was used in the next step without further purification. UPLC-MS: R$_t$ 1.04 min, m/z 299, 301 (M+H)$^+$.

Intermediate 9: (S)—N-(5-bromo-2-((trans-4-hydroxycyclohexyl)amino)phenyl)-6-oxopiperidine-2-carboxamide

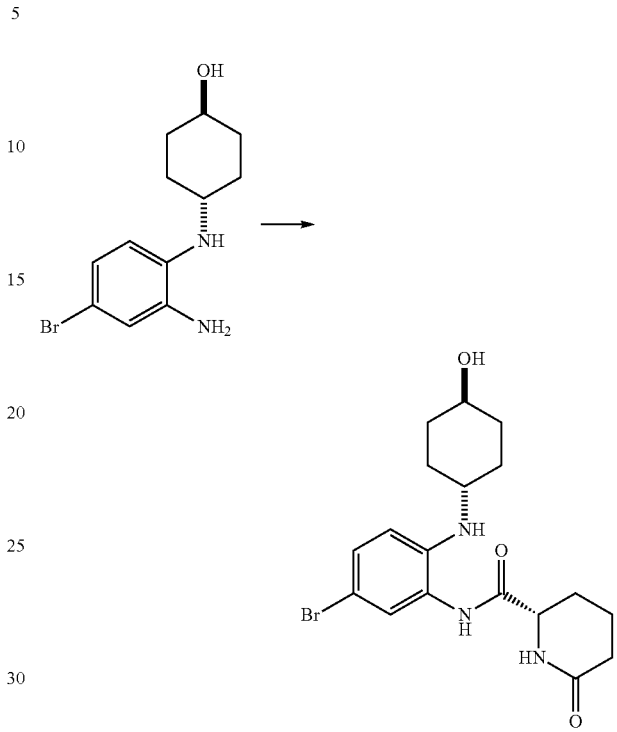

50% T3P® in ethyl acetate (10.0 mL, 17.8 mmol) was added dropwise to a stirred solution of trans-4-((2-amino-4-bromophenyl)amino)cyclohexanol (3.9 g, 13.5 mmol), (S)-6-oxopiperidine-2-carboxylic acid (2.0 g, 14.0 mmol) and DIPEA (3.0 ml, 17.2 mmol) in dichloromethane (50 mL). The mixture was stirred at room temperature for 3 h. The mixture was washed with water (50 mL) then loaded directly onto an 80 g silica gel column. The column was eluted with THF/DCM 25-100%, to afford a pink solid. The solid was triturated in DCM:TBME:isohexane (1:3:6, 50 mL) to yield (S)—N-(5-bromo-2-((trans-4-hydroxycyclohexyl)amino)phenyl)-6-oxopiperidine-2-carboxamide (2.5 g, 6.0 mmol, 46% yield) as a pale pink solid. UPLC-MS: R$_t$ 0.94 min, m/z 410, 412 (M+H)$^+$.

Intermediate 10: (S)—N-(5-bromo-2-((4,4-difluorocyclohexyl)amino)phenyl)-6-oxopiperidine-2-carboxamide

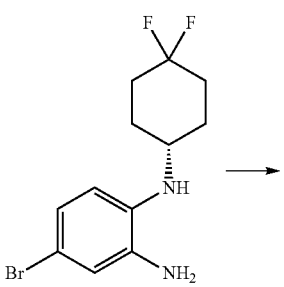

-continued

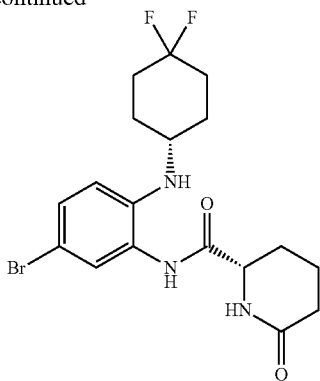

50% T3P® in ethyl acetate (10.0 mL, 17.8 mmol) was added dropwise to a stirred solution of 4-bromo-N1-(4,4-difluorocyclohexyl)benzene-1,2-diamine (4.2 g, 13.6 mmol), (S)-6-oxopiperidine-2-carboxylic acid (2.0 g, 14.0 mmol) and DIPEA (3.0 ml, 17.2 mmol) in dichloromethane (50 mL). The mixture was stirred at room temperature for 3 h. The mixture was washed with water (50 mL) then loaded directly onto an 80 g silica gel column. The column was eluted with THF/DCM 25-100%, to afford a pink solid. The solid was triturated in DCM:TBME:isohexane (1:3:6, 50 mL) to yield (S)—N-(5-bromo-2-((4,4-difluorocyclohexyl)amino)phenyl)-6-oxopiperidine-2-carboxamide (4.3 g, 9.9 mmol, 73% yield) as a pale pink solid. UPLC-MS: $R_t$ 1.29 min, m/z 430, 432 (M+H)$^+$.

Intermediate 11: (S)—N-(5-bromo-2-((cis-4-hydroxy-4-methylcyclohexyl)amino)phenyl)-6-oxopiperidine-2-carboxamide

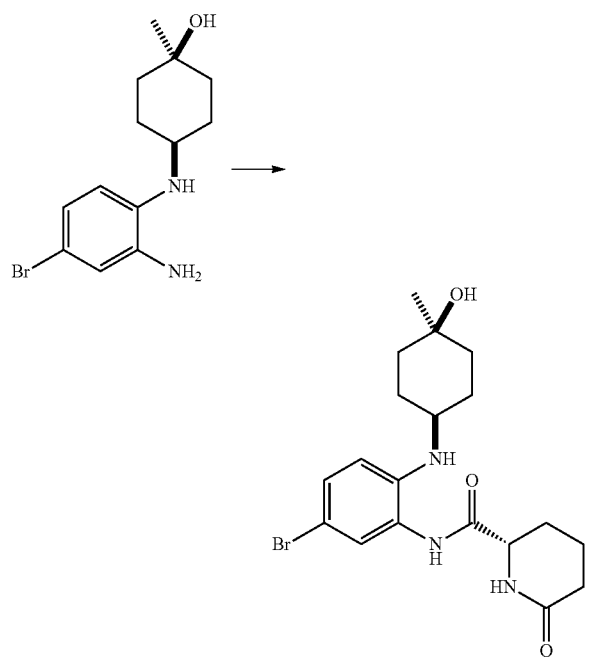

50% T3P® in ethyl acetate (11.0 mL, 19.5 mmol) was added dropwise to a stirred solution of cis-4-((2-amino-4-bromophenyl)amino)-1-methylcyclohexanol (5.0 g, 16.5 mmol), (S)-6-oxopiperidine-2-carboxylic acid (2.5 g, 17.5 mmol) and DIPEA (3.5 ml, 20.0 mmol) in dichloromethane (50 mL). The mixture was stirred at room temperature for 3 h. The mixture was washed with water (50 mL) then loaded directly onto an 80 g silica gel column. The column was eluted with THF/DCM 25-100%, to afford a pink solid. The solid was triturated in DCM:TBME:isohexane (1:3:6, 50 mL) to yield (S)—N-(5-bromo-2-((cis-4-hydroxy-4-methylcyclohexyl)amino)phenyl)-6-oxopiperidine-2-carboxamide (4.3 g, 10.0 mmol, 61% yield) as a pale pink solid. UPLC-MS: $R_t$ 1.13 min, m/z 424, 426 (M+H)$^+$.

Intermediate 12: (S)—N-(5-bromo-2-((trans-4-methoxycyclohexyl)amino)phenyl)-6-oxopiperidine-2-carboxamide

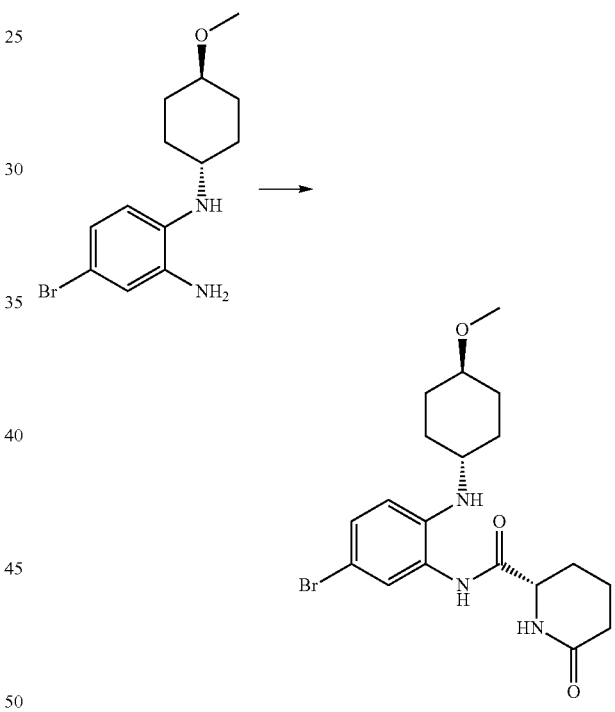

50% T3P® in ethyl acetate (10.0 mL, 17.8 mmol) was added dropwise to a stirred solution of 4-bromo-N1-(trans-4-methoxycyclohexyl)benzene-1,2-diamine (4.2 g, 14 mmol), (S)-6-oxopiperidine-2-carboxylic acid (2.2 g, 15 mmol) and DIPEA (3 ml, 17 mmol) in dichloromethane (50 mL). The mixture was stirred at room temperature for 3 h. The mixture was washed with water (50 mL) then loaded onto an 80 g silica gel column. The column was eluted with THF/DCM 25-100%, to afford a pink solid. The solid was triturated in DCM:TBME:isohexane (1:3:6, 50 mL) to yield (S)—N-(5-bromo-2-((trans-4-methoxycyclohexyl)amino)phenyl)-6-oxopiperidine-2-carboxamide (4.2 g, 9.80 mmol, 70% yield) as a pale pink solid. UPLC-MS: $R_t$ 1.14 min, m/z 424, 426 (M+H)$^+$.

Intermediate 13: (S)-6-(5-Bromo-1-(trans-4-hydroxycyclohexyl)-1H-benzo[d]imidazol-2-yl)piperidin-2-one

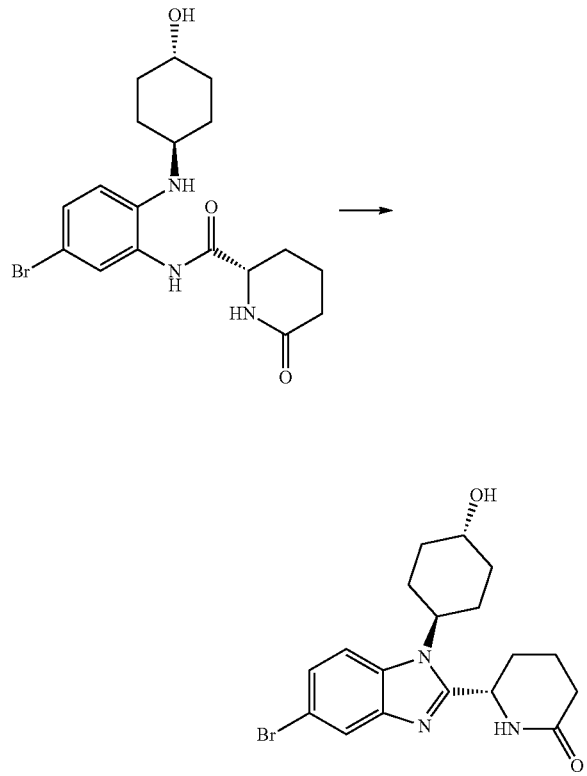

(S)—N-(5-bromo-2-((trans-4-hydroxycyclohexyl)amino) phenyl)-6-oxopiperidine-2-carboxamide (2.5 g, 6.03 mmol) was stirred in acetic acid (50 mL) at 50° C. for 5 days. The solvent was removed under reduced pressure then partitioned between saturated sodium hydrogen carbonate solution (50 mL) and dichloromethane (50 mL). The organic phase was separated and the aqueous was extracted with dichloromethane (2×50 mL). The combined organic phases were dried (MgSO$_4$) then filtered and concentrated under reduced pressure. The residue was stirred with potassium carbonate (1 g, 7.2 mmol) in methanol (25 mL) at room temperature for 1 h. The mixture was treated with AMMONIUM CHLORIDE (1 g, 18.7 mmol) then concentrated under reduced pressure. The residue was partitioned between water (25 mL) and dichloromethane (25 mL) then separated. The aqueous phase was extracted with dichloromethane (25 mL) then dried (MgSO$_4$), filtered and concentrated under reduced pressure to yield (S)-6-(5-bromo-1-(trans-4-hydroxycyclohexyl)-1H-benzo[d]imidazol-2-yl) piperidin-2-one (1.9 g, 4.8 mmol, 79% yield) as a brown sticky foam. UPLC-MS: R$_t$ 0.83 min, m/z 392, 394 (M+H)$^+$.

Intermediate 14: (S)-6-(5-Bromo-1-(4,4-difluorocyclohexyl)-1H-benzo[d]imidazol-2-yl)piperidin-2-one

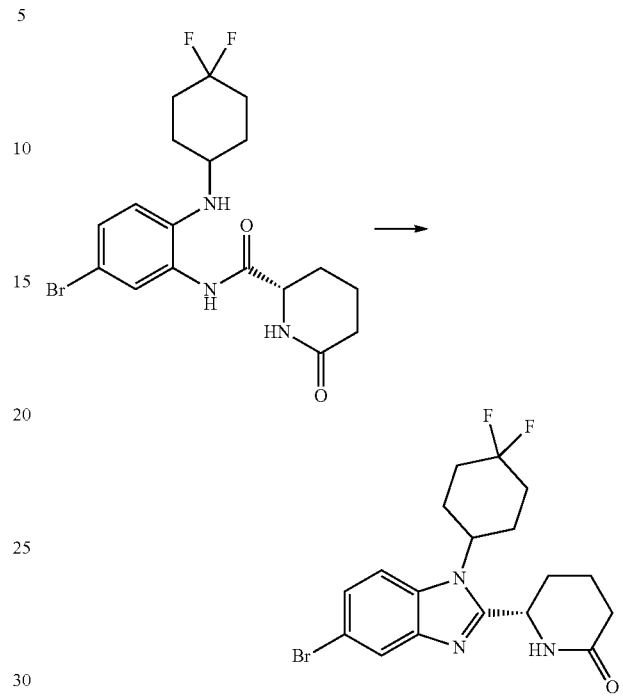

(S)—N-(5-bromo-2-((4,4-difluorocyclohexyl)amino) phenyl)-6-oxopiperidine-2-carboxamide (4.3 g, 9.9 mmol) was stirred in acetic acid (50 mL) at 50° C. for 5 days. The solvent was removed under reduced pressure then partitioned between saturated sodium hydrogen carbonate solution (50 mL) and dichloromethane (50 mL). The organic phase was separated and the aqueous was extracted with dichloromethane (2×50 mL). The combined organic phases were dried (MgSO$_4$) then filtered and concentrated under reduced pressure to yield (S)-6-(5-bromo-1-(4,4-difluorocyclohexyl)-1H-benzo[d]imidazol-2-yl)piperidin-2-one (3.3 g, 7.4 mmol, 75% yield) as a brown sticky foam. UPLC-MS: R$_t$ 1.25 min, m/z 412, 414 (M+H)$^+$.

Intermediate 15: (S)-6-(5-Bromo-1-(cis-4-hydroxy-4-methylcyclohexyl)-1H-benzo[d]imidazol-2-yl)piperidin-2-one

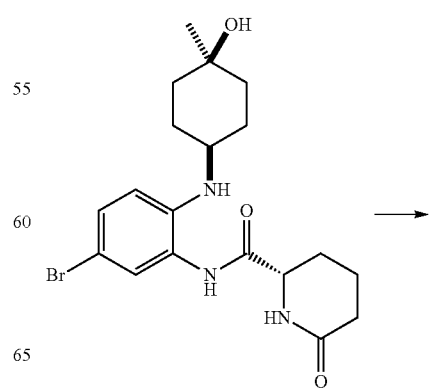

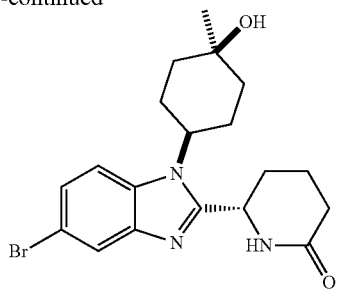

(S)—N-(5-bromo-2-((cis-4-hydroxy-4-methylcyclohexyl)amino)phenyl)-6-oxopiperidine-2-carboxamide (4.3 g, 10.03 mmol) was stirred in acetic acid (50 mL) at 50° C. for 5 days. The solvent was removed under reduced pressure then partitioned between saturated sodium hydrogen carbonate solution (50 mL) and dichloromethane (50 mL). The organic phase was separated and the aqueous was extracted with dichloromethane (2×50 mL). The combined organic phases were dried (MgSO$_4$) then filtered and concentrated under reduced pressure to yield (S)-6-(5-bromo-1-(cis-4-hydroxy-4-methylcyclohexyl)-1H-benzo[d]imidazol-2-yl)piperidin-2-one (4.0 g, 9.8 mmol, 97% yield) as a brown sticky foam. UPLC-MS: R$_t$ 0.87 min, m/z 406, 408 (M+H)$^+$.

Intermediate 16: (S)-6-(5-Bromo-1-((trans-4-methoxycyclohexyl)-1H-benzo[d]imidazol-2-yl)piperidin-2-one

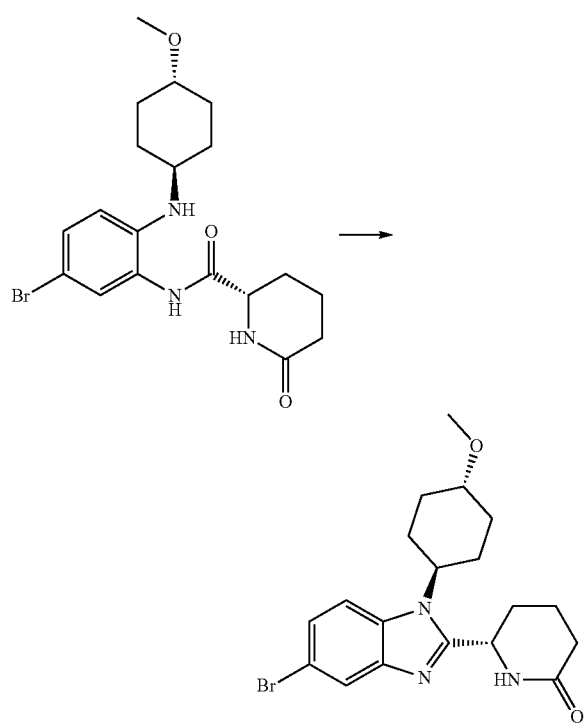

(S)—N-(5-bromo-2-((trans-4-methoxycyclohexyl)amino)phenyl)-6-oxopiperidine-2-carboxamide (4.2 g, 9.80 mmol) was stirred in acetic acid (50 mL) at 50° C. for 5 days. The solvent was removed under reduced pressure then partitioned between saturated sodium hydrogen carbonate solution (50 mL) and dichloromethane (50 mL). The organic phase was separated and the aqueous was extracted with dichloromethane (2×50 mL). The combined organic phases were dried (MgSO4) then filtered and concentrated under reduced pressure to yield (S)-6-(5-bromo-1-((trans-4-methoxycyclohexyl)-1H-benzo[d]imidazol-2-yl)piperidin-2-one (4.0 g, 9.6 mmol, 97% yield) as a brown sticky foam. UPLC-MS: R$_t$ 1.06 min, m/z 406, 408 (M+H)$^+$.

Intermediate 17: (S)-6-(5-Bromo-1-(trans-4-hydroxycyclohexyl)-1H-benzo[d]imidazol-2-yl)-1-(3,4-difluorophenyl)piperidin-2-one

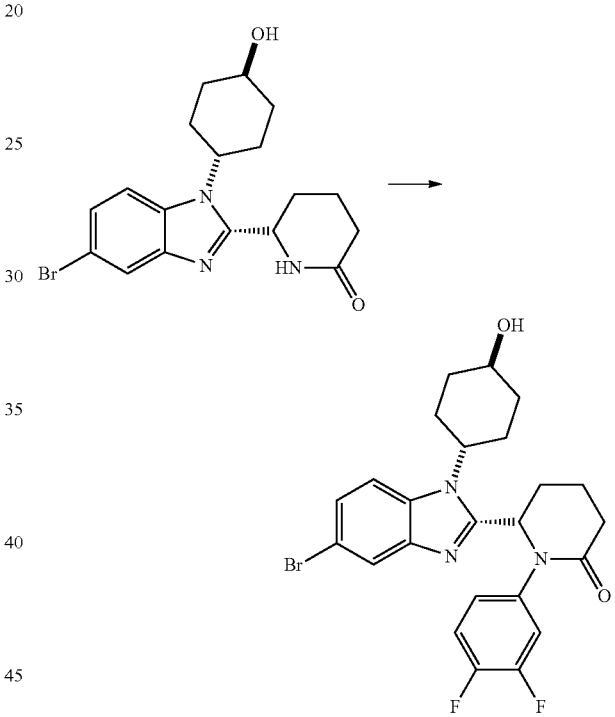

Copper(II) acetate monohydrate (300 mg, 1.50 mmol) was added to a stirred solution of (S)-6-(5-bromo-1-(trans-4-hydroxycyclohexyl)-1H-benzo[d]imidazol-2-yl)piperidin-2-one (500 mg, 1.26 mmol) and pyridine (1 mL, 12 mmol) in dichloromethane (50 mL). (3,4-difluorophenyl)boronic acid (700 mg, 4.43 mmol) was added and the mixture was stirred at room temperature for 5 h. The mixture was washed with water (50 mL) then with saturated brine (50 mL). The crude dichloromethane solution was loaded directly onto a silica gel column (12 g) then eluted with THF/DCM (0-50%) to yield an off white foam. The foam was triturated in tert-butyl methyl ether:isohexane (1:4, 10 mL) to yield (S)-6-(5-bromo-1-(trans-4-hydroxycyclohexyl)-1H-benzo[d]imidazol-2-yl)-1-(3,4-difluorophenyl)piperidin-2-one (400 mg, 0.79 mmol, 62% yield) as an off white solid. UPLC-MS: 1.23, m/z 504, 506 (M+H)$^+$.

Intermediate 18: (S)-6-(5-Bromo-1-(trans-4-hydroxycyclohexyl)-1H-benzo[d]imidazol-2-yl)-1-(3-chloro-4-fluorophenyl)piperidin-2-one Intermediate 19: (S)-6-(5-Bromo-1-(trans-4-hydroxycyclohexyl)-1H-benzo[d]imidazol-2-yl)-1-(3-fluoro-4-methoxyphenyl)piperidin-2-one

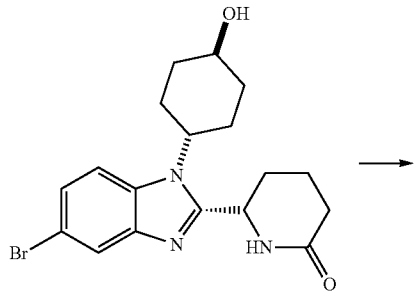

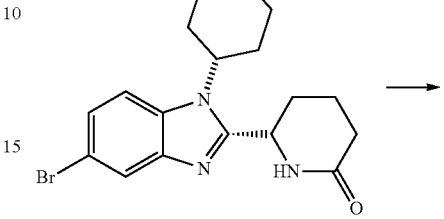

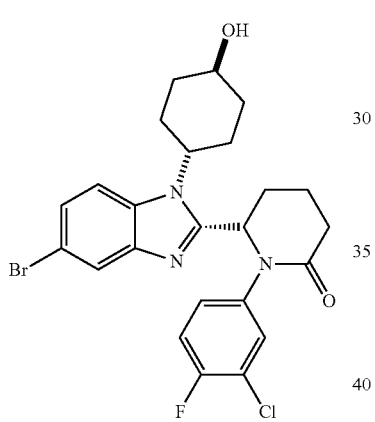

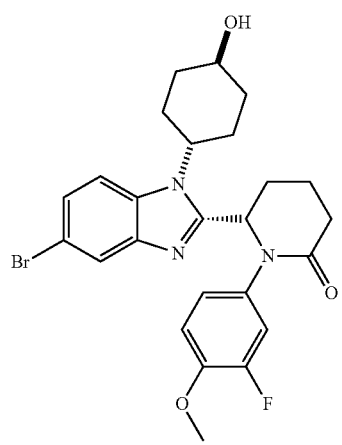

Copper(II) acetate monohydrate (300 mg, 1.50 mmol) was added to a stirred solution of (S)-6-(5-bromo-1-(trans-4-hydroxycyclohexyl)-1H-benzo[d]imidazol-2-yl)piperidin-2-one (500 mg, 1.26 mmol) and pyridine (1 mL, 12 mmol) in dichloromethane (50 mL). (3-chloro-4-fluorophenyl)boronic acid (700 mg, 4.01 mmol) was added and the mixture was stirred at room temperature for 5 h. The mixture was washed with water (50 mL) then with saturated brine (50 mL). The crude dichloromethane solution was loaded directly onto a silica gel column (12 g) then eluted with THF/DCM (0-50%) to yield an off white foam. The foam was triturated in tert-butyl methyl ether:isohexane (1:4, 10 mL) to yield (S)-6-(5-bromo-1-(trans-4-hydroxycyclohexyl)-1H-benzo[d]imidazol-2-yl)-1-(3-chloro-4-fluorophenyl)piperidin-2-one (420 mg, 0.798 mmol, 63.3% yield) as an off white solid. UPLC-MS: $R_t$ 1.28 min, m/z 520 for $^{35}Cl/^{79}Br$ (M+H)$^+$.

Copper(II) acetate monohydrate (300 mg, 1.50 mmol) was added to a stirred solution of (S)-6-(5-bromo-1-(trans-4-hydroxycyclohexyl)-1H-benzo[d]imidazol-2-yl)piperidin-2-one (500 mg, 1.26 mmol) and pyridine (1 mL, 12 mmol) in dichloromethane (50 mL). (3-fluoro-4-methoxyphenyl)boronic acid (700 mg, 4.12 mmol) was added and the mixture was stirred at room temperature for 5 h. The mixture was washed with water (50 mL) then with saturated brine (50 mL). The crude dichloromethane solution was loaded directly onto a silica gel column (12 g) then eluted with THF/DCM (0-50%) to yield an off white foam. The foam was triturated in tert-butyl methyl ether:isohexane (1:4, 10 mL) to yield (S)-6-(5-bromo-1-(trans-4-hydroxycyclohexyl)-1H-benzo[d]imidazol-2-yl)-1-(3-fluoro-4-methoxyphenyl)piperidin-2-one (400 mg, 0.77 mmol, 61% yield) as an off white solid. UPLC-MS: $R_t$ 1.16 min, m/z 516, 518 (M+H)$^+$.

Intermediate 20: (S)-6-(5-Bromo-1-(4,4-difluorocyclohexyl)-1H-benzo[d]imidazol-2-yl)-1-(3,4-difluorophenyl)piperidin-2-one

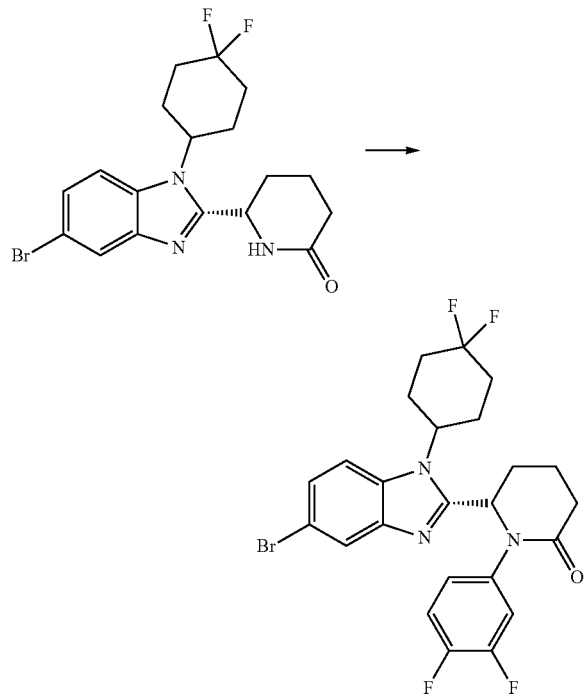

Copper(II) acetate monohydrate (300 mg, 1.50 mmol) was added to a stirred solution of (S)-6-(5-bromo-1-(4,4-difluorocyclohexyl)-1H-benzo[d]imidazol-2-yl)piperidin-2-one (500 mg, 1.13 mmol) and pyridine (1 mL, 12 mmol) in dichloromethane (50 mL). (3,4-difluorophenyl)boronic acid (700 mg, 4.43 mmol) was added and the mixture was stirred at room temperature for 5 h. The mixture was washed with water (50 mL) then with saturated brine (50 mL). The crude dichloromethane solution was loaded directly onto a silica gel column (12 g) then eluted with THF/DCM (0-50%) to yield an off white foam. The foam was triturated in tert-butyl methyl ether:isohexane (1:4, 10 mL) to yield (S)-6-(5-bromo-1-(4,4-difluorocyclohexyl)-1H-benzo[d]imidazol-2-yl)-1-(3,4-difluorophenyl)piperidin-2-one (460 mg, 0.81 mmol, 72% yield) as an off white solid. UPLC-MS: $R_t$ 1.63 min, m/z 524, 526 (M+H)$^+$.

Intermediate 21: (S)-6-(5-Bromo-1-(4,4-difluorocyclohexyl)-1H-benzo[d]imidazol-2-yl)-1-(3-fluoro-4-methoxyphenyl)piperidin-2-one

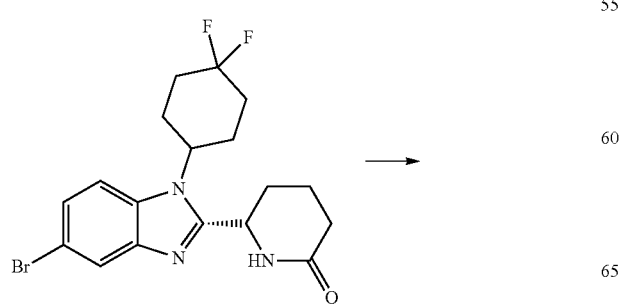

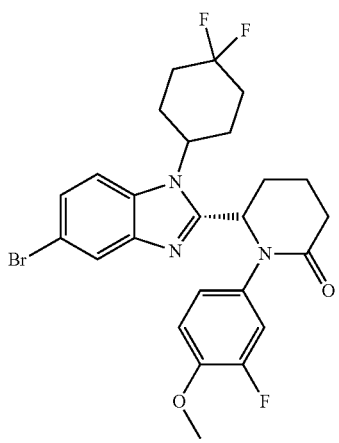

Copper(II) acetate monohydrate (300 mg, 1.50 mmol) was added to a stirred solution of (S)-6-(5-bromo-1-(4,4-difluorocyclohexyl)-1H-benzo[d]imidazol-2-yl)piperidin-2-one (500 mg, 1.13 mmol) and pyridine (1 mL, 12 mmol) in dichloromethane (50 mL). (3-fluoro-4-methoxyphenyl)boronic acid (700 mg, 4.12 mmol) was added and the mixture was stirred at room temperature for 5 h. The mixture was washed with water (50 mL) then with saturated brine (50 mL). The crude dichloromethane solution was loaded directly onto a silica gel column (12 g) then eluted with THF/DCM (0-50%) to yield an off white foam. The foam was triturated in tert-butyl methyl ether:isohexane (1:4, 10 mL) to yield (S)-6-(5-bromo-1-(4,4-difluorocyclohexyl)-1H-benzo[d]imidazol-2-yl)-1-(3-fluoro-4-methoxyphenyl)piperidin-2-one (480 mg, 0.89 mmol, 79% yield) as an off white solid. UPLC-MS: $R_t$ 1.56 min, m/z 536, 538 (M+H)$^+$.

Intermediate 22: (S)-6-(5-Bromo-1-(cis-4-hydroxy-4-methylcyclohexyl)-1H-benzo[d]imidazol-2-yl)-1-(3,4-difluorophenyl)piperidin-2-one

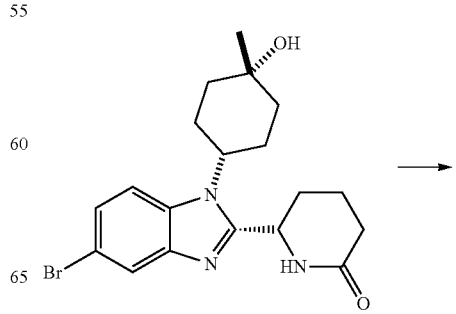

-continued

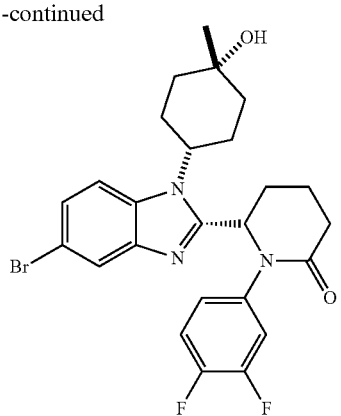

Copper(II) acetate monohydrate (300 mg, 1.50 mmol) was added to a stirred solution of (S)-6-(5-bromo-1-(cis-4-hydroxy-4-methylcyclohexyl)-1H-benzo[d]imidazol-2-yl)piperidin-2-one (500 mg, 1.22 mmol) and pyridine (1 mL, 12 mmol) in dichloromethane (50 mL). (3,4-difluorophenyl)boronic acid (700 mg, 4.43 mmol) was added and the mixture was stirred at room temperature for 5 h. The mixture was washed with water (50 mL) then with saturated brine (50 mL). The crude dichloromethane solution was loaded directly onto a silica gel column (12 g) then eluted with THF/DCM (0-50%) to yield an off white foam. The foam was triturated in tert-butyl methyl ether:isohexane (1:4, 10 mL) to yield (S)-6-(5-bromo-1-(cis-4-hydroxy-4-methylcyclohexyl)-1H-benzo[d]imidazol-2-yl)-1-(3,4-difluorophenyl)piperidin-2-one (510 mg, 0.974 mmol, 80% yield) as an off white solid. UPLC-MS: $R_t$ 1.31 min, m/z 518, 520 (M+H)$^+$.

Intermediate 23: (S)-6-(5-Bromo-1-(cis-4-hydroxy-4-methylcyclohexyl)-1H-benzo[d]imidazol-2-yl)-1-(3-chloro-4-fluorophenyl)piperidin-2-one

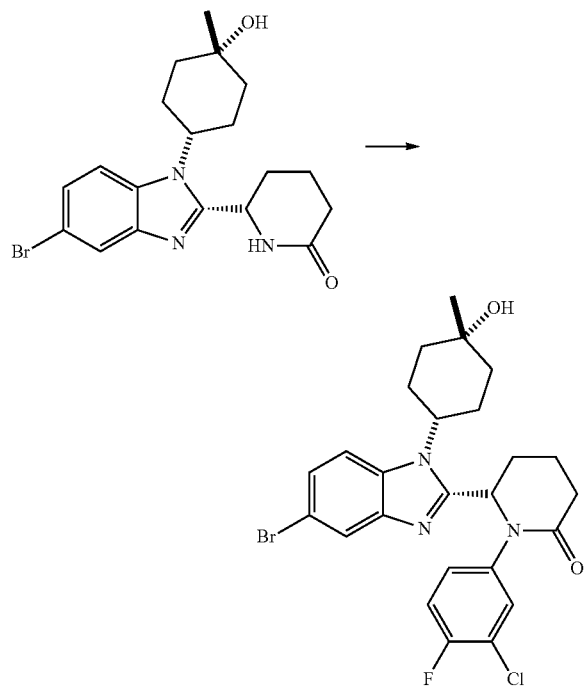

Copper(II) acetate monohydrate (300 mg, 1.50 mmol) was added to a stirred solution of (S)-6-(5-bromo-1-(cis-4-hydroxy-4-methylcyclohexyl)-1H-benzo[d]imidazol-2-yl)piperidin-2-one (500 mg, 1.218 mmol) and pyridine (1 mL, 12 mmol) in dichloromethane (50 mL). (3-chloro-4-fluorophenyl)boronic acid (700 mg, 4.01 mmol) was added and the mixture was stirred at room temperature for 5 h. The mixture was washed with water (50 mL) then with saturated brine (50 mL). The crude dichloromethane solution was loaded directly onto a silica gel column (12 g) then eluted with THF/DCM (0-50%) to yield an off white foam. The foam was triturated in tert-butyl methyl ether:isohexane (1:4, 10 mL) to yield (S)-6-(5-bromo-1-(cis-4-hydroxy-4-methylcyclohexyl)-1H-benzo[d]imidazol-2-yl)-1-(3-chloro-4-fluorophenyl)piperidin-2-one (630 mg, 1.17 mmol, 96% yield) as an off white solid. UPLC-MS: Rt 1.37 min, m/z 534 for $^{35}$Cl/$^{79}$Br (M+H)$^+$.

Intermediate 24: (S)-6-(5-Bromo-1-(cis-4-hydroxy-4-methylcyclohexyl)-1H-benzo[d]imidazol-2-yl)-1-(3-fluoro-4-methoxyphenyl)piperidin-2-one

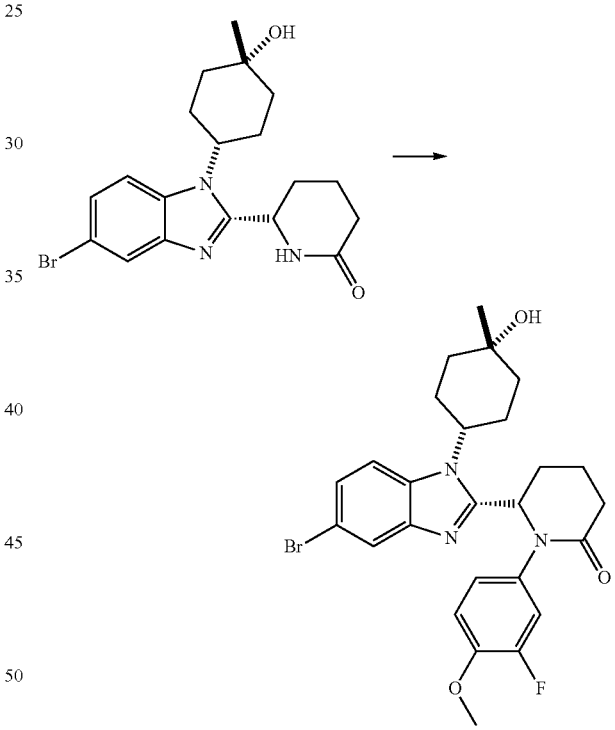

Copper(II) acetate monohydrate (300 mg, 1.50 mmol) was added to a stirred solution of (S)-6-(5-bromo-1-(cis-4-hydroxy-4-methylcyclohexyl)-1H-benzo[d]imidazol-2-yl)piperidin-2-one (500 mg, 1.22 mmol) and pyridine (1 mL, 12 mmol) in dichloromethane (50 mL). (3-fluoro-4-methoxyphenyl)boronic acid (700 mg, 4.12 mmol) was added and the mixture was stirred at room temperature for 5 h. The mixture was washed with water (50 mL) then with saturated brine (50 mL). The crude dichloromethane solution was loaded directly onto a silica gel column (12 g) then eluted with THF/DCM (0-50%) to yield an off white foam. The foam was triturated in tert-butyl methyl ether:isohexane (1:4, 10 mL) to yield (S)-6-(5-bromo-1-(cis-4-hydroxy-4-methylcyclohexyl)-1H-benzo[d]imidazol-2-yl)-1-(3-fluoro- 4-ethoxyphenyl)piperidin-2-one (570 mg, 1.064 mmol, 87% yield) as an off white solid. UPLC-MS: Rt 1.23 min, m/z 530, 532 (M+H)⁺.

Intermediate 25: (S)-6-(5-Bromo-1-(trans-4-methoxycyclohexyl)-1H-benzo[d]imidazol-2-yl)-1-(3,4-difluorophenyl)piperidin-2-one Intermediate 26: (S)-6-(5-Bromo-1-(trans-4-methoxycyclohexyl)-1H-benzo[d]imidazol-2-yl)-1-(3-fluoro-4-methoxyphenyl)piperidin-2-one

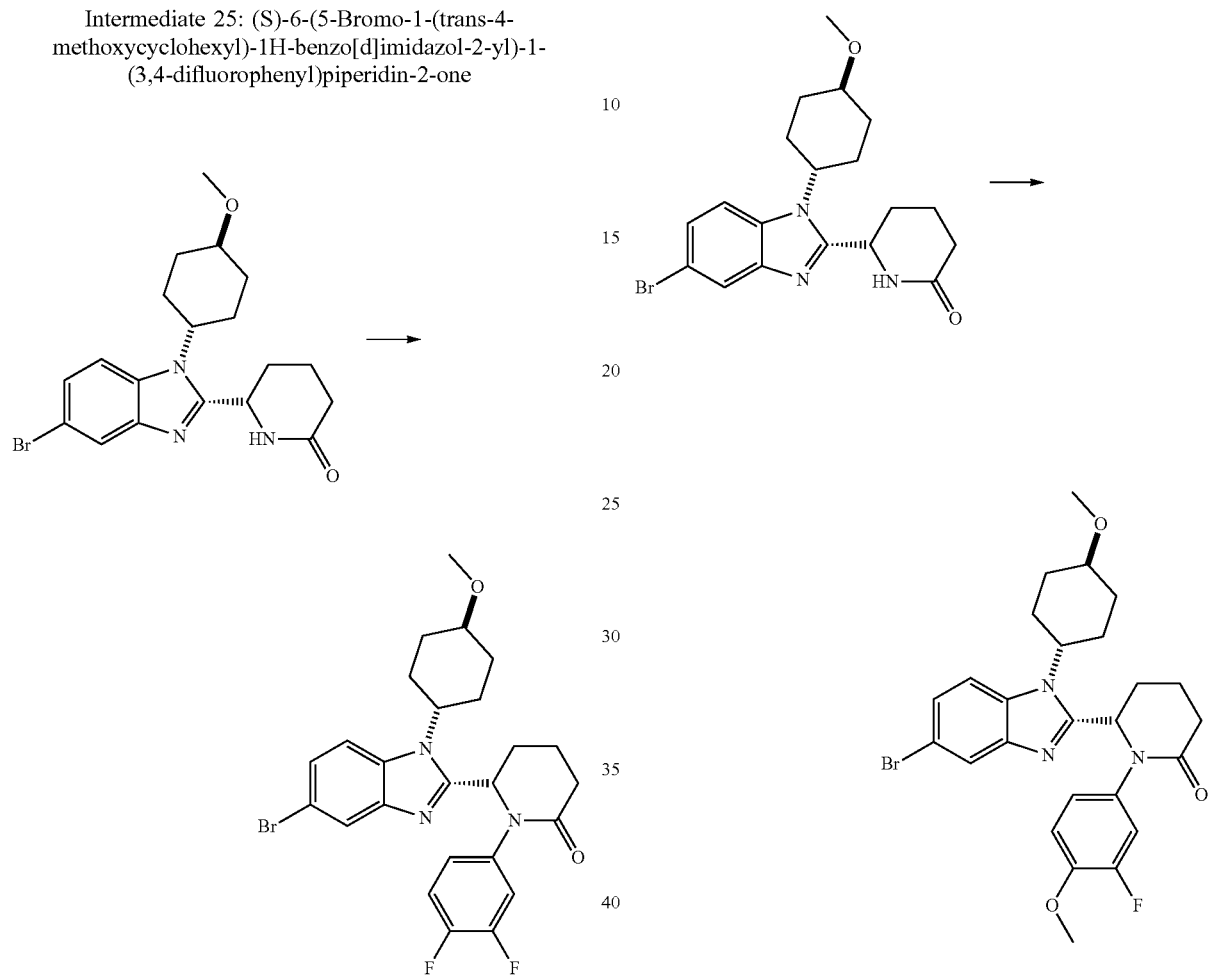

Copper(II) Acetate monohydrate (300 mg, 1.50 mmol) was added to a stirred solution of (S)-6-(5-bromo-1-(trans-4-methoxycyclohexyl)-1H-benzo[d]imidazol-2-yl)piperidin-2-one (500 mg, 1.19 mmol) and pyridine (1 mL, 12.36 mmol) in dichloromethane (50 mL). (3,4-difluorophenyl)boronic acid (700 mg, 4.43 mmol) was added and the mixture was stirred at room temperature for 5 h. The mixture was washed with water (50 mL) then with saturated brine (50 mL). The crude dichloromethane solution was loaded directly onto a silica gel column (12 g) then eluted with THF/DCM (0-50%) to yield an off white foam. The foam was triturated in tert-butylmethyl ether/isohexane (1:4, 10 mL) to yield (S)-6-(5-bromo-1-(trans-4-methoxycyclohexyl)-1H-benzo[d]imidazol-2-yl)-1-(3,4-difluorophenyl)piperidin-2-one (500 mg, 0.955 mmol, 80% yield) as an off white solid. UPLC-MS: Rt 1.49 min, m/z 518, 520 (M+H)⁺.

Copper(II) acetate monohydrate (300 mg, 1.50 mmol) was added to a stirred solution of (S)-6-(5-bromo-1-(trans-4-methoxycyclohexyl)-1H-benzo[d]imidazol-2-yl)piperidin-2-one (500 mg, 1.19 mmol) and pyridine (1.0 mL, 12 mmol) in dichloromethane (50 mL). (3-fluoro-4-methoxyphenyl)boronic acid (700 mg, 4.12 mmol) was added and the mixture was stirred at room temperature for 5 h. The mixture was washed with water (50 mL) then with saturated brine (50 mL). The crude dichloromethane solution was loaded directly onto a silica gel column (12 g) then eluted with THF/DCM (0-50%) to yield an off white foam. The foam was triturated in tert-butyl methyl ether:isohexane (1:4, 10 mL) to yield (S)-6-(5-bromo-1-(trans-4-methoxycyclohexyl)-1H-benzo[d]imidazol-2-yl)-1-(3-fluoro-4-methoxyphenyl)piperidin-2-one (570 mg, 1.06 mmol, 89% yield) as an off white solid. UPLC-MS: $R_t$ 1.41 min, m/z 530, 532 (M+H)⁺.

Compound Examples 7-22

Compound 10

(S)-1-(3,4-difluorophenyl)-6-(5-(1,4-dimethyl-1H-1,2,3-triazol-5-yl)-1-(trans-4-hydroxycyclohexyl)-1H-benzo[d]imidazol-2-yl)piperidin-2-one

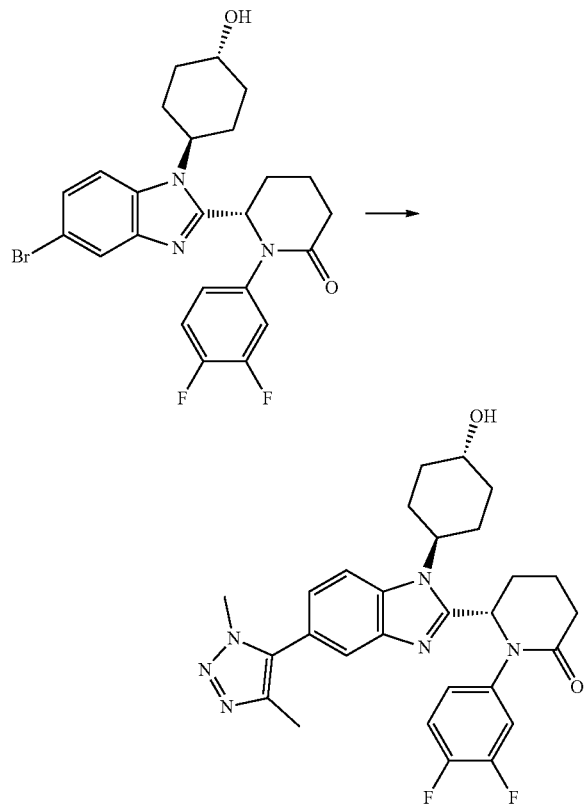

A vessel containing (S)-6-(5-bromo-1-(trans-4-hydroxycyclohexyl)-1H-benzo[d]imidazol-2-yl)-1-(3,4-difluorophenyl)piperidin-2-one (intermediate 17, 50 mg, 0.10 mmol), 1,4-dimethyl-1H-1,2,3-triazole (15 mg, 0.15 mmol), potassium acetate (50 mg, 0.51 mmol) and tert-amyl alcohol (0.75 mL) was evacuated then backfilled with nitrogen three times. cataCXium® A Pd G3 (7 mg, 10 µmol) was added and the mixture was heated to 100° C. for 18 h. The mixture was diluted with water (8 mL) then extracted with dichloromethane (3×8 mL). The combined organic phases were concentrated under reduced pressure to give the crude product. The crude product was purified by chromatography on silica gel (4 g column, 50-100% MeAc/isohexane) to afford a pale brown gum. The gum was triturated in tert-butyl methyl ether to yield (S)-1-(3,4-difluorophenyl)-6-(5-(1,4-dimethyl-1H-1,2,3-triazol-5-yl)-1-(trans-4-hydroxycyclohexyl)-1H-benzo[d]imidazol-2-yl)piperidin-2-one (26 mg, 0.047 mmol, 48% yield) as a tan solid. LCMS (method 1): Rt 1.50 min, m/z 521 (M+H)$^+$. 1H NMR (DMSO-d$_6$) δ 7.91-7.77 (m, 2H), 7.44-7.36 (m, 1H), 7.36-7.29 (m, 1H), 7.23 (dd, J=8.5, 1.7 Hz, 1H), 7.09-7.00 (m, 1H), 5.79 (t, J=4.6 Hz, 1H), 4.71 (d, J=4.1 Hz, 1H), 4.41-4.26 (m, 1H), 3.94 (s, 3H), 3.73-3.61 (m, 1H), 2.55 (dt, J=9.8, 6.2 Hz, 2H), 2.48-2.24 (m, 2H), 2.23 (s, 3H), 2.21-2.12 (m, 1H), 2.08-1.91 (m, 3H), 1.91-1.70 (m, 3H), 1.50-1.35 (m, 2H), 1.25-1.15 (m, 1H).

Compound 14

(S)-6-(1-(4,4-difluorocyclohexyl)-5-(1,4-dimethyl-1H-1,2,3-triazol-5-yl)-1H-benzo[d]imidazol-2-yl)-1-(3,4-difluorophenyl)piperidin-2-one

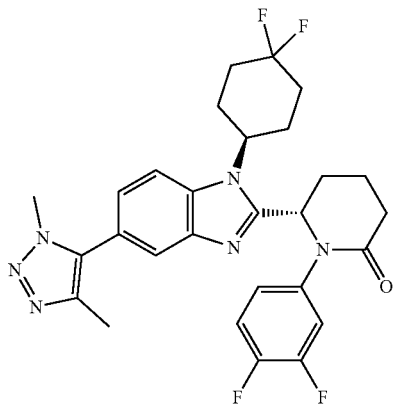

Compound 14 was synthesised using a procedure similar to compound 10 from intermediate 20. 31 mg of tan solid (57%). LCMS (method 1): R$_t$ 2.03 min, m/z 541 (M+H)$^+$. 1H NMR (DMSO-d$_6$) δ 7.88 (d, J=1.6 Hz, 1H), 7.61 (d, J=8.5 Hz, 1H), 7.40-7.28 (m, 3H), 7.09-7.01 (m, 1H), 5.75 (t, J=4.5 Hz, 1H), 4.77-4.60 (m, 1H), 3.94 (s, 3H), 2.65-2.52 (m, 2H), 2.49-2.25 (m, 4H), 2.23 (s, 3H), 2.21-2.05 (m, 5H), 2.03-1.92 (m, 2H), 1.84-1.73 (m, 1H).

Compound 7

(S)-1-(3-chloro-4-fluorophenyl)-6-(5-(1,4-dimethyl-1H-1,2,3-triazol-5-yl)-1-((trans)-4-hydroxycyclohexyl)-1H-benzo[d]imidazol-2-yl)piperidin-2-one

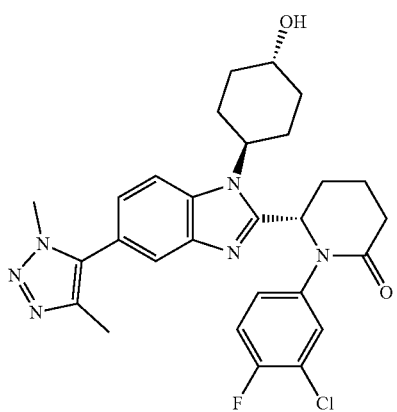 [SMILES: Cc1nnn(C)c1-c1ccc2c(c1)nc([C@@H]1CCCC(=O)N1c1ccc(F)c(Cl)c1)n2[C@H]1CC[C@H](O)CC1]

Compound 7 was synthesised using a procedure similar to compound 10 from intermediate 18. 20 mg of tan solid (25%). LCMS (method 1): R$_t$ 1.56 min, m/z 537 for $^{35}$Cl (M+H)$^+$. 1H NMR (DMSO-d$_6$) δ 7.90-7.80 (m, 2H), 7.57 (dd, J=6.9, 2.5 Hz, 1H), 7.30 (t, J=9.1 Hz, 1H), 7.22 (dd, J=8.4, 1.7 Hz, 1H), 7.18 (ddd, J=8.9, 4.4, 2.5 Hz, 1H), 5.81 (t, J=4.8 Hz, 1H), 4.71 (d, J=4.1 Hz, 1H), 4.35 (t, J=12.3 Hz, 1H), 3.93 (s, 3H), 3.74-3.59 (m, 1H), 2.64-2.51 (m, 2H), 2.45-2.25 (m, 2H), 2.23 (s, 3H), 2.17 (dd, J=12.7, 3.4 Hz, 1H), 2.09-1.91 (m, 3H), 1.90-1.71 (m, 3H), 1.43 (q, J=10.7, 10.2 Hz, 2H), 1.26-1.15 (m, 1H).

Compound 8

(S)-1-(3,4-difluorophenyl)-6-(5-(1,4-dimethyl-1H-1,2,3-triazol-5-yl)-1-(cis-4-hydroxy-4-methylcyclohexyl)-1H-benzo[d]imidazol-2-yl)piperidin-2-one

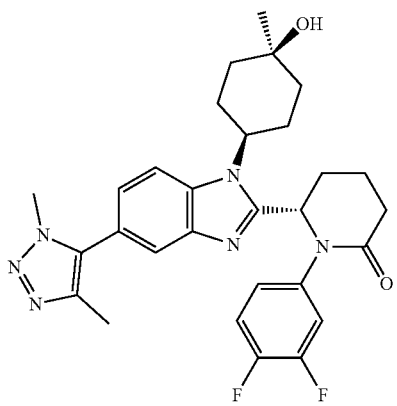 [SMILES: Cc1nnn(C)c1-c1ccc2c(c1)nc([C@@H]1CCCC(=O)N1c1ccc(F)c(F)c1)n2[C@H]1CC[C@@](C)(O)CC1]

Compound 8 was synthesised using a procedure similar to compound 10 from intermediate 18. 19 mg of tan solid (24%). LCMS (method 1): $R_t$ 1.66 min, m/z 535 (M+H)$^+$. 1H NMR (DMSO-d$_6$) δ 7.85 (d, J=1.6 Hz, 1H), 7.76 (d, J=8.5 Hz, 1H), 7.41-7.28 (m, 3H), 7.09-7.01 (m, 1H), 5.79-5.72 (m, 1H), 4.42 (s, 1H), 4.41-4.31 (m, 1H), 3.95 (s, 3H), 2.64-2.51 (m, 3H), 2.49-2.33 (m, 3H), 2.24 (s, 3H), 2.08-1.91 (m, 2H), 1.86-1.65 (m, 2H), 1.65-1.43 (m, 4H), 1.19 (s, 3H).

Compound 9

(S)-1-(3-chloro-4-fluorophenyl)-6-(5-(1,4-dimethyl-1H-1,2,3-triazol-5-yl)-1-(cis-4-hydroxy-4-methylcyclohexyl)-1H-benzo[d]imidazol-2-yl)piperidin-2-one

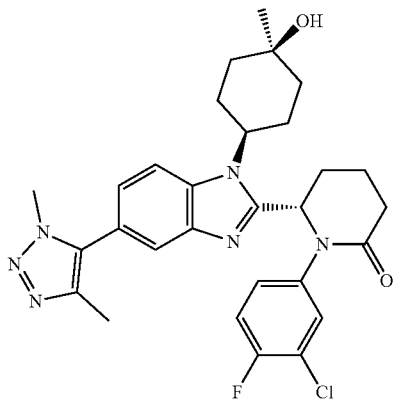 [SMILES: Cc1nnn(C)c1-c1ccc2c(c1)nc([C@@H]1CCCC(=O)N1c1ccc(F)c(Cl)c1)n2[C@H]1CC[C@@](C)(O)CC1]

Compound 9 was synthesised using a procedure similar to compound 10 from intermediate 23. 25 mg of tan solid (31%). LCMS (method 1): $R_t$ 1.74 min, m/z 551 for $^{35}$Cl (M+H)$^+$. 1H NMR (DMSO-d$_6$) δ 7.85 (d, J=1.5 Hz, 1H), 7.75 (d, J=8.5 Hz, 1H), 7.55 (dd, J=6.9, 2.5 Hz, 1H), 7.36-7.26 (m, 2H), 7.18 (ddd, J=8.9, 4.5, 2.5 Hz, 1H), 5.78 (t, J=4.7 Hz, 1H), 4.42 (s, 1H), 4.41-4.31 (m, 1H), 3.95 (s, 3H), 2.65-2.51 (m, 3H), 2.49-2.34 (m, 3H), 2.24 (s, 3H), 2.10-1.91 (m, 2H), 1.87-1.74 (m, 1H), 1.74-1.66 (m, 1H), 1.65-1.47 (m, 4H), 1.19 (s, 3H).

Compound 11

(S)-6-(1-(4,4-difluorocyclohexyl)-5-(1,4-dimethyl-1H-1,2,3-triazol-5-yl)-1H-benzo[d]imidazol-2-yl)-1-(3-fluoro-4-methoxyphenyl)piperidin-2-one

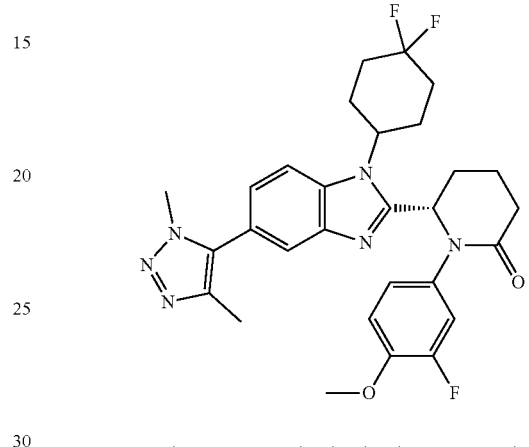

Compound 11 was synthesised using a procedure similar to compound 10 from intermediate 21. 34 mg of tan solid (42%). LCMS (method 1): $R_t$ 1.95 min, m/z 553 (M+H)$^+$. 1H NMR (DMSO-d$_6$) δ 7.88 (d, J=1.6 Hz, 1H), 7.59 (d, J=8.5 Hz, 1H), 7.30 (dd, J=8.4, 1.7 Hz, 1H), 7.10 (dd, J=12.7, 2.4 Hz, 1H), 7.05 (t, J=9.2 Hz, 1H), 6.95 (ddd, J=8.8, 2.4, 1.2 Hz, 1H), 5.71 (t, J=4.7 Hz, 1H), 4.75-4.60 (m, 1H), 3.94 (s, 3H), 3.74 (s, 3H), 2.65-2.51 (m, 2H), 2.48-2.25 (m, 4H), 2.23 (s, 3H), 2.22-2.00 (m, 5H), 1.97 (t, J=9.4 Hz, 1H), 1.85-1.73 (m, 1H), 1.32-1.19 (m, 1H).

Compound 12

(S)-1-(3,4-difluorophenyl)-6-(5-(1,4-dimethyl-1H-1,2,3-triazol-5-yl)-1-(trans-4-methoxycyclohexyl)-1H-benzo[d]imidazol-2-yl)piperidin-2-one

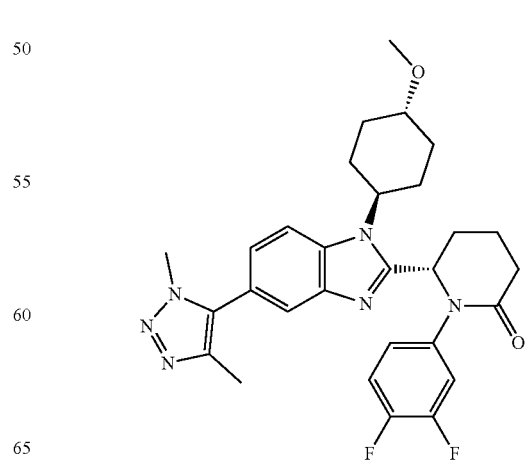

Compound 12 was synthesised using a procedure similar to compound 10 from intermediate 25. 37 mg of tan solid (46%). LCMS (method 1): R$_t$ 1.83 min, m/z 535 (M+H)$^+$. 1H NMR (DMSO-d$_6$) δ 7.88 (d, J=8.5 Hz, 1H), 7.84 (d, J=1.6 Hz, 1H), 7.42-7.30 (m, 2H), 7.24 (dd, J=8.5, 1.7 Hz, 1H), 7.06 (ddd, J=9.0, 3.8, 2.0 Hz, 1H), 5.80 (t, J=4.6 Hz, 1H), 4.46-4.35 (m, 1H), 3.95 (s, 3H), 3.47-3.36 (m, 1H), 3.29 (s, 3H), 2.65-2.52 (m, 2H), 2.45-2.26 (m, 2H), 2.24 (s, 3H), 2.22-2.11 (m, 2H), 2.10-1.94 (m, 2H), 1.83 (d, J=16.0 Hz, 2H), 1.46-1.32 (m, 2H), 1.32-1.22 (m, 1H).

Compound 13

(S)-6-(5-(1,4-dimethyl-1H-1,2,3-triazol-5-yl)-1-(trans-4-methoxycyclohexyl)-1H-benzo[d]imidazol-2-yl)-1-(3-fluoro-4-methoxyphenyl)piperidin-2-one

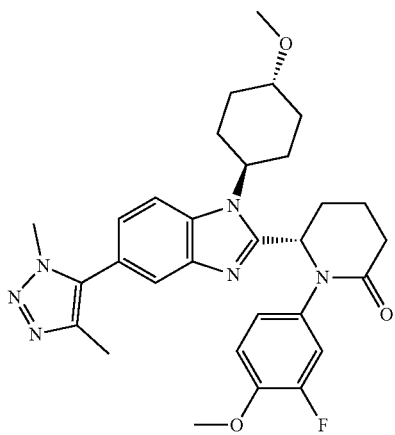

Compound 13 was synthesised using a procedure similar to compound 10 from intermediate 26. 27 mg of tan solid (34%). LCMS (method 1): R$_t$ 1.73 min, m/z 547 (M+H)$^+$. 1H NMR (DMSO-d$_6$) δ 7.92-7.79 (m, 2H), 7.23 (dd, J=8.5, 1.8 Hz, 1H), 7.12 (dd, J=12.7, 2.4 Hz, 1H), 7.03 (t, J=9.1 Hz, 1H), 6.96 (ddd, J=8.8, 2.4, 1.1 Hz, 1H), 5.80-5.67 (m, 1H), 4.45-4.32 (m, 1H), 3.94 (s, 3H), 3.74 (s, 3H), 3.46-3.34 (m, 1H), 3.28 (s, 3H), 2.56 (dq, J=17.9, 6.8, 5.9 Hz, 2H), 2.33 (dt, J=27.7, 11.0 Hz, 2H), 2.23 (s, 3H), 2.19-1.96 (m, 6H), 1.80 (s, 2H), 1.46-1.28 (m, 2H).

Compound 15

(S)-1-(3,4-difluorophenyl)-6-(5-(1,4-dimethyl-1H-pyrazol-5-yl)-1-(trans-4-hydroxycyclohexyl)-1H-benzo[d]imidazol-2-yl)piperidin-2-one

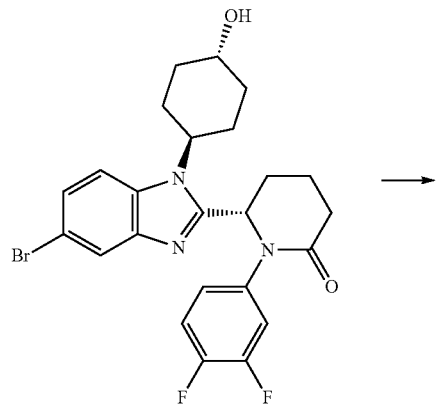

→

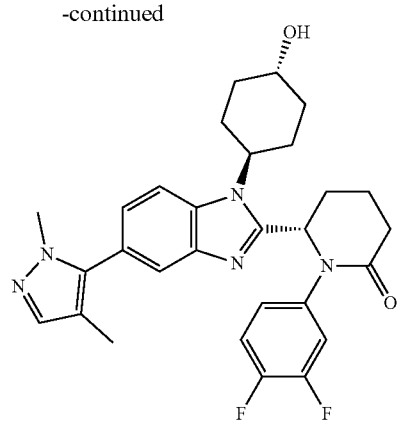

A tube containing (S)-6-(5-bromo-1-(trans-4-hydroxycyclohexyl)-1H-benzo[d]imidazol-2-yl)-1-(3,4-difluorophenyl)piperidin-2-one (intermediate 17, 100 mg, 0.20 mmol), 1,4-dimethyl-5-(4,4,5,5-tetramethyl-1,3,2-dioxaborolan-2-yl)-1H-pyrazole (50 mg, 0.23 mmol), potassium carbonate (80 mg, 0.58 mmol) and Pd(Ph$_3$P)$_4$ (20 mg, 0.017 mmol) was evacuated and backfilled with nitrogen three times. Water (1 mL) and 1,4-dioxane (2 mL) were added then the evacuate and backfill procedure was repeated three times. The mixture was heated to 85° C. with stirring for 2 h. The mixture was diluted with water (10 mL) then extracted with ethyl acetate (2×10 mL). The combined organic phases were concentrated under reduced pressure. The crude product was purified by flash chromatography (50-100% MeAc/isohexane) to afford a colourless gum which was triturated in tert-butyl methyl ether to afford (S)-1-(3,4-difluorophenyl)-6-(5-(1,4-dimethyl-1H-pyrazol-5-yl)-1-(trans-4-hydroxycyclohexyl)-1H-benzo[d]imidazol-2-yl)piperidin-2-one (27 mg, 0.049 mmol, 25% yield) as a white solid. LCMS (method 1): R$_t$ 1.65 min, m/z 520 (M+H)$^+$. 1H NMR (400 MHz, DMSO-d6) δ 7.81 (d, J=8.5 Hz, 1H), 7.70 (d, J=1.6 Hz, 1H), 7.44-7.29 (m, 3H), 7.16 (dd, J=8.5, 1.7 Hz, 1H), 7.08-7.02 (m, 1H), 5.78 (t, J=4.7 Hz, 1H), 4.71 (d, J=4.1 Hz, 1H), 4.41-4.26 (m, 1H), 3.71 (s, 3H), 3.69-3.60 (m, 1H), 2.65-2.51 (m, 2H), 2.45-2.34 (m, 1H), 2.31-2.12 (m, 2H), 2.08-1.97 (m, 2H), 1.96 (s, 3H), 1.92-1.72 (m, 3H), 1.50-1.34 (m, 2H), 1.26-1.15 (m, 1H).

Compound 16

(S)-1-(3,4-difluorophenyl)-6-(5-(1,4-dimethyl-1H-pyrazol-5-yl)-1-(cis-4-hydroxy-4-methylcyclohexyl)-1H-benzo[d]imidazol-2-yl)piperidin-2-one

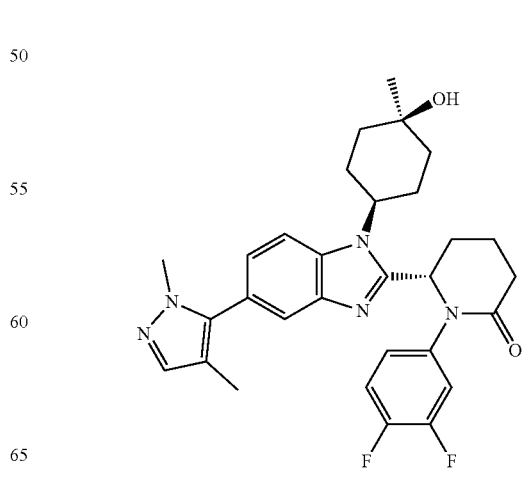

Compound 16 was synthesised using a procedure similar to compound 15 from intermediate 22. 15 mg of white solid (14%). LCMS (method 1): $R_t$ 1.81 min, m/z 534 (M+H)$^+$. 1H NMR (DMSO-d$_6$) δ 7.78-7.67 (m, 2H), 7.41-7.30 (m, 3H), 7.24 (dd, J=8.3, 1.7 Hz, 1H), 7.09-7.02 (m, 1H), 5.80-5.68 (m, 1H), 4.41 (s, 1H), 4.40-4.30 (m, 1H), 3.72 (s, 3H), 2.66-2.51 (m, 2H), 2.48-2.34 (m, 2H), 2.11-1.98 (m, 2H), 1.97 (s, 3H), 1.83-1.46 (m, 6H), 1.19 (s, 3H), 1.07-0.96 (m, 1H).

Compound 17

(S)-6-(1-(4,4-difluorocyclohexyl)-5-(1,4-dimethyl-1H-pyrazol-5-yl)-1H-benzo[d]imidazol-2-yl)-1-(3-fluoro-4-methoxyphenyl)piperidin-2-one

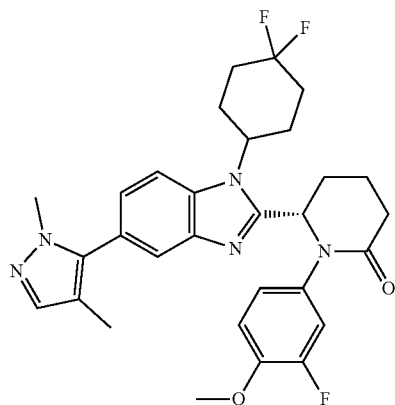 [SMILES: COc1ccc(N2C(=O)CCC[C@H]2c2nc3cc(-c4c(C)cnn4C)ccc3n2C2CCC(F)(F)CC2)cc1F]

Compound 17 was synthesised using a procedure similar to compound 15 from intermediate 21. 40 mg of white solid (39%). LCMS (method 1): $R_t$ 2.11 min, m/z 552 (M+H)$^+$. 1H NMR (DMSO-d$_6$) δ 7.75 (d, J=1.6 Hz, 1H), 7.56 (d, J=8.5 Hz, 1H), 7.32 (s, 1H), 7.23 (dd, J=8.4, 1.7 Hz, 1H), 7.10 (dd, J=12.7, 2.4 Hz, 1H), 7.05 (t, J=9.2 Hz, 1H), 6.95 (ddd, J=8.8, 2.5, 1.2 Hz, 1H), 5.70 (t, J=4.6 Hz, 1H), 4.75-4.57 (m, 1H), 3.74 (s, 3H), 3.72 (s, 3H), 2.63-2.52 (m, 2H), 2.45-1.88 (m, 10H), 1.97 (s, 3H), 1.84-1.74 (m, 1H), 1.31-1.19 (m, 1H).

Compound 18

(S)-6-(5-(1,4-dimethyl-1H-pyrazol-5-yl)-1-(trans-4-methoxycyclohexyl)-1H-benzo[d]imidazol-2-yl)-1-(3-fluoro-4-methoxyphenyl)piperidin-2-one

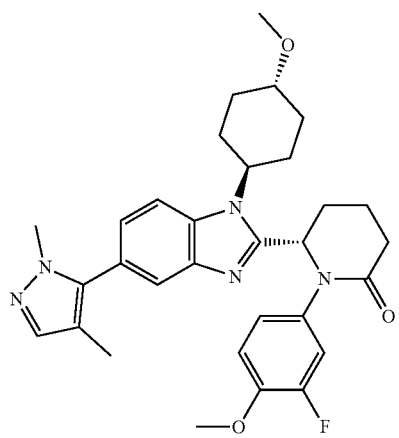

Compound 18 was synthesised using a procedure similar to compound 15 from intermediate 26. 67 mg of white solid (63%). LCMS (method 1): $R_t$ 1.91 min, m/z 546 (M+H)$^+$. 1H NMR (DMSO-d$_6$) δ 7.82 (d, J=8.5 Hz, 1H), 7.72 (d, J=1.6 Hz, 1H), 7.33 (s, 1H), 7.19-7.10 (m, 2H), 7.04 (t, J=9.1 Hz, 1H), 6.97 (ddd, J=8.8, 2.4, 1.1 Hz, 1H), 5.73 (t, J=4.7 Hz, 1H), 4.46-4.31 (m, 1H), 3.75 (s, 3H), 3.72 (s, 3H), 3.44-3.35 (m, 1H), 3.29 (s, 3H), 2.62-2.52 (m, 1H), 2.50-2.45 (m, 1H), 2.43-2.00 (m, 7H), 1.98 (s, 3H), 1.81 (s, 2H), 1.47-1.28 (m, 2H), 1.21-1.12 (m, 1H).

Compound 19

(S)-1-(3,4-difluorophenyl)-6-(5-(1,4-dimethyl-1H-imidazol-5-yl)-1-(trans-4-hydroxycyclohexyl)-1H-benzo[d]imidazol-2-yl)piperidin-2-one

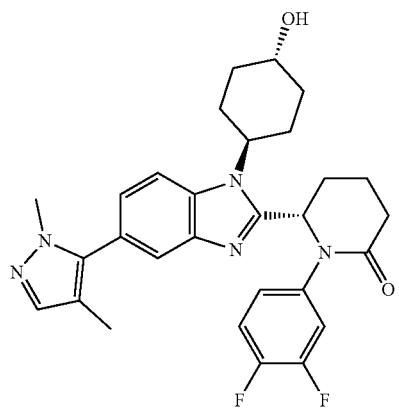 [SMILES: Cc1cnn(C)c1-c1ccc2c(c1)nc([C@@H]1CCCC(=O)N1c1ccc(F)c(F)c1)n2[C@H]1CC[C@H](O)CC1]

(S)-6-(5-bromo-1-(trans-4-hydroxycyclohexyl)-1H-benzo[d]imidazol-2-yl)-1-(3,4-difluorophenyl)piperidin-2-one (intermediate 17, 100 mg, 0.20 mmol), bis(pinacolato)diboron (55 mg, 0.22 mmol), potassium acetate (30 mg, 0.31 mmol) and PdCl$_2$(dppf) (15 mg, 0.021 mmol) were placed in a tube fitted with septum then evacuated and backfilled with nitrogen three times. 1,4-dioxane (3 mL) was added and the mixture was evacuated and backfilled with nitrogen a further three times. The mixture was heated to 80° C. for 1 h then cooled. 5-bromo-1,4-dimethyl-1H-imidazole (40 mg, 0.23 mmol), potassium carbonate (90 mg, 0.65 mmol), PdCl$_2$(dppf) (15 mg, 0.021 mmol) and water (1 mL) were added and the mixture was stirred at 80° C. for a further 1 h. The mixture was cooled, diluted with water (10 mL) and extracted with dichloromethane (3×10 mL) then the combined organic phases were concentrated under reduced pressure. The crude product was purified by flash chromatography (5-8% MeOH (with 2.5% NH$_3$)/DCM) to afford (S)-1-(3,4-difluorophenyl)-6-(5-(1,4-dimethyl-1H-imidazol-5-yl)-1-(trans-4-hydroxycyclohexyl)-1H-benzo[d]imidazol-2-yl)piperidin-2-one (52 mg, 0.093 mmol, 47% yield) as an off white solid. LCMS (method 1): $R_t$ 1.04 min, m/z 520 (M+H)$^+$. 1H NMR (DMSO-d$_6$) δ 7.76 (d, J=8.5 Hz, 1H), 7.65 (d, J=1.6 Hz, 1H), 7.55 (s, 1H), 7.43-7.28 (m, 2H), 7.13 (dd, J=8.5, 1.7 Hz, 1H), 7.10-6.97 (m, 1H), 5.76 (d, J=5.3 Hz, 1H), 4.81-4.62 (m, 1H), 4.43-4.17 (m, 1H), 3.71-3.61 (m, 1H), 3.52 (s, 3H), 2.65-2.52 (m, 1H), 2.44-2.32 (m, 1H), 2.32-2.12 (m, 2H), 2.09 (s, 3H), 2.07-1.91 (m, 3H), 1.90-1.67 (m, 3H), 1.49-1.35 (m, 2H), 1.23-1.13 (m, 1H).

Compound 20

(S)-1-(3,4-difluorophenyl)-6-(5-(1,4-dimethyl-1H-imidazol-5-yl)-1-(cis-4-hydroxy-4-methylcyclohexyl)-1H-benzo[d]imidazol-2-yl)piperidin-2-one

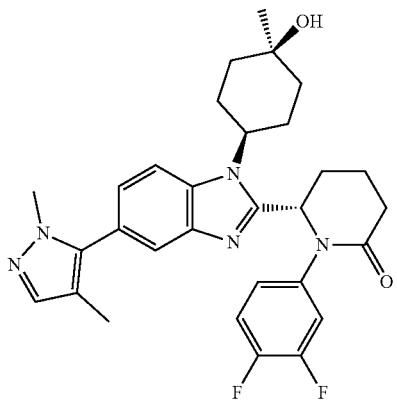 [SMILES: Cc1cnn(C)c1-c1ccc2c(c1)nc([C@@H]1CCCC(=O)N1c1ccc(F)c(F)c1)n2[C@H]1CC[C@@](C)(O)CC1]

Compound 20 was synthesised using a procedure similar to compound 19 from intermediate 26. 40 mg of off-white solid (37%). LCMS (method 1): $R_t$ 1.23 min, m/z 534 (M+H)$^+$. 1H NMR (400 MHz, DMSO-d$_6$) δ 7.76-7.63 (m, 2H), 7.55 (s, 1H), 7.46-7.27 (m, 2H), 7.20 (dd, J=8.5, 1.7 Hz, 1H), 7.12-6.98 (m, 1H), 5.75-5.70 (m, 1H), 4.41 (s, 1H), 4.39-4.26 (m, 1H), 3.53 (s, 3H), 2.65-2.51 (m, 3H), 2.47-2.30 (m, 2H), 2.10 (s, 3H), 2.07-1.92 (m, 2H), 1.83-1.73 (m, 1H), 1.74-1.65 (m, 1H), 1.64-1.43 (m, 4H), 1.18 (s, 3H), 1.01 (d, J=12.4 Hz, 1H).

Compound 21

(S)-6-(1-(4,4-difluorocyclohexyl)-5-(1,4-dimethyl-1H-imidazol-5-yl)-1H-benzo[d]imidazol-2-yl)-1-(3-fluoro-4-methoxyphenyl)piperidin-2-one

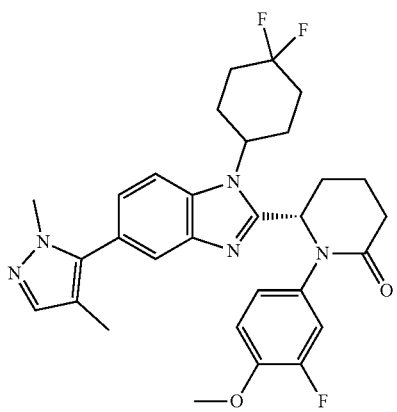 [SMILES: COc1ccc(N2C(=O)CCC[C@H]2c2nc3cc(-c4c(C)cnn4C)ccc3n2C2CCC(F)(F)CC2)cc1F]

Compound 21 was synthesised using a procedure similar to compound 19 from intermediate 26. 32 mg of tan solid (29%). LCMS (method 1): $R_t$ 1.43 min, m/z 552 (M+H)$^+$. 1H NMR (DMSO-d$_6$) δ 7.71 (d, J=1.6 Hz, 1H), 7.56 (s, 1H), 7.52 (d, J=8.5 Hz, 1H), 7.21 (dd, J=8.5, 1.7 Hz, 1H), 7.11 (dd, J=12.7, 2.4 Hz, 1H), 7.05 (t, J=9.2 Hz, 1H), 6.96 (ddd, J=8.8, 2.4, 1.2 Hz, 1H), 5.75-5.62 (m, 1H), 4.74-4.57 (m, 1H), 3.75 (s, 3H), 3.53 (s, 3H), 2.65-2.52 (m, 2H), 2.45-1.89 (m, 10H), 2.11 (s, 3H), 1.79 (d, J=12.4 Hz, 1H), 1.31-1.19 (m, 1H).

Compound 22

(S)-6-(5-(1,4-dimethyl-1H-imidazol-5-yl)-1-(trans-4-methoxycyclohexyl)-1H-benzo[d]imidazol-2-yl)-1-(3-fluoro-4-methoxyphenyl)piperidin-2-one

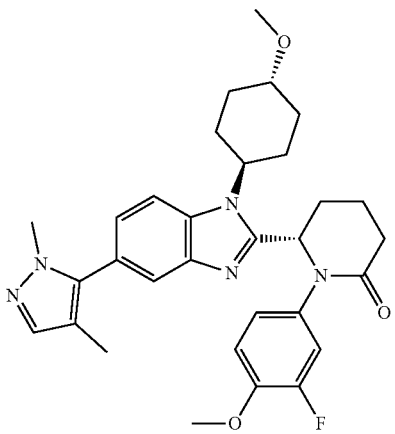 [SMILES: COc1ccc(N2C(=O)CCC[C@H]2c2nc3cc(-c4c(C)cnn4C)ccc3n2[C@H]2CC[C@H](OC)CC2)cc1F]

Compound 22 was synthesised using a procedure similar to compound 19 from intermediate 26. 24 mg of tan solid (22%). LCMS (method 1): $R_t$ 1.26 min, m/z 546 (M+H)$^+$. 1H NMR (DMSO-d$_6$) δ 7.76 (d, J=8.5 Hz, 1H), 7.66 (d, J=1.6 Hz, 1H), 7.55 (s, 1H), 7.14 (d, J=2.0 Hz, 1H), 7.11 (dd, J=4.6, 2.0 Hz, 1H), 7.03 (t, J=9.1 Hz, 1H), 6.99-6.92 (m, 1H), 5.71 (t, J=4.6 Hz, 1H), 4.48-4.26 (m, 1H), 3.74 (s, 3H), 3.52 (s, 3H), 3.42-3.33 (m, 2H), 3.28 (s, 3H), 2.63-2.51 (m, 1H), 2.46-2.11 (m, 4H), 2.10 (s, 3H), 2.09-1.98 (m, 3H), 1.87-1.72 (m, 2H), 1.45-1.22 (m, 2H), 1.19-1.11 (m, 1H).

Example 23: Biological Testing

Surface Plasmon Resonance (BIAcore) Analysis of Binding to EP300, CBP and BRD4 BD1

BIAcore data for compound binding to EP300 and BRD4 was acquired using a T200 BIAcore instrument at 4° C. His-tagged EP300 Bromodomain (1046-1163), His-tagged CBP Bromodomain (1081-1197) and BRD4 Bromodomain 1 (49-170) proteins were captured onto an NTA chip via a combined capture and amine coupling method. NTA groups were first chelated with 30 mM nickel chloride and then activated with 0.2 M N-ethyl-N'-(diethylaminopropyl)-carbodiimide (EDC) and 0.05 μM N-hydroxysuccimide (NHS).

Bromodomain proteins diluted to 9.6M in PBS 0.05% Tween-20 were injected at 10l/min and covalently bound. Ethanolamine injections were performed to cap unreacted moieties on the surface and remove uncoupled protein. A typical immobilisation resulted in ~2-4 kRU of protein immobilised on the surface.

Test compounds were serially diluted to generate 1, 10, 100, 1000 and 10000 nM solutions in running buffer (PBS with 0.005% Tween-20, 0.1% DMSO). Using a flow rate of 90 μL/min throughout, runs consisted of injections of compound with escalating concentration, interspersed with buffer blank runs consisting of 5 repeat injections of running buffer.

Sensorgrams were analyzed with BIAevaluation (GE Healthcare) using a 1:1 interaction model to generate $k_a$ and $k_d$ values to describe the kinetics of binding. $K_D$ values were derived from the quotient of $k_d$ and $k_a$. Compounds were tested twice against EP300, CBP and/or BRD4 bromodomain surfaces to obtain geometric means of the kinetic and affinity parameters. All compounds tested gave $K_D$ values in the range of 0.5-10,000 nM. For instance, against EP300 and CBP, compounds 7-22 gave $K_D$ values in the range of 1-200 nM.

Cell Viability Assay

The 22Rv1 cell line was obtained from ATCC (UK) and cultured according to the supplier's recommendations. Cell growth inhibitory activity of representative compounds was determined using the CellTiter-Glo® Luminescent Cell Viability Assay kit (Promega, USA).

22Rv1 cells were maintained in RPMI 1640 media containing 10% Foetal Bovine Serum, 2 mM Glutamine, 1 mM sodium pyruvate and 100 units of Penicillin-100 µg of Streptomycin. Cells were incubated at 37° C. in a humidified atmosphere with 95% O2 and 5% $CO_2$. 2000 cells were seeded per well in Poly-D-Lysine (PDL) coated 96-well black clear bottom plates (VWR, UK) in 50µ L of growth medium. After 48 hours, medium was removed and replaced with growth medium containing diluted test compounds. Compound dilutions were performed by serially diluting in half log intervals DMSO stocks at a maximum concentration of 10 mM, for a total of 7 dilutions. A 1 µl aliquot of each dilution point was added to 99 µl of growth medium and 50 µL added to each well containing cells, providing 100 µM compound at the maximum concentration point (1% DMSO). 1% DMSO treated cells served as a high control.

Cells were incubated for a further 72 hours at 37° C. and cell viability determined using the CellTiter-Glo® Luminescent Cell Viability Assay according to the manufacturer's instructions. Briefly, a volume of CellTiter-Glo® reagent equal to the volume of growth media was added to each well. Plates were shaken for approximately 2 minutes and incubated at room temperature (22° C.) for 10 minutes. The luminescence signal was measured using an Envision plate reader with an integration time of 1 second per well.

All data was normalised to the mean of 6 high-controls. The half maximum inhibitor concentration (IC50) was calculated from a 4-parameter logistic curve fit of the data using the Dotmatics software (UK). All compounds tested gave IC50 values in the range of 100 nM-100 µM, typically from 100 nM-30 µM.

Cell based assays are likely to show some variability due to the complexity of the system and it is understood that the results of these assays may vary as assay conditions are varied. Some level of cell growth inhibition is indicative of the compound having some inhibitory activity in specified cells, whereas lack of the inhibition below the highest concentration tested does not necessarily indicate the compound has no inhibitory activity on the cells.

Example 24: Tablet Composition

Tablets, each weighing 0.15 g and containing 25 mg of a compound of the invention are manufactured as follows:

Composition for 10,000 Tablets

| | |
|---|---|
| Compound of the invention (250 g) | |
| Lactose (800 g) | |
| Corn starch (415 g) | |
| Talc powder (30 g) | |
| Magnesium stearate (5 g) | |

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium is added, carefully mixed and processed into tablets.

Example 25: Injectable Formulation

| | |
|---|---|
| Compound of the invention | 200 mg |
| Hydrochloric Acid Solution 0.1M or Sodium Hydroxide Solution 0.1M q.s. | to pH 4.0 to 7.0 |
| Steriile water q.s. to | 10 mL |

The compound of the invention is dissolved in most of the water (35°-40° C.) and the pH adjusted to between 4.0 and 7.0 with the hydrochloric acid or the sodium hydroxide as appropriate. The batch is then made up to volume with water and filtered through a sterile micropore filter into a sterile 10 mL amber glass vial (type 1) and sealed with sterile closures and overseals.

Example 26: Intramuscular Injection

| | |
|---|---|
| Compound of the invention | 200 mg |
| Benzyl Alcohol | 0.10 g |
| Glycofurol 75 | 1.45 g |
| Water for injection q.s to | 3.00 mL |

The compound of the invention is dissolved in the glycofurol. The benzyl alcohol is then added and dissolved, and water added to 3 ml. The mixture is then filtered through a sterile micropore filter and sealed in sterile 3 ml glass vials (type 1).

Example 27: Syrup Formulation

| | |
|---|---|
| Compound of invention | 250 mg |
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

The compound of the invention is dissolved in a mixture of the glycerol and most of the purified water. An aqueous solution of the sodium benzoate is then added to the solution, followed by addition of the sorbitol solution and finally the flavour. The volume is made up with purified water and mixed well.

The invention claimed is:

1. A compound which is a benzimidazole of formula (I):

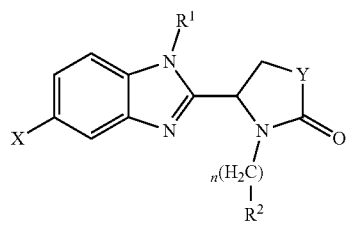
(I)

wherein:

X is a 5-membered heteroaryl group selected from the following:

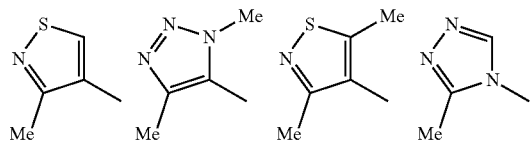

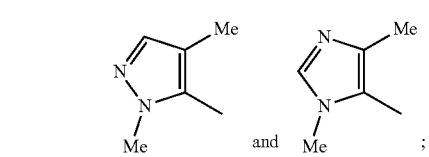

R¹ is a group which is unsubstituted or substituted and is selected from C-linked 4- to 6-membered heterocyclyl; $C_3$-$C_6$ cycloalkyl; $C_1$-$C_6$ alkyl which is unsubstituted or substituted by $C_6$-$C_{10}$ aryl, 5- to 12-membered N-containing heteroaryl, $C_3$-$C_6$ cycloalkyl, OH, —OC(O)R' or OR' wherein R' is unsubstituted $C_1$-$C_6$ alkyl; and a spiro group of the following formula:

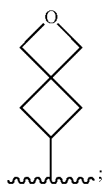 [SMILES: *C1CC2(COC2)C1]

Y is —CH₂—, —CH₂CH₂— or —CH₂CH₂CH₂—;

n is 0 or 1; and

R² is a group selected from $C_6$-$C_{10}$ aryl, $C_5$-$C_6$ heteroaryl, $C_3$-$C_6$ cycloalkyl and $C_5$-$C_6$ cycloalkenyl, wherein the group is unsubstituted or substituted and wherein $C_6$-$C_{10}$ aryl is optionally fused to a 5- or 6-membered heterocyclic ring;

or a pharmaceutically acceptable salt thereof.

2. A compound according to claim 1, wherein the benzimidazole has the following formula (Ia):

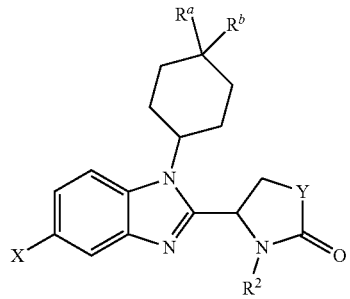
(Ia)

wherein

X, Y and R² are as defined in claim 1; and each of $R^a$ and $R^b$ is independently selected from H, halo, OH, —OC(O)R", —SO₂Me, —SO₂-cyclopropyl, oxo (=O), $C_1$-$C_6$ alkoxy, hydroxy($C_1$-$C_6$)alkyl, —NH₂, CN, —C(O)NHR", —NHC(O)R" and —COOR", where R" is H or $C_1$-$C_6$ alkyl optionally substituted by halo.

3. A compound according to claim 1 wherein R¹ is selected from the following structures:

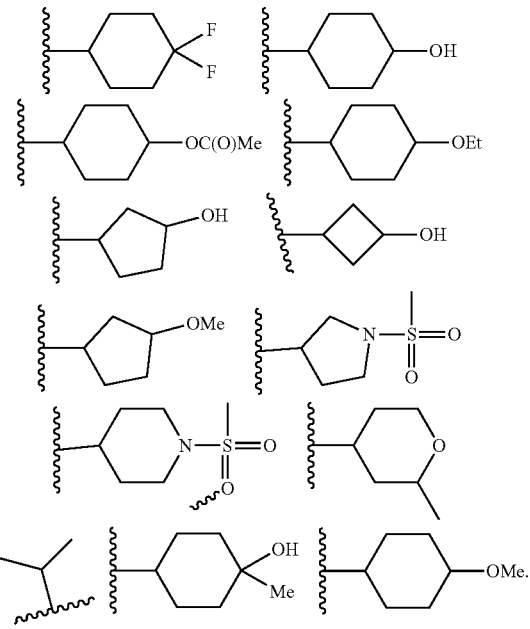

4. A compound according to claim 1 which is the S enantiomer (based on the chiral C atom of the pyrrolidin-2-one or piperidin-2-one ring).

5. A compound according to claim 1 which is selected from:

(1S,4r)-4-(2-((S)-1-(3,4-difluorophenyl)-5-oxopyrrolidin-2-yl)-5-(1,4-dimethyl-1H-1,2,3-triazol-5-yl)-1H-benzo[d]imidazol-1-yl)cyclohexyl acetate;

(S)-1-(3,4-difluorophenyl)-5-(5-(1,4-dimethyl-1H-1,2,3-triazol-5-yl)-1-((1r,4S)-4-hydroxycyclohexyl)-1H-benzo[d]imidazol-2-yl)pyrrolidin-2-one;

(S)-5-(1-(4,4-difluorocyclohexyl)-5-(1,4-dimethyl-1H-1,2,3-triazol-5-yl)-1H-benzo[d]imidazol-2-yl)-1-(3,4-difluorophenyl)pyrrolidin-2-one;

(S)-5-(1-(4,4-difluorocyclohexyl)-5-(1,4-dimethyl-1H-pyrazol-5-yl)-1H-benzo[d]imidazol-2-yl)-1-(3,4-difluorophenyl)pyrrolidin-2-one; and (S)-5-(1-(4,4-difluorocyclohexyl)-5-(1,4-dimethyl-1H-imidazol-5-yl)-1H-benzo[d]imidazol-2-yl)-1-(3,4-difluorophenyl)pyrrolidin-2-one;

(S)-1-(3-chloro-4-fluorophenyl)-6-(5-(1,4-dimethyl-1H-1,2,3-triazol-5-yl)-1-((trans)-4-hydroxycyclohexyl)-1H-benzo[d]imidazol-2-yl)piperidin-2-one;

(S)-1-(3,4-difluorophenyl)-6-(5-(1,4-dimethyl-1H-1,2,3-triazol-5-yl)-1-(cis-4-hydroxy-4-methylcyclohexyl)-1H-benzo[d]imidazol-2-yl)piperidin-2-one;

(S)-1-(3-chloro-4-fluorophenyl)-6-(5-(1,4-dimethyl-1H-1,2,3-triazol-5-yl)-1-(cis-4-hydroxy-4-methylcyclohexyl)-1H-benzo[d]imidazol-2-yl)piperidin-2-one;

(S)-1-(3,4-difluorophenyl)-6-(5-(1,4-dimethyl-1H-1,2,3-triazol-5-yl)-1-(trans-4-hydroxycyclohexyl)-1H-benzo[d]imidazol-2-yl)piperidin-2-one;

(S)-6-(1-(4,4-difluorocyclohexyl)-5-(1,4-dimethyl-1H-1,2,3-triazol-5-yl)-1H-benzo[d]imidazol-2-yl)-1-(3-fluoro-4-methoxyphenyl)piperidin-2-one;

(S)-1-(3,4-difluorophenyl)-6-(5-(1,4-dimethyl-1H-1,2,3-triazol-5-yl)-1-(trans-4-methoxycyclohexyl)-1H-benzo[d]imidazol-2-yl)piperidin-2-one;

(S)-6-(5-(1,4-dimethyl-1H-1,2,3-triazol-5-yl)-1-(trans-4-methoxycyclohexyl)-1H-benzo[d]imidazol-2-yl)-1-(3-fluoro-4-methoxyphenyl)piperidin-2-one;

(S)-6-(1-(4,4-difluorocyclohexyl)-5-(1,4-dimethyl-1H-1,2,3-triazol-5-yl)-1H-benzo[d]imidazol-2-yl)-1-(3,4-difluorophenyl)piperidin-2-one;

(S)-1-(3,4-difluorophenyl)-6-(5-(1,4-dimethyl-1H-pyrazol-5-yl)-1-(trans-4-hydroxycyclohexyl)-1H-benzo[d]imidazol-2-yl)piperidin-2-one;

(S)-1-(3,4-difluorophenyl)-6-(5-(1,4-dimethyl-1H-pyrazol-5-yl)-1-(cis-4-hydroxy-4-methylcyclohexyl)-1H-benzo[d]imidazol-2-yl)piperidin-2-one;

(S)-6-(1-(4,4-difluorocyclohexyl)-5-(1,4-dimethyl-1H-pyrazol-5-yl)-1H-benzo[d]imidazol-2-yl)-1-(3-fluoro-4-methoxyphenyl)piperidin-2-one;

(S)-6-(5-(1,4-dimethyl-1H-pyrazol-5-yl)-1-(trans-4-methoxycyclohexyl)-1H-benzo[d]imidazol-2-yl)-1-(3-fluoro-4-methoxyphenyl)piperidin-2-one;

(S)-1-(3,4-difluorophenyl)-6-(5-(1,4-dimethyl-1H-imidazol-5-yl)-1-(trans-4-hydroxycyclohexyl)-1H-benzo[d]imidazol-2-yl)piperidin-2-one;

(S)-1-(3,4-difluorophenyl)-6-(5-(1,4-dimethyl-1H-imidazol-5-yl)-1-(cis-4-hydroxy-4-methylcyclohexyl)-1H-benzo[d]imidazol-2-yl)piperidin-2-one;

(S)-6-(1-(4,4-difluorocyclohexyl)-5-(1,4-dimethyl-1H-imidazol-5-yl)-1H-benzo[d]imidazol-2-yl)-1-(3-fluoro-4-methoxyphenyl)piperidin-2-one;

(S)-6-(5-(1,4-dimethyl-1H-imidazol-5-yl)-1-(trans-4-methoxycyclohexyl)-1H-benzo[d]imidazol-2-yl)-1-(3-fluoro-4-methoxyphenyl)piperidin-2-one;

and the pharmaceutically acceptable salts thereof.

6. A process for producing a compound as defined in claim 1, which process comprises the Pd-catalysed cross-coupling of a compound of formula (II):

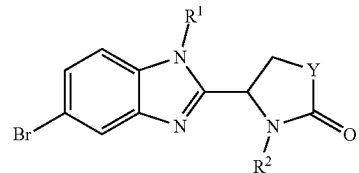

wherein each of $R^1$, Y and $R^2$ is as defined in claim 1, with a boronic acid of formula X—B(OH)$_2$ wherein X is as defined in claim 1; or the Pd-catalysed cross-coupling of a compound of formula (II'):

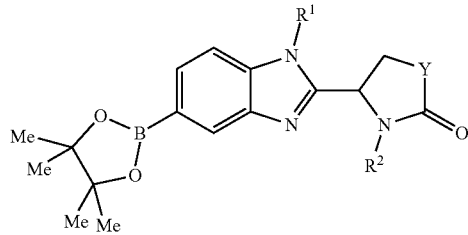

wherein each of $R^1$, Y and $R^2$ is as defined in claim 1, with a boronic acid of formula X—B(OH)$_2$ wherein X is as defined in claim 1; or the Pd-catalysed cross-coupling of a compound of formula (II'):

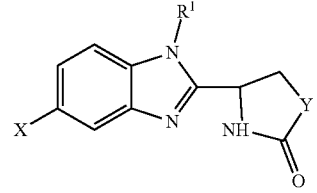

wherein each of X, $R^1$ and Y is as defined in claim 1, with a compound of formula $R^2$—CH$_2$Br in which $R^2$ is as defined in claim 1.

7. A process according to claim 6, which further comprises converting the resulting benzimidazole of formula (I) into a pharmaceutically acceptable salt thereof.

8. A pharmaceutical composition which comprises a pharmaceutically acceptable carrier or diluent and, as an active ingredient, a compound as defined in claim 1.

* * * * *